United States Patent [19]

Greenlee et al.

[11] Patent Number: 5,177,095

[45] Date of Patent: Jan. 5, 1993

[54] TRIAZOLE ANGIOTENSIN II ANTAGONISTS INCORPORATING A SUBSTITUTED BENZYL ELEMENT

[75] Inventors: William J. Greenlee, Teaneck; Arthur A. Patchett, Westfield, both of N.J.; David Hangauer, East Amherst, N.Y.; Wallace Ashton, Clark, N.J.; Kenneth J. Fitch, Cranford, N.J.; Thomas F. Walsh, Westfield, N.J.; Ralph A. Rivero, Eatontown, N.J.; Daljit S. Dhanoa, Tinton Falls, N.J.

[73] Assignee: Merck & Co., Inc., Rahway, N.J.

[21] Appl. No.: 744,554

[22] Filed: Aug. 13, 1991

Related U.S. Application Data

[63] Continuation-in-part of Ser. No. 671,598, Mar. 19, 1991, abandoned, which is a continuation-in-part of Ser. No. 479,779, Feb. 13, 1990, abandoned.

[51] Int. Cl.$^5$ .................. A61K 31/41; A01N 43/64; C07D 413/00; C07D 413/14; C07D 403/10; C07D 403/14; C07D 249/08
[52] U.S. Cl. .................. 514/384; 514/236.2; 514/236.5; 514/340; 514/369; 514/371; 544/124; 544/132; 544/141; 544/152; 544/157; 544/158; 544/159; 544/162; 544/170; 544/171; 546/276; 546/283; 548/182; 548/183; 548/185; 548/187; 548/189; 548/190; 548/191; 548/193; 548/194; 548/195; 548/196; 548/202; 548/204; 548/263.4; 548/264.2; 548/264.4; 548/266.6; 548/266.2; 548/266.4; 548/266.8

[58] Field of Search .............. 544/124, 132, 141, 152, 544/157, 158, 159, 162, 170, 171; 546/276, 283; 548/182, 183, 185, 187, 189, 190, 191, 193, 194, 195, 196, 202, 204, 263.4, 264.2, 264.4, 266, 269; 514/236.2, 236.5, 340, 369, 370, 371, 384

[56] References Cited

FOREIGN PATENT DOCUMENTS

| 429257 | 5/1991 | European Pat. Off. . |
|---|---|---|
| 430709 | 6/1991 | European Pat. Off. . |
| 434249 | 6/1991 | European Pat. Off. . |
| WO91/11909 | 8/1991 | PCT Int'l Appl. . |
| WO91/11999 | 8/1991 | PCT Int'l Appl. . |
| WO91/12001 | 8/1991 | PCT Int'l Appl. . |
| WO91/12002 | 8/1991 | PCT Int'l Appl. . |

Primary Examiner—Nicholas S. Rizzo
Assistant Examiner—Y. N. Gupta
Attorney, Agent, or Firm—Valerie J. Camara; William H. Nicholson; Joseph F. DiPrima

[57] ABSTRACT

Substituted triazoles attached through a methylene bridge to novel substituted phenyl derivatives of the Formula I, are useful as angiotensin II antagonists.

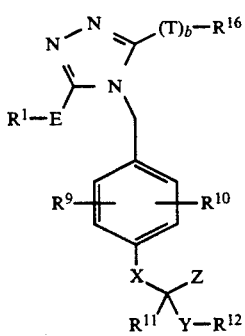

FORMULA I

9 Claims, No Drawings

TRIAZOLE ANGIOTENSIN II ANTAGONISTS INCORPORATING A SUBSTITUTED BENZYL ELEMENT

The present application is a continuation in part of copending application Ser. No. 671,598 filed on Mar. 19, 1991, now abandoned which is a continuation in part application of copending Ser. No. 479,779 filed on Feb. 13, 1990 (now abandoned).

BACKGROUND OF THE INVENTION

The Renin-angiotensin system (RAS) plays a central role in the regulation of normal blood pressure and seems to be critically involved in hypertension development and maintenance as well as congestive heart failure. Angiotensin II (A II), is an octapeptide hormone produced mainly in the blood during the cleavage of angiotensin I by angiotensin converting enzyme (ACE) localized on the endothelium of blood vessels of lung, kidney, and many other organs. It is the end product of the renin-angiotensin system (RAS) and is a powerful arterial vasoconstrictor that exerts its action by interacting with specific receptors present on cell membranes. One of the possible modes of controlling the RAS is angiotensin II receptor antagonism. Several peptide analogs of A II are known to inhibit the effect of this hormone by competitively blocking the receptors, but their experimental and clinical applications have been limited by partial agonist activity and lack of oral absorption [M. Antonaccio. *Clin. Exp. Hypertens.* A4, 27–46 (1982); D. H. P. Streeten and G. H. Anderson, Jr. - *Handbook of Hypertension, Clinical Pharmacology of Antihypertensive Drugs*, ed. A. E. Doyle, Vol. 5, pp. 246–271, Elsevier Science Publisher, Amsterdam, The Netherlands, 1984].

Recently, several substituted imidazoles have been described as A II antagonists. Illustrative of such compounds are those disclosed in U.S. Pat. Nos. 4,207,324; 4,340,598; 4,576,958; and 4,582,847; and 4,880,804 in European Patent Applications 028,834; 245,637; 253,310; 291,969; and 324,377 and in articles by A. T. Chiu, et al. [*Eur. J. Pharm. Exp. Therap*, 157, 13–21 (1988)] and by P. C. Wong, et al. [*J. Pharm. Exp. Therap*, 247, 1–7(1988)]. All of the U.S. Patents, European Patent Applications 028,834 and 253,310 and the two articles disclose substituted imidazole compounds which are generally bonded through a lower alkyl bridge to a substituted phenyl. European Patent Application 245,637 discloses derivatives of 4,5,6,7-tetrahydro-2H-imidazo[4,5-c]-pyridine-6-carboxylic acid and analogs thereof as antihypertensive agents.

The compounds disclosed within this application have not been identified in any U.S. Patents, European Applications or articles. The compounds of the present invention are substituted triazoles which are bonded through a methylene bridge to a novel substituted phenyl element. DuPont also has filed a European Application (EPO 0,323,841) covering substituted pyrroles, pyrazoles and triazoles. The present invention covers novel antagonists which incorporate a novel substituted benzyl element linked to the triazole moiety. The above cited applications are hereby incorporated by reference, serving as an information source as to the preparation of substituted triazoles. A pending Merck application, Ser. No. 382,138, discloses other novel triazoles and the synthetic routes to these triazoles are described in the Schemes I-1 through I-14 and the incorporation of the substituted benzyl element is described in Schemes I-15 through I-30.

The compounds of this invention have central nervous system (CNS) activity. They are useful in the treatment of cognitive dysfunctions including Alzheimer's disease, amnesia and senile dementia. These compounds also have anxiolytic and antidepressant properties and are therefore, useful in the relief of symptoms of anxiety and tension and in the treatment of patients with depressed or dysphoric mental states.

In addition, these compounds exhibit antidopaminergic properties and are thus useful to treat disorders that involve dopamine dysfunction such as schizophrenia. The compounds of this invention are especially useful in the treatment of these conditions in patients who are also hypertensive or have a congestive heart failure condition.

DETAILED DESCRIPTION OF THE INVENTION

This invention relates to compounds of Formula I:

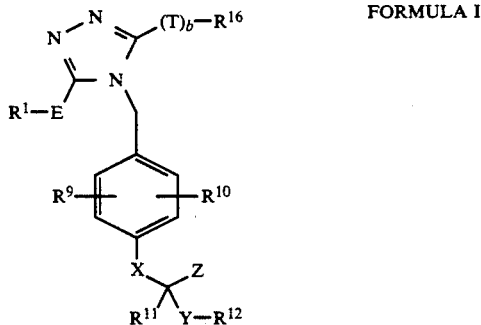

FORMULA I

Wherein $R^1$ is:

(a) $(C_1-C_6)$-alkyl, $(C_2-C_6)$-alkenyl or $(C_2-C_6)$-alkynyl each of which is unsubstituted or substituted with one or more substituents selected from the group consisting of:
  i) aryl, wherein aryl is defined as phenyl or naphthyl, unsubstituted or substituted with 1 or 2 substituents selected from the group consisting of:
    1) Cl, Br, I, F,
    2) $(C_1-C_4)$-alkyl,
    3) $(C_1-C_4)$-alkoxy,
    4) $NO_2$
    5) $CF_3$
    6) $SO_2NR^{2a}R^{2a}$,
    7) $(C_1-C_4)$-alkylthio,
    8) hydroxy,
    9) amino,
    10) $(C_3-C_7)$-cycloalkyl,
    11) $(C_3-C_{10})$-alkenyl; and
  ii) $(C_3-C_7)$-cycloalkyl,
  iii) Cl, Br, I, F, or
  iv) $COOR^2$,
  v) $-CF_2CF_3$, or
  vi) $-CH_2CF_3$; and
(b) $(C_1-C_4)$-perfluoroalkyl, or
(c) $(C_3-C_6)$-cycloalkyl, unsubstituted or substituted with one or more substituents from the group consisting of: $(C_1-C_4)$-alkoxy, $(C_1-C_4)$-alkyl- thio, $(C_1-C_4)$-perfluoroalkyl, hydroxy, or F, Cl, Br, I; and E is:
(a) a single bond, (b) —S(O)$_n$(CH$_2$)$_s$—, or
(c) —O—; and
n is 0 to 2; and
s is 0 to 5; and
R$^2$ is:
(a) H, or
(b) (C$_1$–C$_6$)-alkyl; and
R$^{2a}$ is:
(a) R$^2$,
(b) CH$_2$-aryl, or
(c) aryl; and
(d) when R$^2$ and R$^{2a}$ are alkyl substituents on the same nitrogen they can be joined to form a ring; and wherein there is more than one R$^{2a}$ group in the definition of a structure of Formula I they may be the same or different; and
R$^9$ and R$^{10}$ are independently:
(a) H,
(b) (C$_1$–C$_6$)-alkyl, unsubstituted or substituted with (C$_3$–C$_7$)-cycloalkyl,
(c) (C$_2$–C$_6$)-alkenyl,
(d) (C$_2$–C$_6$)-alkynyl,
(e) Cl, Br, F, I,
(f) (C$_1$–C$_6$)-alkoxyl,
(g) when R$^9$ and R$^{10}$ are on adjacent carbons, they can be joined to form an phenyl ring,
(h) (C$_1$–C$_6$)-perfluoroalkyl,
(i) (C$_3$–C$_7$)-cycloalkyl, unsubstituted or substituted with (C$_1$–C$_6$)-alkyl,
(j) aryl,
(k) C$_1$–C$_6$-alkyl—S(O)$_n$—(CH$_2$)$_n$—,
(l) hydroxy-(C$_1$–C$_6$)-alkyl,
(m) —CO$_2$R$^{2a}$,
(n) —OH,
(o) —NR$^2$R$^{21}$,
(p) —[(C$_1$–C$_6$)-alkyl]NR$^2$R$^{21}$,
(q) —NO$_2$,
(r) —(CH)$_n$—SO$_2$—N(R$^2$)$_2$,
(s) —NR$^2$CO—(C$_1$–C$_4$)-alkyl, or
(t) —CON(R$^2$)$_2$; and
X is:
(a) —O—,
(b) —S(O)$_n$—,
(c) —NR$^{13}$—
(d) —CH$_2$O—,
(e) —CH$_2$S(O)$_n$,
(f) —CH$_2$NR$^{13}$ —,
(g) —OCH$_2$—,
(h) —NR$^{13}$CH$_2$—,
(i) —S(O)$_n$CH$_2$—,
(j) —CH$_2$—,
(k) —(Ch$_2$)$_2$—,
(l) single bond, or (m) —CH=, wherein Y and R$^{12}$ are absent forming a —C=C— bridge to the carbon bearing Z and R$^{11}$; and
Y is:
(a) single bond;
(b) —O—,
(c) —S(O)$_n$—,
(d) —NR$^{13}$—, or
(e) —CH$_2$—; and except that X and Y are not defined in such a way that the carbon atom to which Z is attached also simultaneously is bonded to two heteroatoms (O, N, S, SO, SO$_2$);
R$^{11}$ and R$^{12}$ are independently:
(a) H,
(b) (C$_1$–C$_6$)-alkyl, unsubstituted or substituted with a substituent selected from the group consisting of:
(i) aryl,
(ii) (C$_3$–C$_7$)-cycloalkyl,
(iii) NR$^2$R$^{21}$,
(iv) morpholin-4-yl,
(v) OH,
(vi) CO$_2$R$^{21}$, or
(vii) CON(R$^2$)$_2$,
(c) aryl or aryl-(C$_1$–C$_2$)-alkyl, unsubstituted or substituted with 1 to 3 substituents selected from the group consisting of:
(i) Cl, Br, I, F,
(ii) (C$_1$–C$_6$)-alkyl,
(iii) [(C$_1$–C$_5$)-alkenyl]CH$_2$—,
(iv) [(C$_1$–C$_5$)-alkynyl]CH$_2$—,
(v) (C$_1$–C$_6$)-alkyl—S(O)$_n$—(CH$_2$)$_n$—,
(vi) —CF$_3$,
(vii) —CO$_2$R$^{2a}$,
(viii) —OH,
(ix) —NR$^2$R$^{21}$,
(x) —NO$_2$,
(xi) —NR$^2$COR$^2$,
(xii) —CON(R$^2$)$_2$,
(xiii) —G—[(C$_1$–C$_6$)-alkyl]-R$^{23}$,
(xiv) —N[CH$_2$CH$_2$]$_2$Q, or
(xv) —P(O)]O—(C$_1$–C$_4$)-alkyl]$_2$, and can additionally be substituted with 1 or 2 substituents selected from the group consisting of: Br, Cl or F,
(d) (C$_3$–C$_7$)-cycloalkyl, or
(e) when Y is single bond, R$^{11}$ and R$^{12}$ can be joined to form a ring of 5 to 7 carbon atoms, the ring can be benzo-fused and one carbon of which can be replaced with a heteroatom selected from the group consisting of: O, S(O)$_n$ and NR$^{22}$; and
G is: a single bond, O, S(O)$_n$ or NR$^{23}$; and
Q is: O, S(O)$_n$ or NR$^{22}$; and
R$^{13}$ is:
(a) H,
(b) (C$_1$–C$_6$)-alkyl,
(c) aryl,
(d) aryl-(C$_1$–C$_6$)-alkyl—(C=O)—,
(e) (C$_1$–C$_6$)-alkyl—(C=O)—,
(f) [(C$_2$–C$_5$)-alkenyl]CH$_2$—,
(g) [(C$_2$–C$_5$)-alkynyl]CH$_2$—, or
(h) aryl—CH$_2$—; and
Z is:
(a) —CO$_2$H,
(b) —CO$_2$R$^{24}$,
(c) —tetrazol-5-yl,
(d) —CO—NH(tetrazol-5-yl),
(e) —CONHSO$_2$-aryl,
(f) —CONHSO$_2$—(C$_1$–C$_8$)-alkyl, wherein the alkyl group is unsubstituted or substituted with a substituent chosen from the group consisting of: —OH, —SH, —O(C$_1$–C$_4$)-alkyl, —S—(C$_1$–C$_4$)-alkyl, —CF$_3$, Cl, Br, F, I, —NO$_2$, —CO$_2$H, —Co$_2$—(C$_1$–C$_4$)-alkyl, —NH$_2$, —NH[(C$_1$–C$_4$)-alkyl] and —N[(C$_1$–C$_4$)-alkyl]$_2$,
(g) —CONHSO$_2$—(C$_1$–C$_4$)-perfluoroalkyl,
(h) —CONHSO$_2$-heteroaryl, or
(i) —CONHSO$_2$NR$^{2a}$R$^{2a}$; and
(j) —SO$_2$NHCO-aryl,
(k) —SO$_2$NHCO-(C$_1$–C$_8$)-alkyl, wherein the alkyl group is unsubstituted or substituted with a substituent chosen from the group consisting of: —OH, —SH, —O(C$_1$–C$_4$)-alkyl, —S—(C$_1$–C$_4$)-alkyl, —CF$_3$, Cl, Br, F, I, —NO$_2$, —CO$_2$H, —CO$_2$—(C$_1$–C$_4$)-alkyl, —NH$_2$, —NH[(C$_1$–C$_4$)-alkyl], —N[(C$_1$4 C$_4$)-alkyl]$_2$; and
(l) —SO$_2$NHCO—(C$_1$–C$_4$)-perfluoroalkyl, (m) —SO$_2$NHCO-heteroaryl, or
(n) —SO$_2$NHCONR$^{2a}$R$^{2a}$; and
T is —S(O)$_n$—, —O—, —NHCH$_2$—, —NHC(=O)—, —C(=O)N(R$^{20}$)—, or —N(R$^{20}$)—; and
b is 0 or 1; and
R$^{15}$ is
(a) H,
(b) (C$_1$-C$_6$)-alkyl,
(c) phenyl, or
(d) benzyl; and
R$^{16}$ is
(a) (C$_1$-C$_{10}$)-alkyl;
(b) substituted (C$_1$-C$_{10}$)-alkyl in which one or more substituent(s) is selected from
(1) I, Br, Cl, F,
(2) hydroxy,
(3) (C$_1$-C$_{10}$)-alkoxy,
(4) (C$_1$-C$_5$)-alkoxycarbonyl,
(5) (C$_1$-C$_5$)-acyloxy,
(6) (C$_3$-C$_8$)-cycloalkyl,
(7) aryl,
(8) substituted aryl in which the substituents are V and W,
(9) (C$_1$-C$_{10}$)-alkyl—S(O)$_n$,
(10) (C$_3$-C$_8$)-cycloakyl—S(O)$_n$,
(11) phenyl—S(O)$_n$,
(12) substituted phenyl—S(O)$_n$ in which the substituents are V and W,
(13) oxo,
(14) carboxy,
(15) NR$^2$R$^{2a}$,
(16) (C$_1$-C$_5$)-alkylaminocarbonyl,
(17) di(C$_1$-C$_5$)-alkylaminocarbonyl, or
(18) cyano,
(c) (C$_1$-C$_4$)-perfluoroalkyl,
(d) (C$_2$-C$_{10}$)-alkenyl,
(e) (C$_2$-C$_{10}$)-alkynyl,
(f) (C$_3$-C$_8$)-cycloalkyl,
(g) substituted (C$_3$-C$_8$)-cycloalkyl in which the substituent is selected from:
(1) (C$_1$-C$_5$)-alkyl, or
(2) (C$_1$-C$_5$)-alkoxy,
(3) (C$_1$-C$_5$)-alkoxycarbonyl,
(4) (C$_1$-C$_5$)-acyloxy,
(C$_1$-C$_5$)-acyl,
(6) hydroxy,
(7) Br, Cl, F, I,
(8) (C$_3$-C$_8$)-cycloalkyl,
(9) aryl,
(10) substituted aryl in which the substituents are V and W,
(11) (C$_1$-C$_{10}$)-alkyl—S(O)$_n$,
(12) (C$_3$-C$_8$)-cycloalkyl—S(O)$_n$,
(13) phenyl—S(O)$_n$,
(14) substituted phenyl—S(O)$_n$ in which the substituents are V and W,
(15) oxo,
(16) carboxy,
(17) NR$^2$R$^{2a}$,
(18) (C$_1$-C$_5$)-alkylaminocarbonyl,
(19) di(C$_1$-C$_5$)-alkylaminocarbonyl, or
(20) cyano,
(h) CO$_2$R$^{2a}$,
(i) aryl,
(j) substituted aryl in which the substituents are V and W,
(k) aryl—(CH$_2$)$_r$—(M$_1$)$_z$—(CH$_2$)$_r$—
(l) substituted aryl—(CH$_2$)$_r$—(M$_1$)$_z$—(CH$_2$)$_r$— in which the aryl group is substituted with V and W,

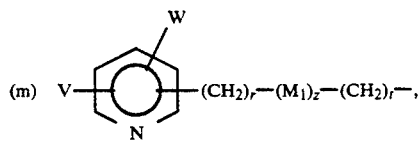

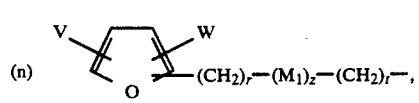

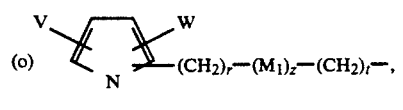

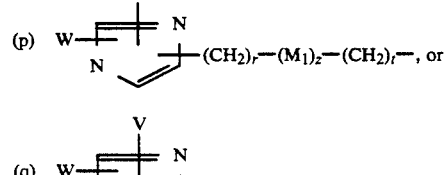

M$_1$ is O, S, —N(R$^{15}$)—, or —C(O)—; and
z is 0 or 1; and
r and t are 0 to 2; and
V and W are each independently selected from:
(a) H,
(b) (C$_1$-C$_5$)-alkoxy,
(c) (C$_1$-C$_5$)-alkyl,
(d) hydroxy,
(e) ((C$_1$-C$_5$)-alkyl)S(O)$_n$,
(f) —CN,
(g) —NO$_2$,
(h) —NR$^2$R$^{2a}$,
(i) [(C$_1$-C$_5$)-alkyl)]CO—NR$^2$R$^{2a}$,
(j) —CO$_2$R$^{2a}$,
(k) [(C$_1$-C$_5$)—alkyl)]CO—,
(l) CF$_3$,
(m) hydroxy-(C$_1$-C$_4$)-alkyl-,
(o) carboxy-(C$_1$-C$_4$)-alkyl-,
(p) —tetrazol-5-yl,
(q) —NHSO$_2$CF$_3$,
(r) aryl,
(s) —O—CONR$^2$R$^{2a}$,
(t) —NR$^{2a}$CO$_2$R$^{2a}$,
(u) —NR$^{2a}$CONR$^{2a}$R$^{2a}$,
(v) —NR$^{2a}$CON(CH$_2$CH$_2$)$_2$Q$_1$,
(w) —OCON(CH$_2$CH$_2$)$_2$Q$_1$, or
(x) —CONR$^2$R$^{2a}$; and
Q$_1$ is: O, S(O)$_n$, or NR$^{2a}$; and
R$^{18}$ is:
(a) phenyl, unsubstituted or substituted with: V and W,
(b) (C$_1$-C$_4$)-alkyl, or
(c) (C$_1$-C$_4$)-perfluoroalkyl; and
R$^{20}$ is
(a) H,
(b) (C$_1$-C$_6$)-alkyl,
(c) allyl,
(d) (C$_3$-C$_6$)-cycloalkyl,
(e) (C$_1$-C$_4$)-acyl,
(f) benzyl, or (g) phenyl; and R²¹ is:
(a) H, or
(b) $(C_1-C_4)$-alkyl, is unsubstituted or substituted with:
i) $NH_2$,
ii) $NH[(C_1-C_4)$-alkyl],
iii) $N[(C_1-C_4)$-alkyl]$_2$,
iv) $CO_2H$,
v) $CO_2(C_1-C_4)$-alkyl,
vi) OH,
vii) $SO_3H$, or
viii) $SO_2NH_2$; and R²² is:
(a) H,
(b) $(C_1C_4)$-alkyl,
(c) $(C_1-C_4)$-alkoxyl,
(d) aryl,
aryl-$(C_1-C_4)$-alkyl,
(f) $CO_2R^{2a}$,
(g) $CON(R^2)_2$,
(h) $SO_2R^{2a}$,
(i) $SO_2N(R^2)_2$,
(j) $P(O)[(C_1-C_4)$-alkoxyl]$_2$, or
(k) imidazol-2-yl or imidazol-4-yl, in which the imidazole can be substituted with $(C_1-C_4)$-alkyl; and R²³ is:
(a) OH,
(b) $NR^2R^{21}$,
(c) $CO_2R^{2a}$,
(d) $CON(R^2)_2$, or
(e) $S(O)_n-(C_1-C_4)$-alkyl; and R²⁴ is:
(a) $(C_1-C_4)$-alkyl,
(b) $CHR^{26}-O-COR^{27}$,
(c) $CH_2CH_2-N[(C_1-C_2)$-alkyl]$_2$,
(d) $CH_2CH_2-N[CH_2]_2O$,
(e) $(CH_2CH_2O)_y-O-[(C_1-C_4)$-alkyl], wherein y is 1 or 2,
(f) aryl,

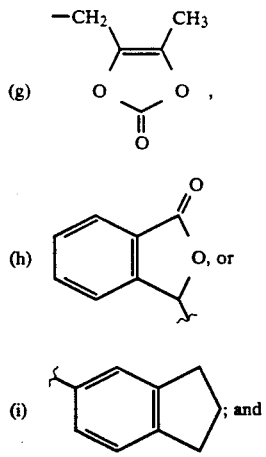

R²⁵ is:
(a) H,
(b) $(C_1-C_6)$-alkyl,
(c) aryl, or
(d) aryl-$(C_1-C_5)$-alkyl; and R²⁶ and R²⁷ independently are $(C_1-C_6)$ -alkyl or phenyl; or a pharmaceutically acceptable salt thereof.

The alkyl substituents recited above denote straight and branched chain hydrocarbons of the length specified such as methyl, ethyl, isopropyl, isobutyl, neopentyl, isopentyl, etc.

The alkenyl and alkynyl substituents denote alkyl groups as described above which are modified so that each contains a carbon to carbon double bond or triple bond, respectively, such as vinyl, allyl and 2-butenyl.

Cycloalkyl denotes rings composed of 3 to 8 methlene groups, each which may be substituted or unsubstituted with other hydrocarbon substituents, and include for example cyclopropyl, cyclopentyl, cyclohexyl and 4-methylcyclohexyl.

The alkoxy substituent represents an alkyl group as described above attached through an oxygen bridge.

The heteroaryl substituent recited above represents any 5- or 6-membered aromatic ring containing from one to three heteroatoms selected from the group consisting of nitrogen, oxygen, and sulfur, for example, pyridyl, thienyl, furyl, imidazolyl, and thiazolyl.

The preferred compounds of this invention are:

3-Butyl-4-[[4-(1-carboxy-1-phenylmethoxy)phenyl]-methyl]-5-(4-nitrobenzylthio)-4H-1,2,4-triazole.

3-Butyl-4-[[4-(1-carboxy-1-phenylmethoxy)phenyl]-methyl]-5-(4-nitrobenzylsulfinyl)-4H-1,2,4-triazole.

3-Butyl-4-[[4-[1-carboxy-1-(2-chlorophenyl)methoxy]phenyl]methyl-5-(4-nitrobenzylthio)-4-H-1,2,4-triazole.

3-Butyl-4-[]4-[1-carboxy-1-(2-methylphenyl)methoxy]phenyl]methyl]-5-(4-nitrobenzylthio)-4H-1,2,4-triazole.

3-Butyl-4-[[4-(1-carboxy-1-phenylmethoxy)phenyl]-methyl]-5-(4-methoxybenzylthio)-4H-1,2,4-triazole.

3-Butyl-4-[[4-(1-carboxy-1-phenylmethoxy)phenyl]-methyl]-5-(4-methoxybenzylsulfinyl)-4H-1,2,4-triazole.

3-Butyl-4-[[4-[1-carboxy-1-(2-chlorophenyl)methoxy]phenyl]methyl]-5-(4-methoxybenzylthio)-4H-1,2,4-triazole.

3-Butyl-4-[[4-[1-carboxy-1-(2-methylphenyl)methoxy]phenyl]methyl]-5-(4-methoxybenzylthio)-4H-1,2,4-triazole.

3-Butyl-5-(2-carboxybenzylthio)-4-[[4-(1-carboxy-1-phenylmethoxy)phenyl]methyl-4 H-1,2,4-triazole.

3-Butyl-5-(2-carboxybenzylthio)-4-[[4-[1-carboxy-1-(2-chlorophenyl)methoxy]phenyl ]methyl]-4H-1,2,4-triazole.

3-Butyl-5-(2-carboxybenzylthio)-4-[[4-[1-carboxy-1-(2-methylphenyl)methoxy]phenyl ]methyl]-4H-1,2,4-triazole.

3-Butyl-4-[[4-[1-carboxy-1-phenylmethoxy]phenyl]-methyl]-5-(4-chlorobenzylthio)-4H-1,2,4-triazole.

3-Butyl-4-[[4-[1-carboxy-1-(2-methylphenyl)methoxy]phenyl]methyl]-5-(4-chlorobenzylthio)-4H-1,2,4-triazole.

3-Butyl-4-[[4-[1-carboxy-1-phenylmethoxy[phenyl]-methyl]-5-(4-methylbenzylthio)-4H-1,2,4-triazole.

3-Butyl-4-[[4-[1-carboxy-1-(2-chlorophenyl)methoxy]phenyl]methyl]-5-(4-methylbenzylthio)-4H-1,2,4-triazole.

3-Butyl-5-(4-nitrobenzylthio)-4-[[4-[1-phenyl-1-(5-tetrazolyl)methoxy]phenyl ]methyl]-4H-1,2,4-triazole.

3-Butyl-4-[[4-[1-phenyl-1-(5-tetrazolyl)methoxy]-phenyl]methyl]-5-(4  -nitrobenzylsulfinyl)-4H-1,2,4-triazole.

3-Butyl-4-[[4-[1-(2-chlorophenyl)-1-(5-tetrazolyl)methoxy]phenyl]methyl]-5-(4nitrobenzylthio)-4H-1,2,4-triazole.

3-Butyl-5-(4-methoxybenzylthio)-4-[[4-[1-phenyl-1-(5-tetrazolyl)methoxy]phenyl ]methyl]-4H-1,2,4-triazole.

3-Butyl-5-(4-methoxybenzylthio)-4-[[4-[1-(2-chlorophenyl)-1-(5-tetrazolyl) methoxy]phenyl]methyl]-4H-1,2,4-triazole.

3-Butyl-5-(4-methoxybenzylthio)-4-[[4-[1-(2-methylphenyl)-1-(5-tetrazolyl) methoxy]phenyl]methyl]-4H-1,2,4-triazole.

3-Butyl-5-(2-carboxybenzylthio)-4-[[4-[1-phenyl-1-(5-tetrazolyl)methoxy]phenyl]methyl]-4H-1,2,4-triazole.

3-Butyl-5-(2-carboxybenzylthio)-4-[[4-]1-(2-chlorophenyl)-1-(5-tetrazolyl) methoxy]phenyl]methyl-4H-1,2,4-triazole.

3-Butyl-5-(4-chlorobenzylthio)-4-[[4-[1-phenyl-1-(5-tetrazolyl)methoxy]phenyl]methoxy]phenyl]methyl]-4-H-1,2,4-triazole.

3-Butyl-5-(4-chlorobenzylthio)-4-[[4-[1-(2-chlorophenyl)-1-(5-tetrazolyl) methoxy]phenyl]methyl]-4H-1,2,4-triazole.

3-Butyl-4-[[4-[1-carboxy-1-(2,6-dichlorophenyl)methoxy]phenyl]methyl]-5-(4-methoxybenzylthio)-4H-1,2,4-triazole.

3-Butyl-4-[[4-[1-carboxy-1-(2-methoxyphenyl)methoxy]phenyl]methyl]-5-(4-chlorobenzylthio)-4H-1,2,4-triazole.

3-Butyl-4-[[4-[(1-carboxy-1-phenylmethyl)amino]phenyl]methyl]-5-(4-methoxybenzylthio) -4H-1,2,4-triazole.

3-Butyl-4-[[4-[[1-carboxy-1-(2-chlorophenyl)methyl]amino]phenyl]methyl]-5-(4-nitrobenzylthio)-4H-1,2,4-triazole.

3-Butyl-4-[[4-(1-carboxy-1-phenylmethoxy)phenyl]methyl]-5-(4-chlorobenzylsulfinyl)-4H-1,2,4-triazole.

3-Butyl-4-[[4-[1-carboxy-1-(2-chlorophenyl)methoxy]phenyl]methyl]-5-(4-chlorobenzylthio)-4H-1,2,4-triazole.

3-Butyl-4-[[4-[1-carboxy-1-(2-chlorophenyl)methoxy]phenyl]methyl]-5-(4-chlorobenzylsulfinyl)-4H-1,2,4-triazole.

3-Butyl-4-[[4-(1-carboxy-1-phenylmethoxy)-3-propylphenyl]methyl]-5-phenyl-4H-1,2,4-triazole.

3-Butyl-4-[[4-(1-carboxy-1-phenylmethoxy)-3-propylphenyl]methyl]-5-(4-chlorobenzylthio)-4H-1,2,4-triazole.

3-Butyl-4-[[4-(1-carboxy-1-phenylmethoxy)-3-propylphenyl]methyl]-5-(4-methoxybenzylthio)-4H-1,2,4-triazole.

3-Butyl-4-[[4-[1-carboxy-1-(2-chlorophenyl)methoxy]-3-propylphenyl]methyl]-5-(4-chlorobenzylthio)-4H-1,2,4-triazole.

3-Butyl-4-[[4-[1-carboxy-1-(2-chlorophenyl)methoxy]3-propylphenyl]methyl]-5-(4-methoxybenzylthio)-4H-1,2,4-triazole.

3-Butyl-4-[[4-[1-carboxy-1-(2-methylphenyl)methoxy]3-chlorophenyl]methyl]-5-(4-chlorobenzylthio)-4H-1,2,4-triazole.

3-Butyl-4-[[4-(1-carboxy-1-phenylmethoxy)-3,5-dipropylphenyl]methyl]-5-(4-chlorobenzylthio)-4H-1,2,4-triazole.

3-Butyl-4-[[4-(1-carboxy-1-phenylmethoxy)-3,5-dipropylphenyl]methyl]-5-(4-methoxybenzylthio)-4H-1,2,4-triazole.

3-Butyl-4-[[4-[1-carboxy-1-(2,5-dibromo-3,4-dimethoxyphenyl)methoxy]phenyl]methyl ]-5-(4-chlorobenzylthio)-4H-1,2,4-triazole.

3-Butyl-4-[[4-[1-carboxy-1-(2,5-dibromo-3,4-dimethoxyphenyl)methoxy]phenyl]methyl ]-5-(4-methoxybenzylthio)-4H-1,2,4-triazole.

3-Butyl-5-(2-carboxybenzylthio)-4-[[4-(1-carboxy-1-phenylmethoxy)-3-propylphenyl ]methyl]-4-H-1,2,4-triazole.

3-Butyl-5-(2-carboxybenzylthio)-4-[[4-(1-carboxy-1-(2-chlorophenyl)methoxy)-3-propylphenyl]methyl]-4H-1,2,4-triazole. 3-Butyl-5-(2-carboxybenzylthio)-4-[[4-(1-carboxy-1-(2-methylphenyl)methoxy]-3-chlorophenyl]methyl]-4H-1,2,4-triazole.

3-Butyl-5-(2-carboxybenzylthio)-4-[[4-(1-carboxy-1-phenylmethoxy)-3,5-dipropylphenyl ]methyl]-4H-1,2,4-triazole.

3-Butyl-5-(2-carboxybenzylthio)-4-[[4-[1-carboxy-1-(2,5-dibromo-3, 4-dimethoxyphenyl)methoxy]phenyl]methyl]-4H-1,2,4-triazole.

4-[[[N-Allyl-N-[(1-carboxy-1-phenyl)methyl]amino]phenyl]methyl]-3-butyl-5-(4-chlorobenzylthio)-4H-1,2,4-triazole.

4-[[[N-Allyl-N-[(1-carboxy-1-phenyl)methyl]amino]phenyl]methyl]-3-butyl-5-(4-methoxybenzylthio)-4H-1,2,4-triazole.

4-[[[N-Allyl-N-[(1-carboxy-1-phenyl)methyl]amino]phenyl]methyl]-3-butyl-5-(2-carboxybenzylthio)-4H-1,2,4-triazole.

2-Butyl-4-[[[N-[(1-carboxy-1-phenyl)methyl]-N-ethylamino]phenyl]methyl]-5-(4-chlorobenzylthio)4H-1,2,4-triazole.

Preparation of 3,4,5-trisubstituted-1,2,4-triazoles
(Formula I)

The compounds of Formula I can be prepared by a variety of methods typified by those described below. General synthetic methods for 3,4,5-trisubstituted 1,2,4-triazoles are discussed in books or review articles such as:

(1) C. Temple and J. A. Montgomery, "Triazoles: 1,2,4" (Vol. 37 of "The Chemistry of Heterocyclic Compounds", A. Weissberger and E. C. Taylor, eds.), Wiley-Interscience, New York, 1981.

(2) J. B. Polya, in "Comprehensive Heterocyclic Chemistry. The Structure, Reactions, Synthesis and Uses of Heterocyclic Compounds", A. R. Katritzky and C. W. Rees, eds., Vol. 5, Pergamon Press, Oxford, 1984, pp. 733-790.

(3) J. H. Boyer, in "Heterocyclic Compounds", R. C. Elderfield, ed., Vol. 7, John Wiley & Sons, New York, 1961, pp. 384-461.

In general, the compounds of Formula I are constructed in such a way that $N^1$ and $N^2$ of the triazole ring are derived from hydrazine or a hydrazine derivative, while $N^4$ of the triazole and the 4-(arylmethyl) substituent are derived directly or indirectly from a suitably substituted benzylamine.

Although the reaction schemes described below are reasonably general, it will be understood by those skilled in the art of organic synthesis that one or more functional groups present in a given compound of Formula I may render the molecule incompatible with a particular synthetic sequence. In such a case an alternative route, an altered order of steps, or a strategy of protection and deprotection may be employed. In all cases the particular reaction conditions, including reagents, solvent, temperature, and time, should be chosen so that they are consistent with the nature of the functionality present in the molecule.

The Reaction Schemes below have been generalized for simplicity. It is to be understood that the "ArCh$_2$" substituent present at $N^4$ of the triazole derivatives or in their precursors is any substituted arylmethyl moiety consistent with the definition of the $N^4$ substituent in Formula I or which may be transformed to such a grouping either before or after the assembly of the triazole ring system. Such transformations may involve protection and/or deprotection as shown in Formula I, or other modifications. It is also to be understood that in most of the Reaction Schemes, the "ArCh$_2$" (Ar=aryl) substituent is consistent with the definition of Formula I.

Abbreviations used in the schemes and examples below are listed in Table 1.

TABLE 1

| Reagents | |
|---|---|
| NBS | N-bromosuccinimide |
| AIBN | Azobis(isobutyronitrile) |
| DDQ | Dichlorodicyanoquinone |
| Ac$_2$O | acetic anhydride |
| TEA | triethylamine |
| DMAP | 4-dimethylaminopyridine |
| PPh$_3$ | triphenylphosphine |
| TFA | trifluoroacetic acid |
| TMS-Cl | trimethylsilyl chloride |
| Im | imidazole |
| AcSK | potassium thioacetate |
| p-TsOH | p-toluenesulfonic acid |
| Solvents: | |
| DMF | dimethylformamide |
| HOAc (AcOH) | acetic acid |
| EtOAc (Etac) | ethyl acetate |
| Hex | hexane |
| THF | tetrahydrofuran |
| DMSO | dimethylsulfoxide |
| MeOH | methanol |
| iPrOH | isopropanol |
| Others: | |
| rt | room temperature |
| TBDMS | t-butyldimethylsilyl |
| OTf | OSO$_2$CF$_3$ |
| Ph | phenyl |
| FAB-MS | Fast atom bombardment mass spectroscopy |
| NOE | Nuclear Overhauser Effect |

TABLE 1-continued

| SiO$_2$ | silica gel |
|---|---|
| trityl | triphenylmethyl |

The compounds of the present invention may be resolved using the techniques known in the art. The diastereomeric salts and esters of the enantiomers are separated and the desired compound is the more active stereoisomer. The invention is intended to include individual stereoisomers as well as racemic mixtures. The compounds of this invention, their pharmaceutically acceptable salts and their prodrug forms are included within the scope of this invention.

It is further to be understood that in the generalized schemes below, unless specified more narrowly in the text, the groups $R^1$ and $R^{16}$ represent functionalized or unfunctionalized alkyl, aryl, heteroaryl, aralkyl, and the like. The moiety $R^{16}Q$ represents an alkylating agent in which $R^{16}$ is typically a functionalized or unfunctionalized alkyl or aralkyl group, while Q is a leaving group such as chloro, bromo, iodo, methanesulfonate, or p-toluenesulfonate.

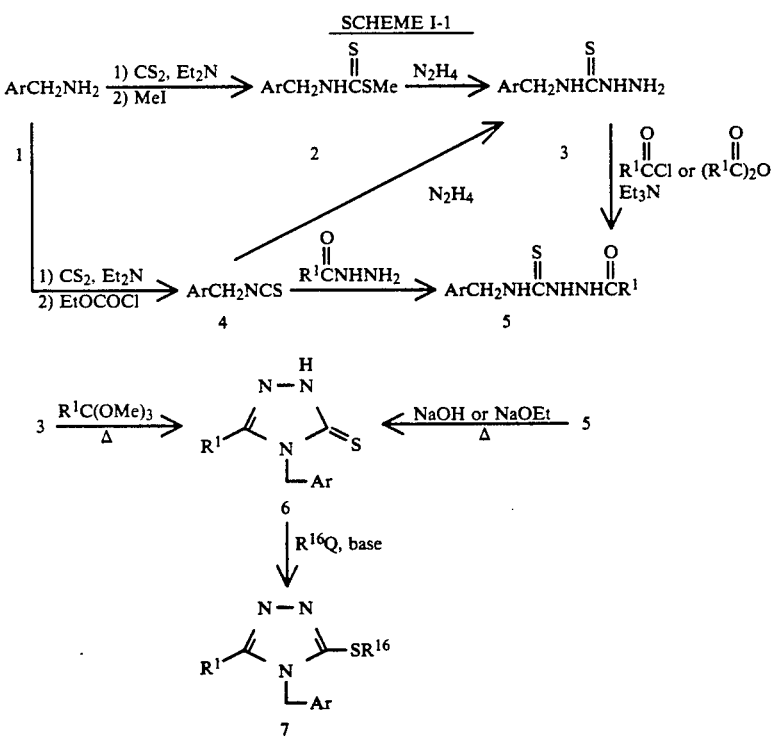

SCHEME I-1

Scheme I-1 outlines some of the most widely applicable routes to compounds of Formula I in which either the 3- or 5-substituent is substituted thio. Thus an appropriate benzylamine 1 may be converted to dithiocarbamate ester 2 in a one-pot two-step sequence involving treatment with carbon disulfide in the presence of a base such as triethylamine followed by alkylation with methyl iodide. Treatment of 2 with hydrazine (preferably in excess) affords the 4-substituted thiosemicarbazide 3. This is also readily obtained upon reaction of hydrazine with the isothiocyanate 4, which in turn is prepared from amine 1 [for example, via an intermediate carbethoxy dithiocarbamate (J. E. Hodgkins and M. G. Ettlinger, J. Org. Chem., 21, 404 (1956)) or by one of the other methods known in the literature]. The acylthiosemicarbazide 5 may be prepared either by reaction of 3 with the appropriate acid chloride or anhydride or by addition of an acid hydrazide (readily obtained from the corresponding ester) to the isothiocyanate 4. As described in G. F. Duffin, J. D. Kendall, and H. R. J. Waddington, *J. Chem. Soc.*, 3799 (1959), S. M. El-Khawass and N. S. Habib, *J. Heterocyclic Chem.*, 26, 177 (1989), and numerous other papers, acylthiosemicarbazides related to 5 can by cyclized in the presence of hydroxide or alkoxide to the mercaptotriazoles (best represented as triazolinethiones) corresponding to 6. Compounds of type 6 can also be prepared by direct reaction of the thiosemicarbazide derivative 3 with an appropriate acid derivative. For example, reaction of 3 with a trimethyl orthoester at elevated temperature in a suitable solvent (such as 2-methoxyethanol at reflux) yields 6. Similar syntheses of mercaptotriazoles have been reported by G. A. Reynolds and J. A. Van Allan, *J. Org. Chem.*, 24, 1478 (1959). Other acid derivatives such as esters [in the presence of alkoxide: M. Pesson, G. Polmanss, and S. Dupin, *Compt. Rend.*, 248, 1677 (1959)] and selenoesters [V. I. Cohen, *J. Heterocyclic Chem.*, 15, 237, (1978)] have also been reported to react with 4-substituted thiosemicarbazides to give mercaptotriazoles analogous to 6. In certain instances the carboxylic acid itself may be used. Thus, 4-substituted thiosemicarbazides have been reacted with trifluoroacetic acid at elevated temperature to give mercaptotriazoles analogous to 6 (R=CF3) [T. Cebalo, U.S. Pat. No. 3,625,951 (1971) and E. I. Aoyagi, U.S. Pat. No. 4,477,459 (1984)].

The S-alkylated mercaptotriazoles of structure 7 are obtained by treatment of the triazolinethione 6 with an appropriate alkylating agent $R^{16}Q$ in which $R^{16}$ is functionalized or unfunctionalized alkyl, aralkyl, heterocyclyl, or the like, and Q is a leaving group such as chloro, bromo, iodo, methanesulfonate, or p-toluenesulfonate. This alkylation is conducted in any of a variety of solvents (including methanol, ethanol, 2-methoxy-ethanol, tetrahydrofuran, N,N-dimethylformamide, dichloromethane and water, depending on the properties of the particular substituents) in the presence of a base (such as a trialkylamine, alkoxide, or hydroxide). Triazolinethiones (mercaptotriazoles) are known to give the S-alkylated derivatives predominantly if not exclusively under basic conditions (see, for example, C. Temple and J. A. Montgomery, "Triazoles: 1,2,4", Wiley-Interscience, New York, 1981, pp. 251-258). The alkylation reaction is generally run at a temperature of from 0° C. to 125° C., depending on the reactivity of the alkylating agent.

The triazolinethiones 6 may be prepared by alternative routes. In the method of F. Malbec, R. Milcent, and G. Barbier [*J. Heterocycl. Chem.*, 21, 1689 (1984)] (Scheme I-2), the imidate hydrochloride 8 is reacted with thiosemicarbazide at ambient temperature to give the ester thiosemicarbazone 9. The conversion of 9 to the triazolinethione 6 can be effected by heating with amine 1 in DMF at reflux. Similarly, an $N^4$-substituted ester thiosemicarbazone 9a, which is obtained by reaction of 8 with 3, can be cyclized to 6 by heating in the presence of a base, e.g., 1,8-diazabicyclo{5.4.0}undec-7-ene (DBU), in a solvent such as tetrahydrofuran.

SCHEME I-2

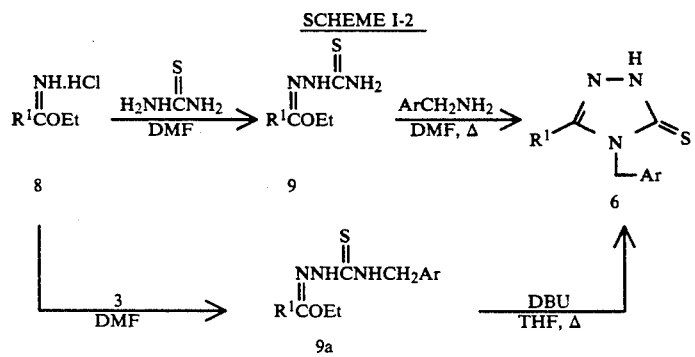

For triazolinethiones of type 6 where $R^1$=aryl, the method of T. Radha Vakula, V. Ranga Rao, and V. R.Srinivasan [*Indian J. Chem.*, 7, 577 (1969)](Scheme I-3) is applicable. Thus the thiosemicarbazide derivative 3 is condensed with an aromatic aldehyde 10 to give the thiosemicarbazone 11. Upon treatment of 11 with bromine in acetic acid, the triazolinethione 12 is formed.

SCHEME I-3

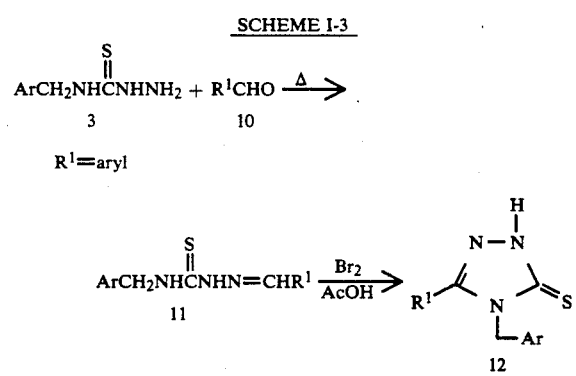

Following the method of L. Strzemecka [*Polish J. Chem.*, 57 561 (1983)] (Scheme I-4), reaction of an amidrazone 13 with the isothiocyanate 4 in ethanol at reflux gives triazolinethione 6.

SCHEME I-4

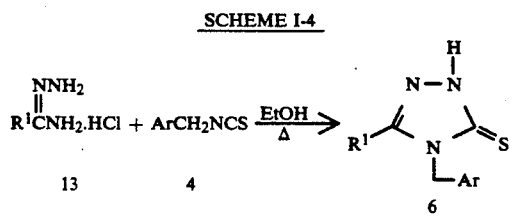

Certain S-substituted mercaptotriazoles of formula 7 which may not be accessible by the reactions of Scheme I-1 (especially $R^{16}$=aryl) can be prepared by an alternative route (Scheme I-5) involving displacement of a leaving group on the triazole by an appropriate thiol. Treatment of the triazolinethione 6 with chlorine under anhydrous conditions in a solvent such as chloroform or dichloromethane gives as a major product the chlorotriazole 14 [D. S. Deshpande, T. G. Surendra Nath, and V. R. Srinivasan, *Indian J. Chem.*, 13, 852 (1975)]. In addition, the synthesis of chlorotriazoles by POCl$_3$/PCl$_5$ treatment of the corresponding triazolinone has been reported [S. Naqui and V. R. Srinivasan, *J. Sci. Industr. Res.*, 21B, 195, (1962)]. Reaction of 14 with a thiophenol or other thiol in the presence of a base such as N,N-diisopropylethylamine at elevated temperature (for example, in DMF at reflux) gives 7. Similar reactions have been reported by H. Becker and K. Wehner, British Patent 1,157,256 (1969).

Whether 17 or 18 is the primary or exclusive product depends on the stoichiometry of the reagents, reaction time, and temperature.

SCHEME I-7

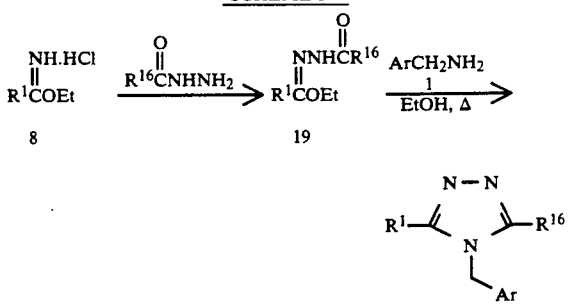

SCHEME I-5

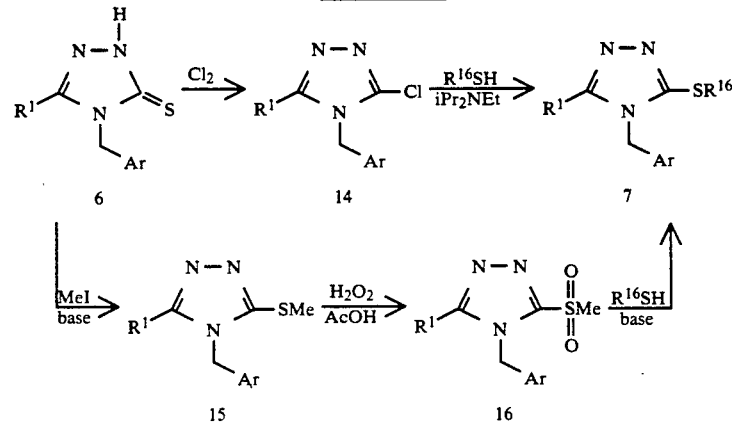

Alternatively, the methylthiotriazole 15 may be prepared (by alkylation of 6 with methyl iodide) and then oxidized to the methylsulfone 16 using hydrogen peroxide. Displacement of the methanesulfonyl group of 16, like the chloro group of 14, by R$^{16}$SH in the presence of a base affords 7, especially for R$^{16}$=aryl. The preparation of a methanesulfonyltriazole analogous to 16 and its nucleophilic displacement have been reported by E. B. Akerblom and D. E. S. Campbell, *J. Med. Chem.*, 16, 312 (1973).

The method of R. Kraft, H. Paul, and G. Hilgetag [*Chem. Ber.*, 101, 2028 (1968)] (Scheme I-7) is useful for preparing triazoles of structure 20 in which R$^{16}$ is aryl or heterocyclic. Treatment of the imidate hydrochloride 8 with an appropriate hydrazide (typically at −10° to 5° C.) gives the adduct 19, which can be reacted with the amine 1 and cyclized to the triazole 20 upon heating in ethanol. By use of the adaption of M. Pesson and M. Antoine [Bull. Soc. Chim. Fr., 1590 (1970)], triazoles of type 20 in which R$^{16}$ is a substituted carboxamide group are obtained by employing a substituted oxamic acid hydrazide in Scheme I-7.

SCHEME I-6

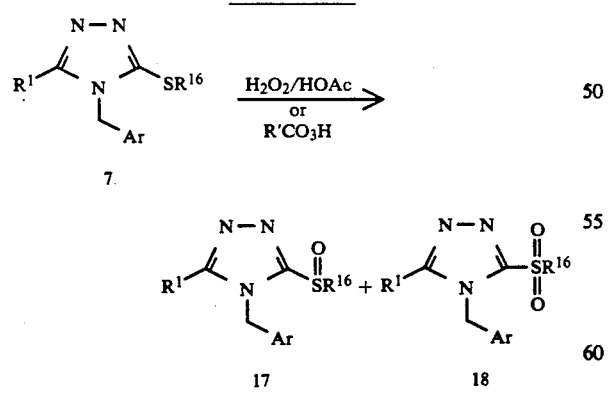

The S-substituted mercaptotriazoles 7 can be converted to the corresponding sulfoxides 17 and/or sulfones 18 by oxidation with various reagents such as hydrogen peroxide in acetic acid or a suitable peracid. Reactions of this type have been described by E. B. Akerblom and D. E. S. Campbell (see reference above).

SCHEME I-8

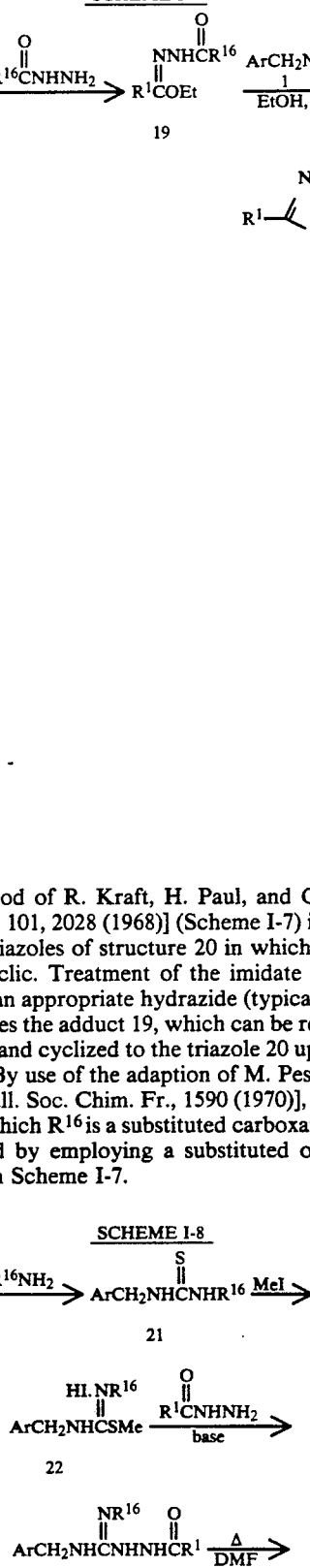

-continued
SCHEME I-8

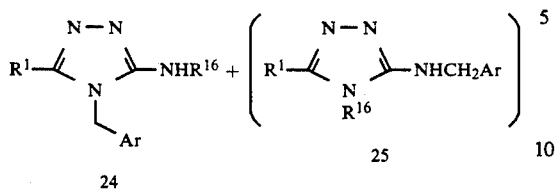
24

Aminotriazoles of formula 24, where B is a single bond, can be prepared as shown in Scheme I-8. An analogous route has been reported by E. Akerblom, *Acta Chem. Scand.*, 19, 1135 (1965). Reaction of the isothiocyanate 4 with an appropriate amine gives the thiourea 21, which is alkylated with methyl iodide to give the isothiourea hydriodide 22. the acylaminoguanidine 23, obtained by reaction of 22 with a hydrazide in the presence of base, can be thermally cyclized to 24, which is separated from the isomeric byproduct 25. Modest yields of aminotriazoles analogous to 24 have also been obtained by direct thermal reaction of intermediates analogous to 22 with a hydrazide [L. Carey, B. J. Price, J. W. Clitherow, J. Bradshaw, M. Martin-Smith, D. E. Bays, and P. Blatcher, U.S. Pat. No. 4,481,199 (1984)].

SCHEME I-9

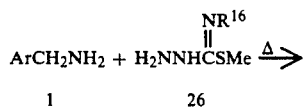

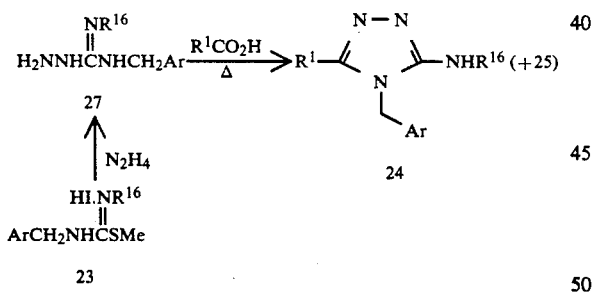

In another route is shown in Scheme I-9 following a sequence reported by L. Carey, et al., U.S. Pat. No. 4,481,199 (1984), amine 1 is heated with the S-methyl thiosemicarbazide derivative 26 to give the aminoguanidine 27. Heating 27 with an appropriate carboxylic acid provides the aminotriazole 24, which is separated from the isomer 25 if present. Similar chemistry has been reported by C. F. Kroger, G. Schoknecht, and H. Beyer, *Chem. Ber.*, 97, 396 (1964), R. G. W. Spickett and S. H. B. Wright, British Patent 1,070,243 (1967), and G. J. Durant, G. M. Smith, R. G. W. Spickett, and S. H. B. Wright, *J. Med. Chem.*, 9, 22 (1966). This last paper also describes the synthesis of aminoguanidines analogous to 27 by hydrazine treatment of isothioureas corresponding to 22 (see Scheme I-8).

SCHEME I-10

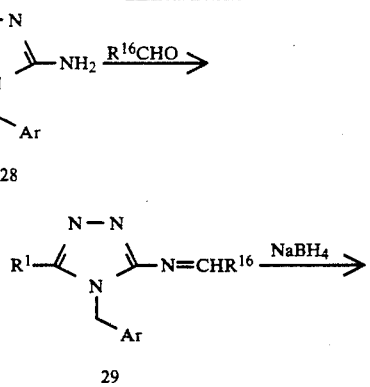

$R^{16}$ = aryl

A useful route to certain N-(arylmethyl) aminotriazoles 30 is shown in Scheme I-10. The aminotriazole 28 (equivalent to 24, R'=H), which can be prepared by Scheme I-8 or Scheme I-9 is condensed with an aromatic aldehyde to give the Schiff base 29. Reduction of 29 with a suitable reducing agent such as sodium borohydride gives 30. Related syntheses of benzylaminotriazoles have been reported by Reiter [J. Reiter, T. Somorai, P. Dvortsak, and By. Bujtas, *J. Heterocycl. Chem.*, 22, 385 (1985) and J. Reiter, L. Pongo, and P. Dvortsak, *J. Heterocycl. Chem.*, 24, 127 (1987)].

SCHEME I-11

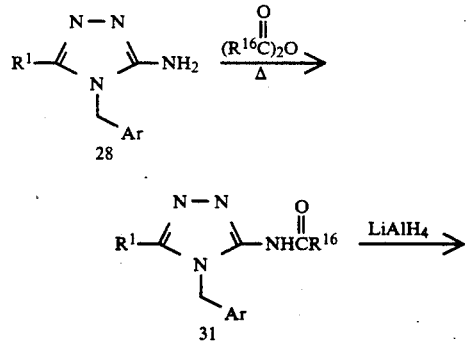

Following the methods of R. G. Harrison, W. B. Jamison, W. J. Ross, and J. C. Saunders, Australian Patent Specification 518, 316, aminotriazoles of structure 28 can be heated with an acid anhydride to give the acylaminotriazoles 31. These can be reduced with lithium aluminum hydride to give the N-substituted aminotriazoles of formula 32.

SCHEME I-12

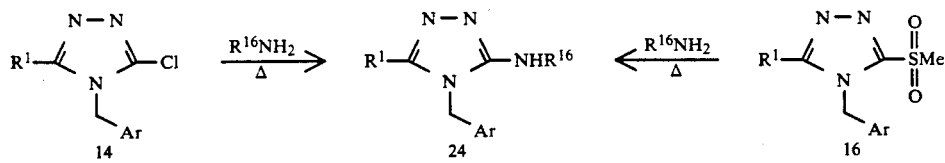

Aminotriazoles of structure 24 can also be obtained by heating a chlorotriazole 14 or a methanesulfonyltriazole 16 with an amine. Amine displacements on chlorotriazoles have been reported by H. G. O. Becker and V. Eisenschmidt, *Z. Chem.*, 8, 105, (1968) and H. Becker and K. Wehner, British Patent 1,157,256 (1969).

SCHEME I-13

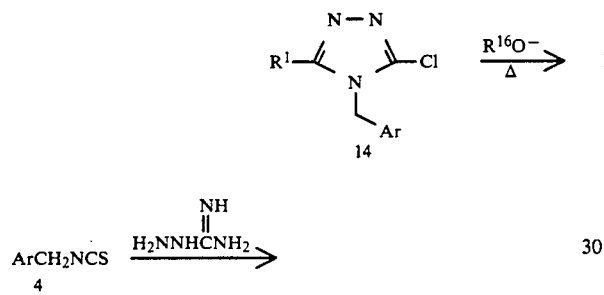

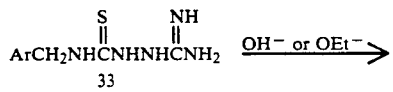

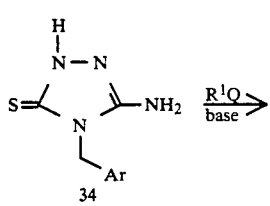

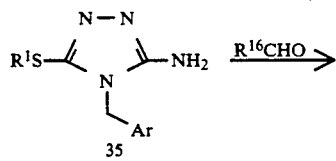

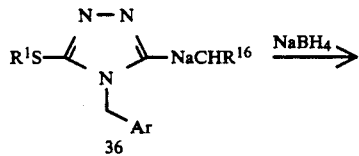

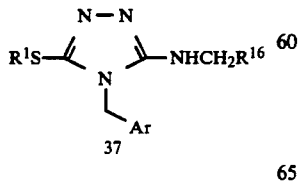

Aminomercaptotriazoles of structure 37 can be prepared as outlined in Scheme I-13, which utilizes the chemistry of L. E. Godfrey and F. Kurzer, *J. Chem. Soc.* 5137 (1961), J. Reiter, T. Somorai, P. Dvortsak, and Gy. Bujtas, *J. Heterocycl. Chem.*, 22, 385 (1985), and J. Reiter, L. Pongo, and P. Dvortsak, *J. Heterocyclic Chem.*, 24, 127 (1987). Reaction of the isothiocyanate 4 with aminoguanidine gives 33, which can be cyclized in the presence of base to the aminotriazolinethione 34. Alkylation of 34 in the presence of base yields the 5-substituted derivative 35. Further transformations to the Schiff base 36 and then to 37 are as in Scheme I-10.

SCHEME I-14

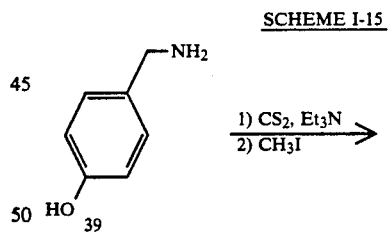

Alkoxy and aryloxytriazoles of formula 38 can be prepared by heating a chlorotriazole 14 or a methanesulfonyl triazole 16 with the appropriate alkoxide or phenoxide anion. Such a transformation has been described by E. B. Akerblom and D. E. S. Campbell, *J. Med. Chem.*, 16, 312 (1973).

SCHEME I-15

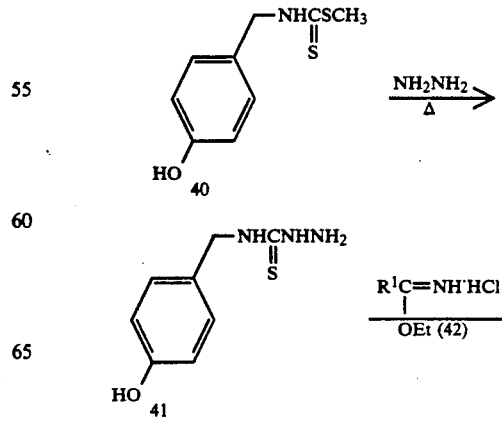

SCHEME I-15

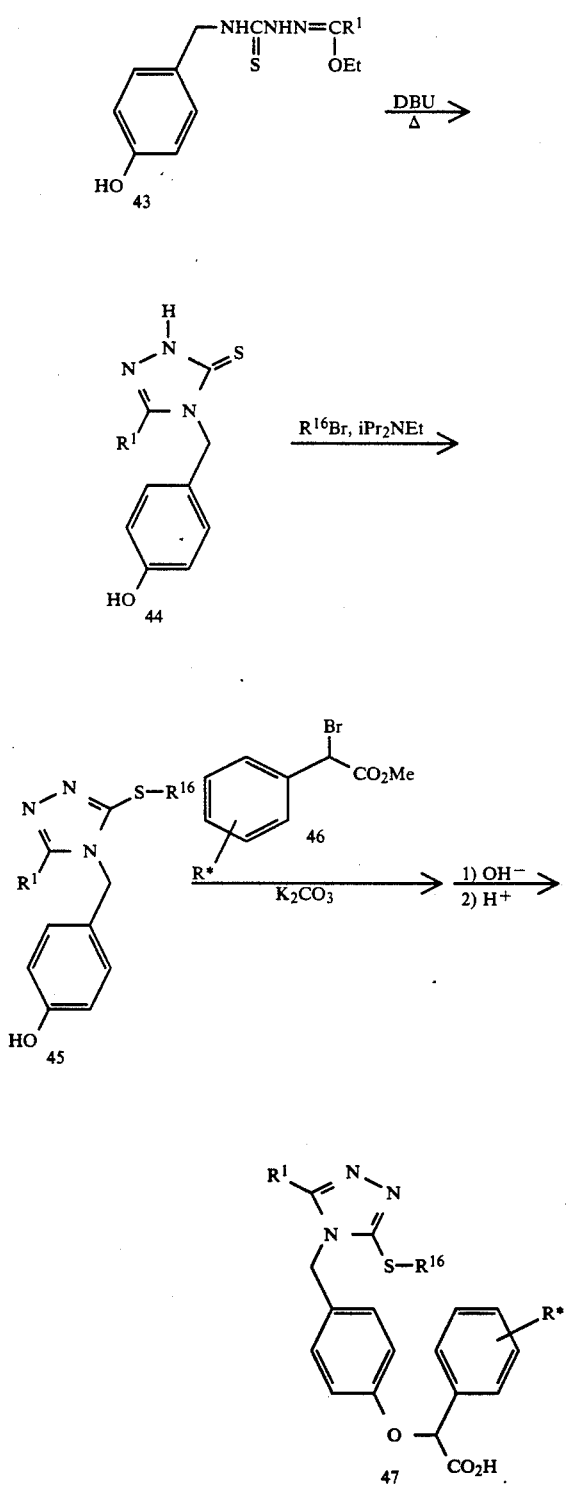

In Scheme I-15, p-hydroxybenzylamine 39 is treated first at room temperature with carbon disulfide in the presence of triethylamine and then at −10° to +20° C. with iodomethane to give the dithiocarbamate derivative 40. Upon heating with excess hydrazine in ethanol, this is transformed to the thiosemicarbazide 41. Reaction of 41 with an imidate 42 in N,N-dimethylformamide (DMF) at room temperature gives the substituted ester thiosemicarbazone 43, which cyclizes to the triazolinethione 44 upon heating with a base such as 1,8-diazabicyclo{5.4.0}undec-7-ene (DBU) in a suitable solvent such as anhydrous tetrahydrofuran (THF). Next, treatment of 44 with an alkylating agent (e.g., an alkyl or aralkyl bromide) in the presence of a tertiary amine base, preferably N,N-disopropylethylamine, in a solvent such as 2-methoxyethanol generally affords the S-alkylated derivative 45 as the primary or exclusive product. This reaction is typically carried out at 20°-100° C., depending on the reactivity of the alkylating agent. Treatment of 45 with the appropriate α-bromophenylacetic acid ester 46 in the presence of a base such as anhydrous sodium carbonate or sodium hydride in DMF or dimethyl sulfoxide (DMSO) gives an O-alkylated product which is next saponified to the acid 47. The last step is accomplished by treatment of the intermediate ester with excess sodium or potassium hydroxide in aqueous methanol followed by acidification. A similar sequence may be carried out starting with a ring-substituted 4-hydroxybenzylamine (analog of 39).

The triazolinethione 44 may be prepared by alternative methods (Scheme I-16). In one of these, the thiosemicarbazide 41 is reacted with a trimethyl orthoester, preferably in 2-methoxyethanol at reflux. In another method, 41 is treated with an acid chloride or anhydride to give the acyl derivative 48. Heating 48 with a base such as sodium ethoxide or hydroxide in an alcoholic or aqueous solvent results in ring closure to 44 (and also removes any phenolic O-acyl group that may be present as a by-product of the synthesis of 48).

It should be noted that a compound of structure 47 may also be oxidized to the corresponding sulfoxide or sulfone by treatment with hydrogen peroxide in acetic acid or with a suitable peracid as described for Scheme I-6. The oxidation may be carried out either before or after the ester hydrolysis of Scheme I-15.

As shown in Scheme I-17, the intermediate ester 49, prepared as in Scheme I-15, may be converted to a primary amide by treatment with methanolic ammonia. Dehydration of the amide with phosphorus oxychloride in the presence of triethylamine at 0° C. gives the cyano derivative 50. Reaction of 50 with trimethyltin azide in toluene at reflux, followed by removal of the trimethyltin moiety by treatment with acid and/or silica gel, yields the corresponding tetrazole 51.

SCHEME I-16

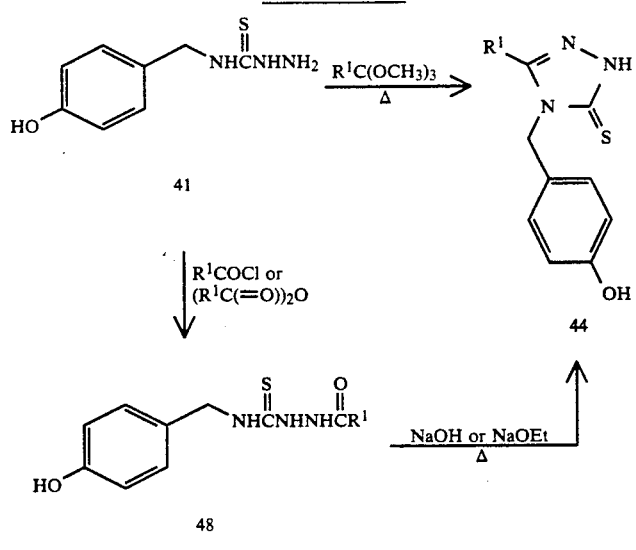

SCHEME I-17

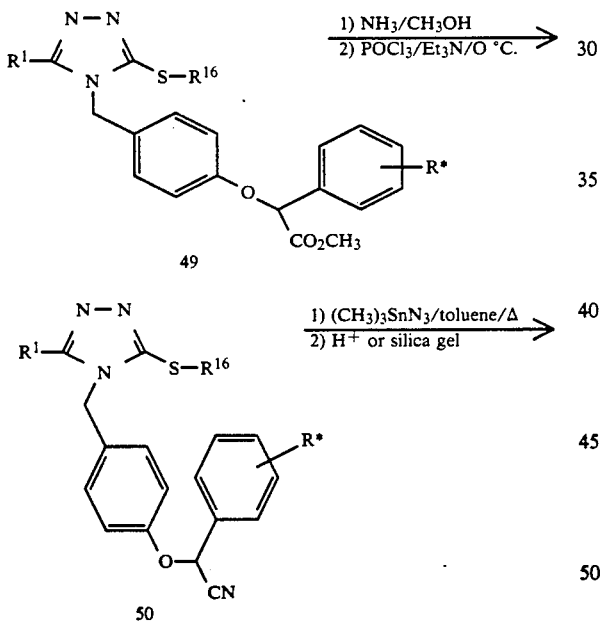

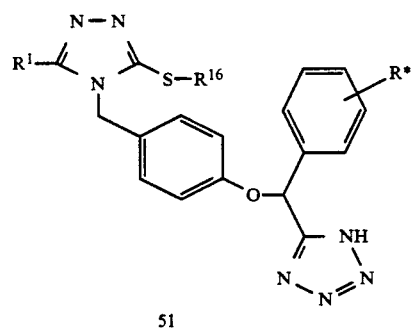

As shown in Scheme I-18, 4-(aminomethyl)benzoic acid (52) can be reduced with lithium aluminum hydride or diborane to the corresponding benzyl alcohol 53, which is converted to a triazole 54 by methods previously described. When 54 is subjected to Swern oxidation conditions, the aldehyde 55 results, and this can be used to reductively alkylate phenylalanine methyl ester in the presence of sodium cyanoborohydride. The resulting product 56 may be acylated to yield 57, which is then saponified to the free acid 58. Intermediate 56 may also be saponified, affording 59.

SCHEME I-18

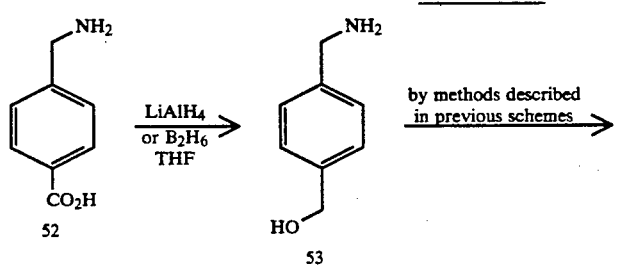

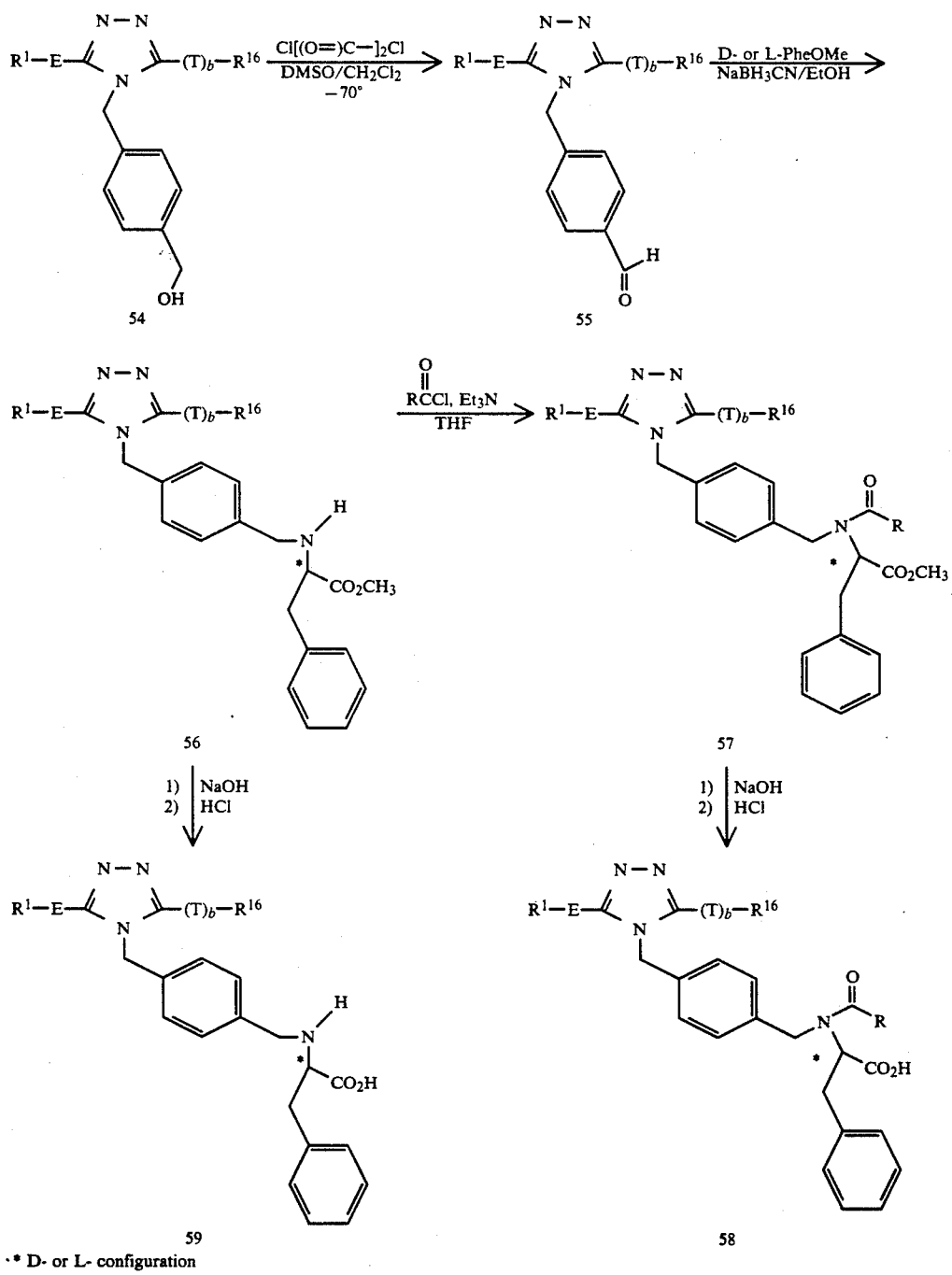
\* D- or L- configuration
SCHEME I-19
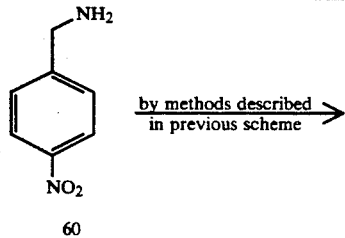
60
-continued
SCHEME I-19
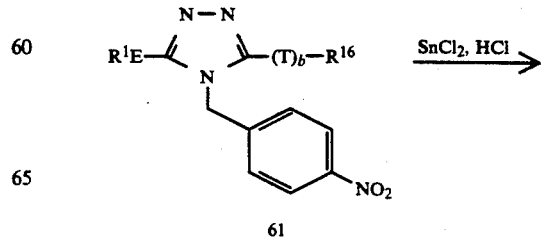

-continued
SCHEME I-19

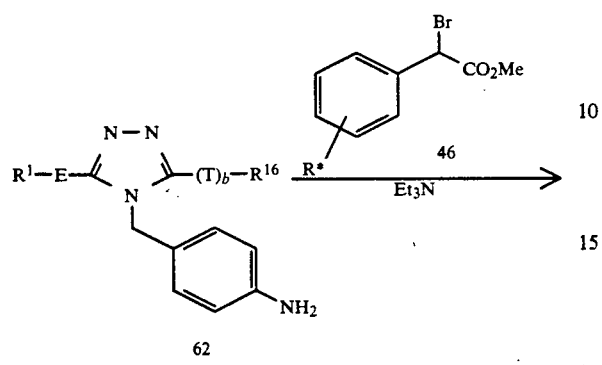
62

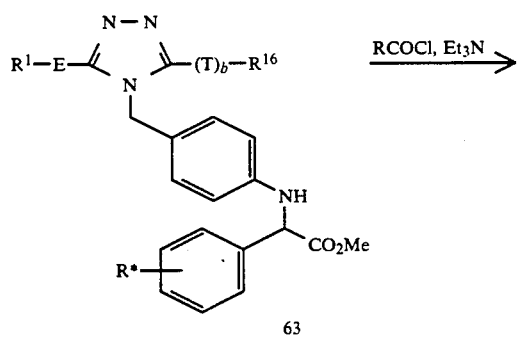
63

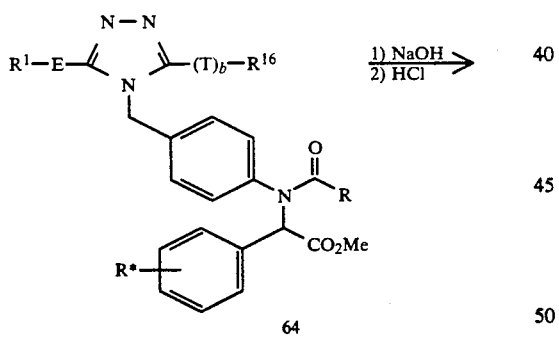
64

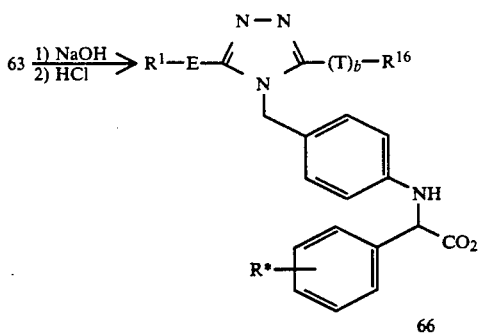
65

-continued
SCHEME I-19

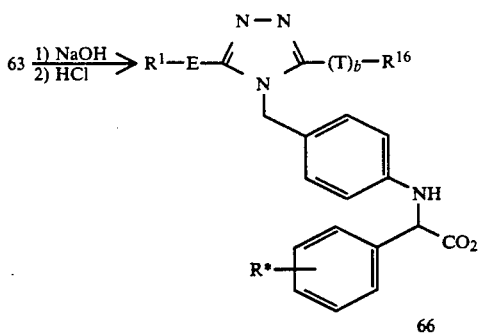
66

In Scheme I-19, 4-nitrobenzylamine (60) is transformed to the triazole 61 by previously described methods. Stannous chloride reduction of the nitro group provides the amine 62, which can be alkylated with the α-bromophenylacetic ester 46 to give 63. Acylation of 63 to give 64 and then saponification to 65 proceed under normal conditions. Intermediate 63 may also be directly saponified to give 66.

SCHEME I-20

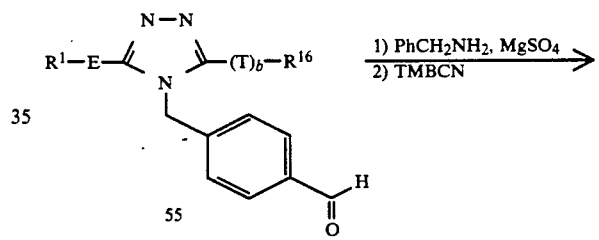
55

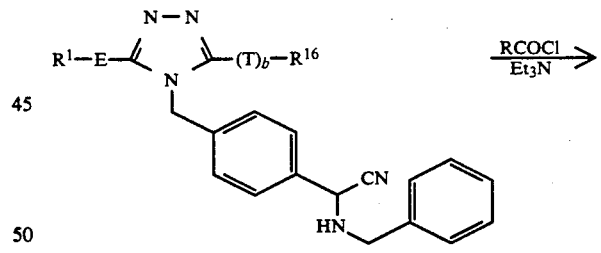
67

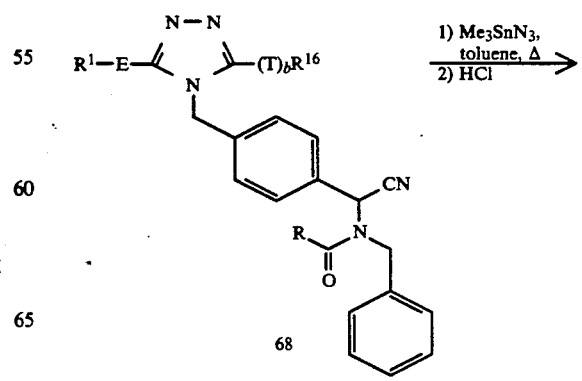
68

SCHEME I-20

-continued

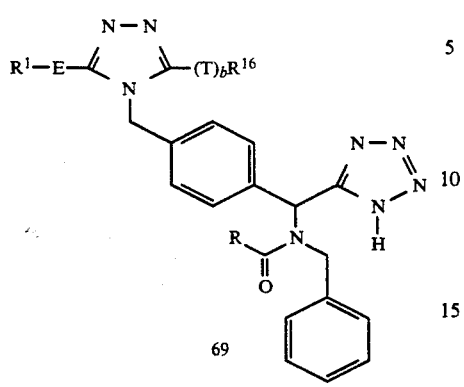

The aldehyde 55 may also be reacted with benzylamine and trimethylsilyl cyanide to give the adduct 67 (Scheme I-20). Treatment of 67 with an acid chloride in the presence of triethylamine yields the acyl derivative 68. Finally, transformation of the cyano group to tetrazole by heating with trimethyltin azide affords the target 69.

SCHEME I-21

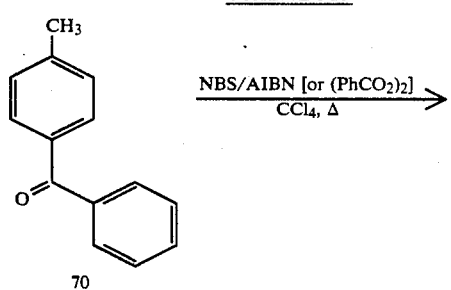

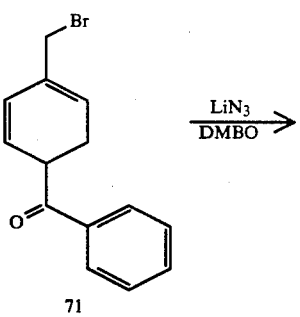

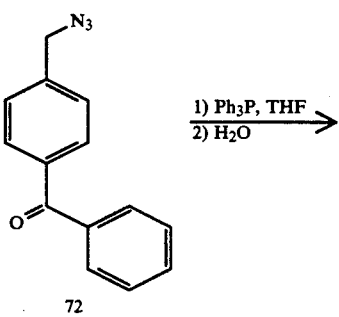

SCHEME I-21

-continued

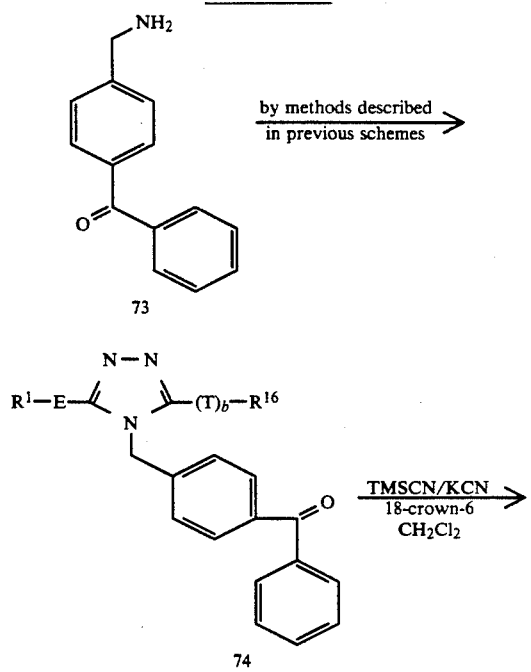

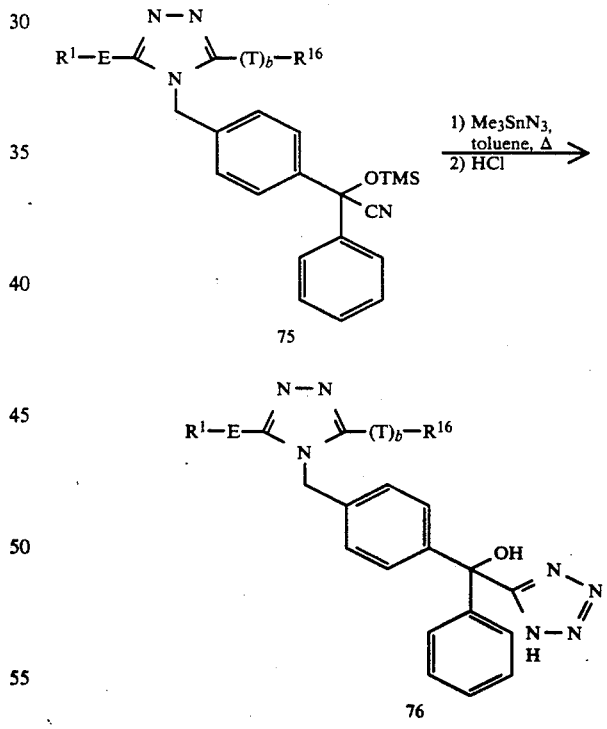

In Scheme I-21, 4-methylbenzophenone (70) is α-brominated with N-bromosuccinimide in the presence of a radical initiator such as benzoyl peroxide or azobis(isobutyronitrile)). The resulting bromo derivative 71 is converted to the azide 72, which is then reduced with triphenylphosphine to the amine 73. By previously described methods, 73 is transformed to the triazole 74. Treatment of 74 with a trimethylsilyl cyanide-potassium cyanide mixture in the presence of a crown ether yields the protected cyanohydrin 75. Upon heating 75 with excess trimethyltin azide, followed by acid treatment, the α-hydroxy tetrazole 76 is obtained.

SCHEME I-22

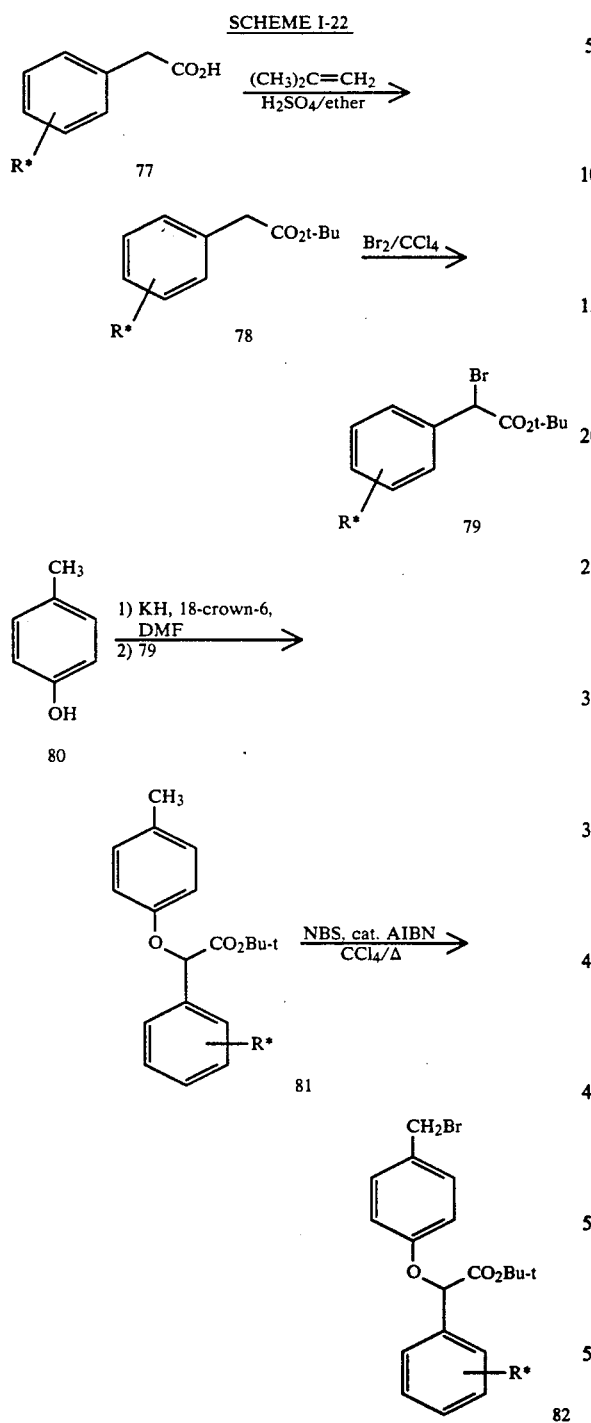

hydride or potassium t-butoxide in the presence of 18-crown-6 or with anhydrous potassium carbonate in DMF) and treated with 79 to give 81. Bromination with N-bromosuccinimide in the presence of azobis-(isobutyronitrile) (AIBN) or benzoyl peroxide provides 82, which is readily converted to the azide derivative 83 (for example, with lithium azide in DMSO). Using the methodology of O. Tsuge, S. Kanemasa, and K. Matsuda [J. Org. Chem., 49, 2688 (1984)], the azide 83 may be converted directly to the isothiocyanate 84 by reaction with triphenylphosphine and carbon disulfide. Reaction of 84, which may be used without purification, with hydrazine at room temperature in a solvent such as THF or ethanol affords the thiosemicarbazide 85. The ring closure of 85 with trimethyl orthoformate to give 86 and the subsequent alkylation of 86 to give 87 proceed as described for Schemes I-16 and I-15, respectively. Finally, the t-butyl protecting group in 87 is removed with trifluoroacetic acid at room temperature, and the free acid 88 is thus obtained.

In a variation of Scheme I-22 analogous to a sequence in Scheme I-21, intermediate 83 is reduced directly to a primary amine and then converted to a triazole by one of the previously described methods.

SCHEME I-23

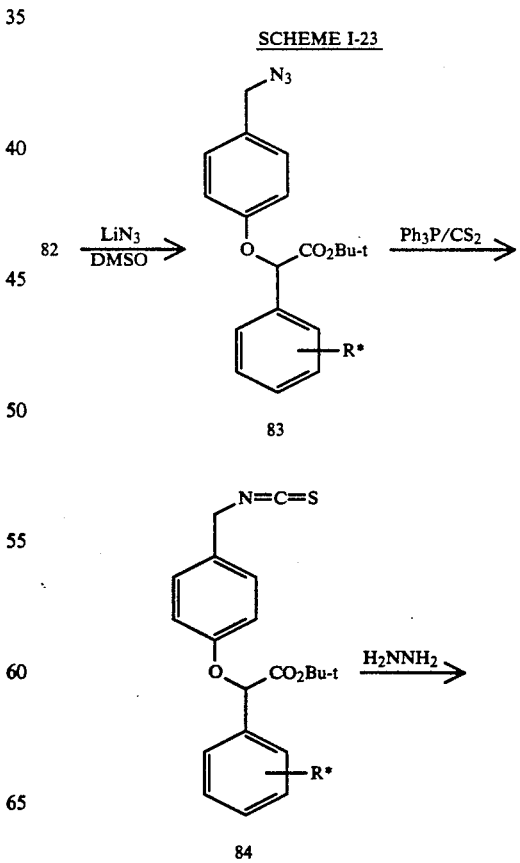

Schemes I-22 and I-23 illustrate a typical synthesis in which the 4-(α-carboxybenzyloxy)benzyl side chain (see also Schemes I-15 and I-16) is fully constructed before formation on the triazole ring. First, the appropriate phenylacetic acid 77 is converted to its t-butyl ester 78 by reaction with isobutylene in the presence of concentrated sulfuric acid, in a pressure vessel. Reaction of 78 with bromine under controlled conditions yields the α-brominated product 79. p-Cresol (80) is converted to its anion (for example, with potassium -continued
SCHEME I-23

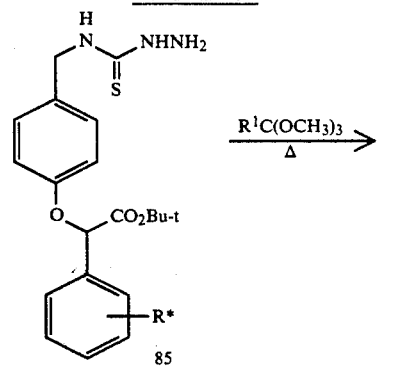
85

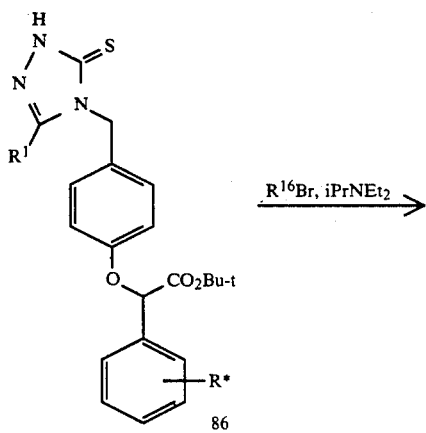
86

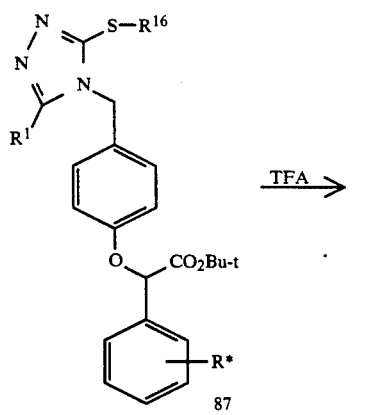
87

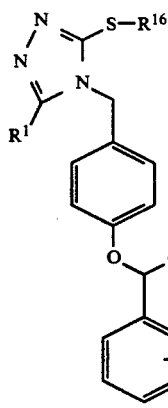
88

Compounds of formula I where Z is —CONH-SO$_2$R$^{18}$ may be prepared from the corresponding car- boxylic acid derivatives (I) as outlined in Scheme I-24. The carboxylic acid (I) can be converted into the corresponding acid chloride by treatment with refluxing thionyl chloride or preferably with oxylylchloride and a catalytic amount of dimethylformamide at low temperature [A. W. Burgstahler, L. O. Weigel, and C. G. Shaefer Synthesis, 767,(1976)]. The acid chloride then can be treated with the alkali metal salt of R$^{18}$SO$_2$NH$_2$ to form the desired acylsulfonamide 89. Alternatively, these acylsulfonamides may be also prepared from the carboxylic acids using N,N-diphenylcarbamoyl anhydride intermediates [F. J. Brown et al - European Patent Application, EP 100543; K. L. Shepard and W. Halczenko- J. Het. Chem., 16, 321 (1979)]. Preferably the carboxylic acids can be converted into acyl-imidazole intermediates, which then can be treated with an appropriate aryl or alkylsulfonamide and diazabicycloundecene (DBU) to give the desired acylsulfonamide 89 [J. T. Drummond and G. Johnson—Tetrahedron Lett.-29, 1653 (1988)].

SCHEME I-24

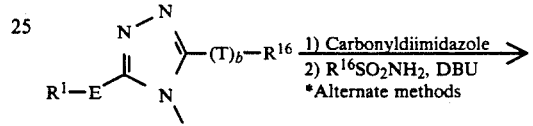

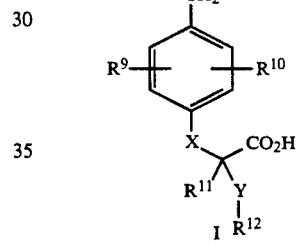
I

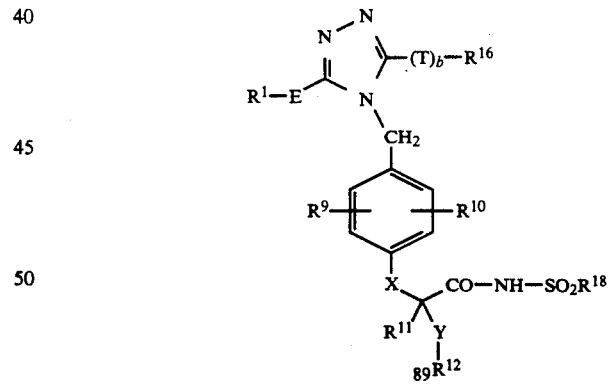
89

*Alternate Methods:
a) (i) SOCl$_2$, reflux (ii) R$^{18}$SO$_2$NH$^-$M$^+$ (where M is Na or Li)
b) (i) (COCl)$_2$, DMF, −20° C.; (ii) R$^{18}$SO$_2$NH$^-$M$^+$
c) (i) N—(N,N-Diphenylcarbamoyl)pyridinium chloride, aq. NaOH; (ii) R$^{18}$SO$_2$NH$^-$M$^+$ Intermediate ring-substituted methyl α-bromophenylacetates 46, as used in Scheme I-15, may be prepared as shown in Scheme I-25. A phenylacetic acid derivative 77, bearing one or more ring substituents, may be reacted under Hell-Volhard-Zelinsky conditions with bromine and thionyl chloride, followed by treatment with methanol to give 46. Alternatively, a substituted benzaldehyde 89 is reacted with trimethylsilyl cyanide in the presence of potassium cyanide and 18-crown-6 to give the cyanohydrin 90. Treatment of 90 with anhydrous HCl in methanol provides the α-hydroxy ester 91. Finally, reaction of 91 with carbon tetrabromide and triphenylphosphine gives the α-bromo ester 46.

SCHEME I-25

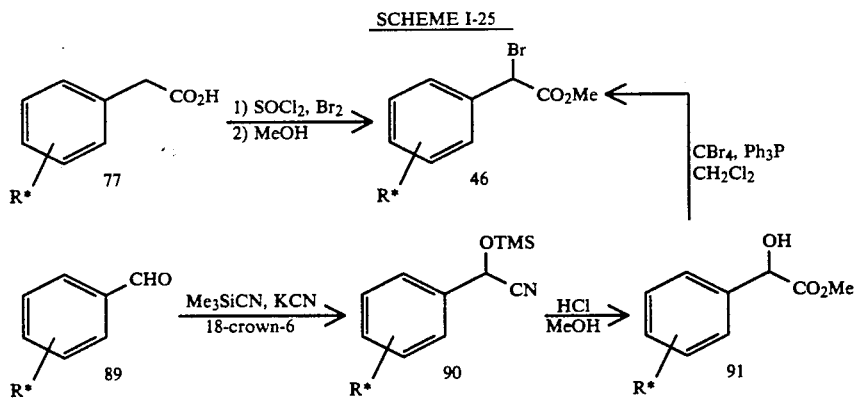

An approach to compounds of Formula I having a 3-substituent on the benzyl portion is illustrated in Scheme I-26. A 2-substituted phenol such as 2-ethylphenol (92) can be selectively carboxylated upon heating at reflux with carbon tetrachloride, 50 aqueous sodium hydroxide, and copper powder according to EP 193,853, to give the substituted 4-hydroxybenzoic acid 93. Esterification of the acid followed by silylation of the phenol and lithium aluminum hydride reduction of the ester yields the benzyl alcohol 94. This may be converted to the benzyl bromide with carbon tetrabromide and triphenylphosphine and then to the azide 95 with lithium azide in DMSO. Triphenylphosphine reduction of the azide and then disilylation with tetrabutylammonium fluoride gives the substituted 4-hydroxybenzylamine derivative 96, which may be converted by the methods of Scheme I-15 to a triazole of type 97.

SCHEME I-26

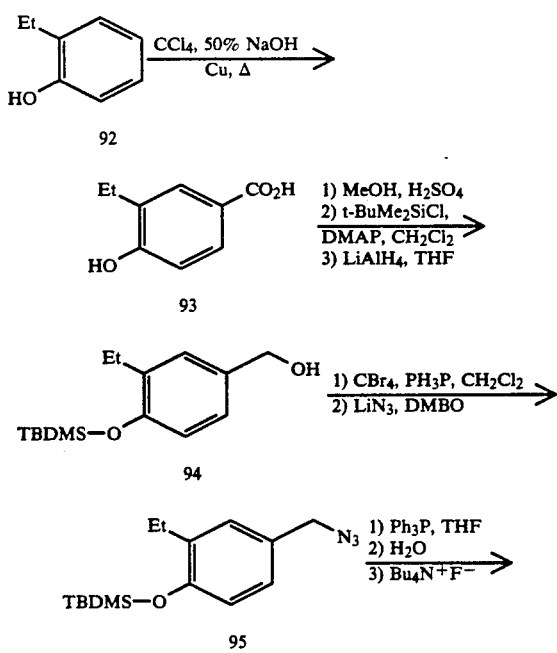

-continued
SCHEME I-26

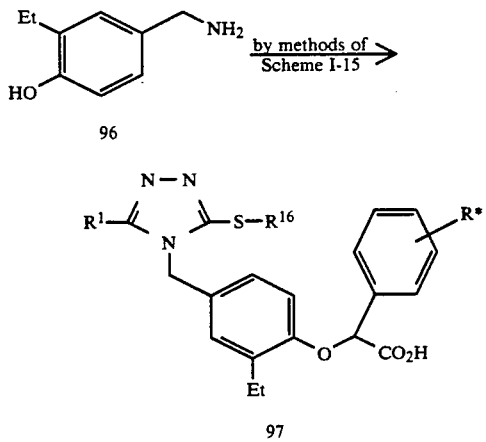

The Claisen rearrangement of allyl phenyl ethers is another useful route to intermediates for incorporation of certain alkyl or alkenyl substituents ($R^9$ or $R^{10}$) at the 3-position of the benzyl moiety in compounds of Formula I. As an example (Scheme I-27), methyl 4-hydroxybenzoate (98) is alkylated under standard conditions with allyl bromide. The product 99 undergoes Claisen rearrangement to 100 by heating at 185° C. in o-dichlorobenzene. Silylation of the phenol, followed by hydrogenation of the allyl group in the presence of a catalyst such as rhodium on carbon, gives the n-propyl derivative 101. Lithium aluminum hydride reduction of the ester then affords 102. By the methods described for Scheme I-26, this is converted to the substituted 4-hydroxybenzylamine derivative 103. By employing the methods of Scheme I-15, 103 may be transformed to a triazole of structure 104.

SCHEME I-27

-continued
SCHEME I-27

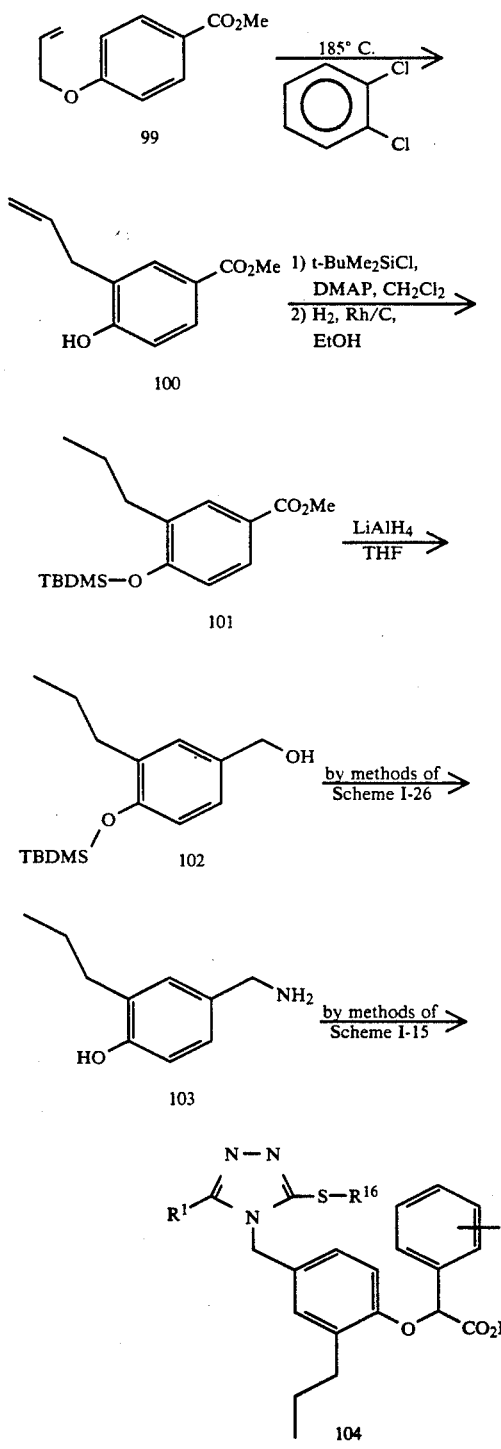

Successive Claisen rearrangements may be used to introduce two m-alkyl or alkenyl substituents ($R^9$ and $R^{10}$) into the benzyl moiety of a compound of Formula I. Thus, the allyl phenol 100 from Scheme I-27 is converted to an allyl ether and then subjected to a second Claisen rearrangement to give the diallyl phenol 105 (Scheme I-28). By the methods described for earlier schemes, 105 may be transformed to the 4-hydroxybenzylamine derivative 106 and then to a triazole of structure 107.

SCHEME I-28

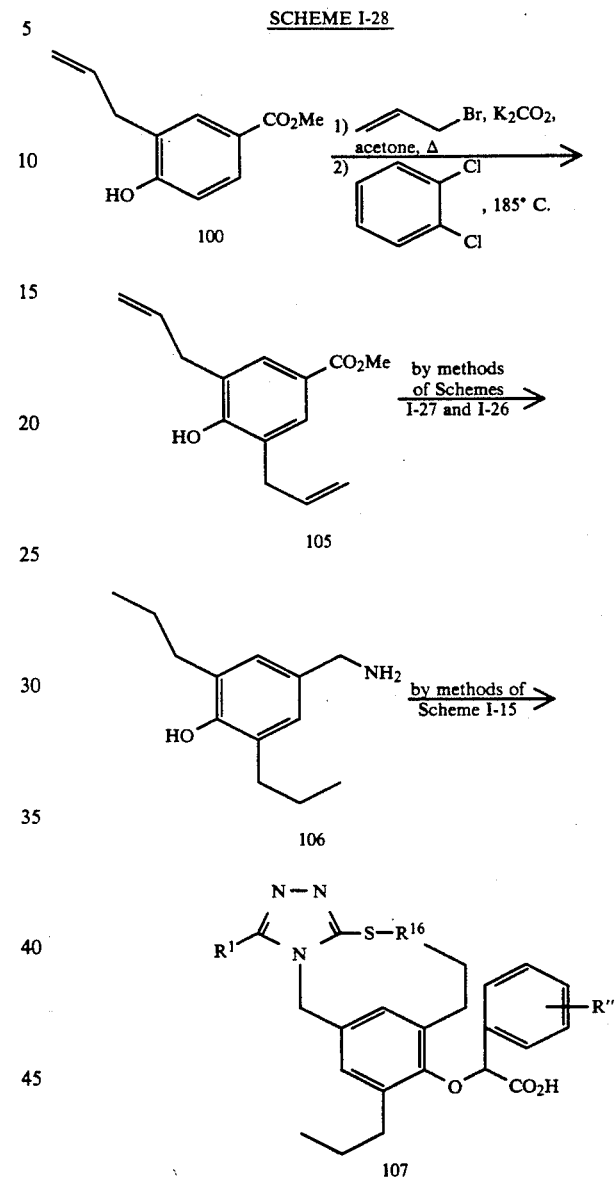

Another example of incorporation of a m-alkyl substituent ($R^9$ or $R^{10}$) on the benzyl group of a compound of Formula I is shown in Scheme I-29. This route is useful for the preparation of triazoles wherein the group $R^{16}$ is aryl or heterocyclyl and is directly attached to the triazole ring (see also Scheme I-7). Intermediate 102 (from Scheme I-27) may be desilylated with tetrabutylammonium fluoride and then alkylated with methyl α-bromophenylacetate (46) in the presence of a base such as potassium carbonate to give 108. Analogous to previously described schemes, the benzylic alcohol of 108 may be replaced by bromide and then azide. Triphenylphosphine reduction of the azido group affords the benzylamine derivative 109. Reaction of 109 with the ester acylhydrazone 19 (from Scheme I-7) in ethanol at elevated temperature gives the triazole 110. Finally, the methyl ester is saponified to yield 111.

SCHEME I-29

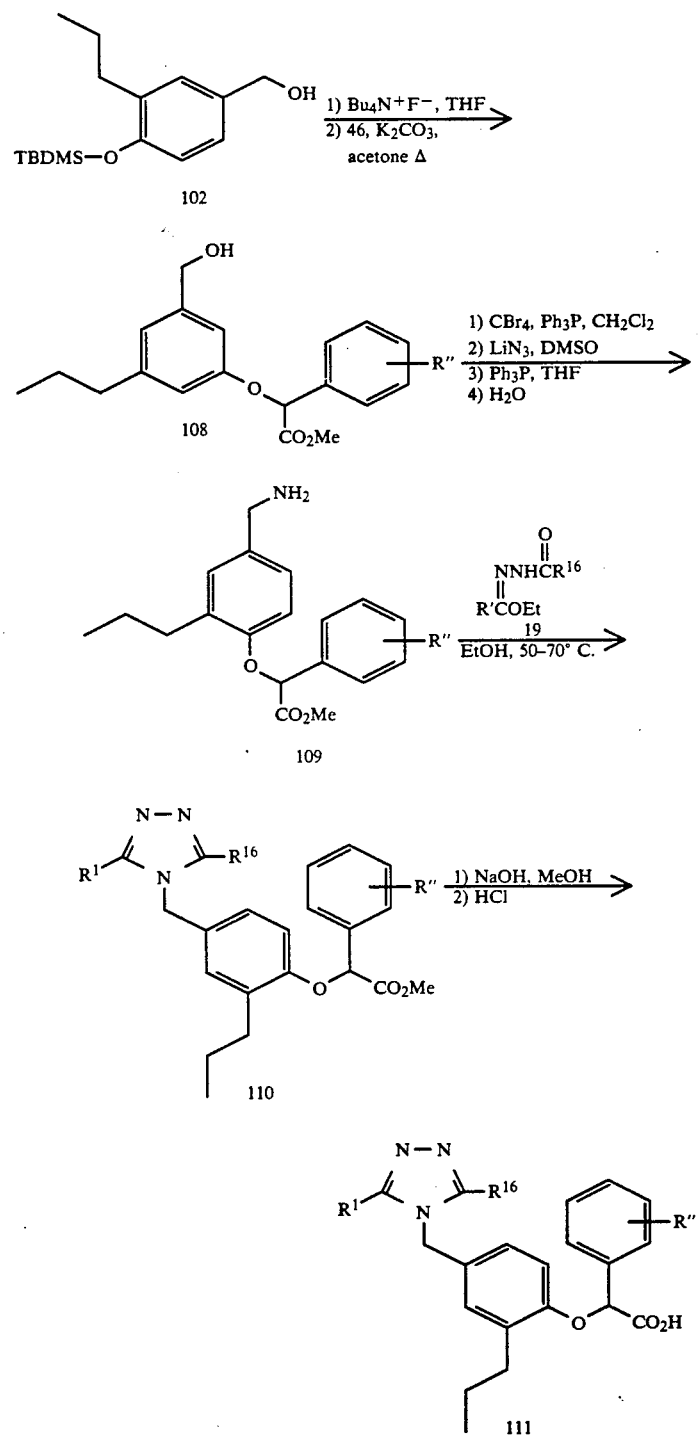

The synthesis of compounds of Formula I wherein X=NR (R=alkyl, alkenyl, and the like) is illustrated in Scheme I-30. The p-aminobenzyl triazole 62 (from Scheme I-19) can be protected as the tert-butoxycarbonyl (Boc) derivative 112. The carbamoylated NH may be deprotonated using a strong base such as sodium hydride and then alkylated with an appropriate alkyl (or allyl, etc.) halide. Subsequent removal of the Boc group with trifluoroacetic acid yields the monoalkylated aniline 113. The aniline NH may be deprotonated again with sodium hydride and alkylated with the α-bromo ester 46 to give 114. Alternatively, 114 may be prepared from the intermediate 63 (from Scheme I-19) by deprotonation with a strong base such as lithium bis(trimethylsilyl)amide followed by treatment with the alkylating agent RBr. Upon saponification of the methyl ester of 114, the target compound 115 is obtained.

SCHEME I-30

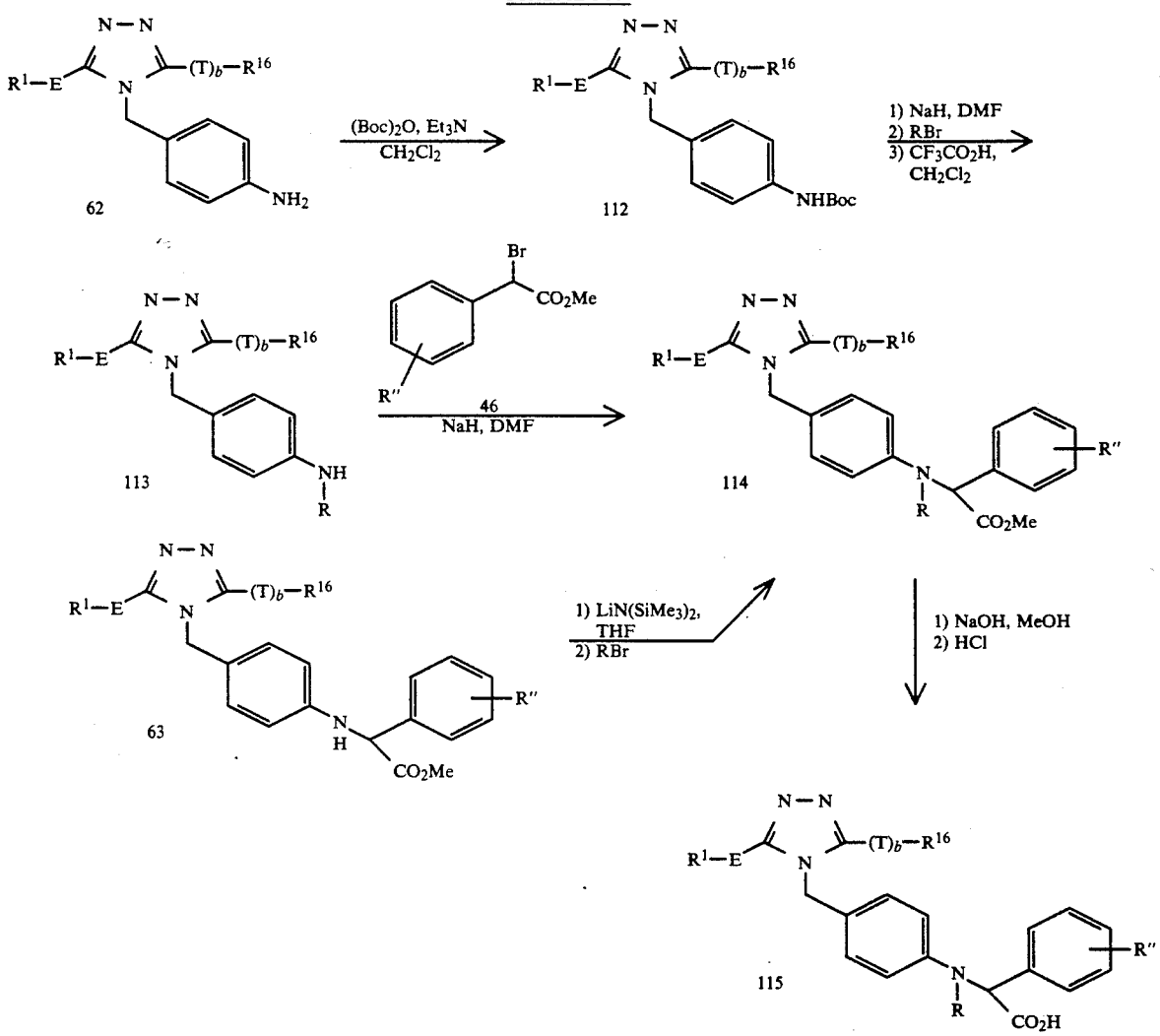

It will be appreciated by those skilled in the art that functional group transformations can be conducted on aryl and heterocyclic rings to afford desired analogs. For example, esters may be converted to amides by heating them with amines and an amide nitrogen if present in the heterocycle may be alkylated using bases such as sodium hydride in DMF with the appropriate alkyl halide. Functional group protection throughout these syntheses will be chosen to be compatible with subsequent reaction conditions. Ultimately such protecting groups will be removed to generate the desired optimally active compounds of Formula I.

The compounds of this invention form salts with various inorganic and organic acids and bases which are also within the scope of the invention. Such salts include ammonium salts, alkali metal salts like sodium and potassium salts, alkaline earth metal salts like the calcium and magnesium salts, salts with organic bases; e.g., dicyclohexylamine salts, N-methyl-D-glucamine, salts with amino acids like arginine, lysine, and the like. Also, salts with organic and inorganic acids may be prepared; e.g., HCl, HBr, $H_2SO_4$, $H_3PO_4$, methanesulfonic, toluenesulfonic, maleic, fumaric, camphorsulfonic. The non-toxic, physiologically, acceptable salts are preferred, although other salts are also useful; e.g., in isolating or purifying the product.

The salts can be formed by conventional means such as by reacting the free acid or free base forms of the product with one or more equivalents of the appropriate base or acid in a solvent or medium in which the salt is insoluble, or in a solvent such as water which is then removed in vacuo or by freeze-drying or by exchanging the cations of an existing salt for another cation on a suitable ion exchange resin.

It will be further appreciated that the compounds of general Formula I in this invention may be derivatised at functional groups to provide prodrug derivatives which are capable of conversion back to the parent compounds in vivo. The concept of prodrug administration has been extensively reviewed (e.g. A. A. Sinkula in *Annual Reports in Medicinal Chemistry*, Vol. 10, R. V. Heinzelman, Ed., Academic Press, New York London, 1975, Ch. 31, pp. 306–326), H. Ferres, *Drugs of Today*, Vol. 19, 499–538 (1983) and *J. Med. Chem.*, 18, 172 (1975). Examples of such prodrugs include the physiologically acceptable and metabolically labile ester derivatives, such as lower alkyl (e.g. methyl or ethyl esters), aryl (e.g. 5-indanyl esters), alkenyl (e.g. vinyl esters), alkoxyalkyl (e.g. methoxymethyl esters), alkylthioalkyl (e.g. methylthiomethyl esters), alkanoyloxyalkyl (e.g. pivaloyloxymethyl esters), and substituted or unsubstituted aminoethyl esters (e.g. 2-dimethylaminoethyl esters). Additionally, any physiologically acceptable equivalents of the compounds of general Formula I, similar to the metabolically labile esters, which are capable of producing the parent compounds of general Formula I in vivo, are within the scope of this invention.

Angiotension II (AII) is a powerful arterial vasoconstrictor, and it exerts its action by interacting with specific receptors present on cell membranes. The compounds described in the present invention act as competitive antagonists of AII at the receptors. In order to identify AII antagonists and determine their efficacy in vitro, the following two ligand-receptor binding assays were established.

Receptor binding assay using rabbit aortae membrane preparation

Three frozen rabbit aortae (obtained from Pel-Freeze Biologicals) were suspended in 5 mM Tris-0.25M Sucrose, pH 7.4 buffer (50 ml) homogenized, and then centrifuged. The mixture was filtered through a cheesecloth and the supernatant was centrifuged for 30 minutes at 20,000 rpm at 4° C. The pellet thus obtained was resuspended in 30 ml of 50 mM Tris-5 mM $MgCl_2$ buffer containing 0.2% Bovine Serum Albumin and 0.2 mg/ml Bacitration and the suspension was used for 100 assay tubes. Samples tested for screening were done in duplicate. To the membrane preparation (0.25 ml) there was added $^{125}I$-$Sar^1Ile^8$-angiotensin II [obtained from New England Nuclear] (10 ml; 20,000 cpm) with or without the test sample and the mixture was then diluted with ice-cold 50 mM Tris-0.9% NaCl, pH 7.4 (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist which gives 50% displacement of the total specifically bound $^{125}I$-$Sar^1Ile^8$-angiotensin II was presented as a measure of the efficacy of such compounds as AII antagonists.

Receptor assay using Bovine adrenal cortex preparation

Bovine adrenal cortex was selected as the source of AII receptor. Weighed tissue (0.1 g is needed for 100 assay tubes) was suspended in Tris.HCl (50 mM), pH 7.7 buffer and homogenized. The homogenate was centrifuged at 20,000 rpm for 15 minutes. Supernatant was discarded and pellets resuspended in buffer [$Na_2HPO_4$ (10 mM)-NaCl (120 mM)-disodium EDTA (5 mM) containing phenylmethane sulfonyl fluoride (PMSF)(0.1 mM)]. (For screening of compounds, generally duplicates of tubes are used). To the membrane preparation (0.5 ml) there was added 3H-angiotensin II (50 mM) (10 ml) with or without the test sample and the mixture was incubated at 37° C. for 1 hour. The mixture was then diluted with Tris buffer (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist which gives 50% displacement of the total specifically bound 3H-angiotensin II was presented as a measure of the efficacy of such compounds as AII antagonists.

Using the methodology described above, representative compounds of the invention were evaluated and were found to exhibit an activity of at least $IC_{50} < 50$ mM thereby demonstrating and confirming the utility of the compounds of the invention as effective AII antagonists.

The potential antihypertensive effects of the compounds described in the present invention may be evaluated using the methodology described below:

Male Charles River Sprague-Dawley rats (300–375 gm) were anesthetized with methohexital (Brevital; 50 mg/kg i.p.). The trachea was cannulated with PE 205 tubing. A stainless steel pithing rod (1.5 mm thick, 150 mm long) was inserted into the orbit of the right eye and down the spinal column. The rats were immediately placed on a Harvard Rodent Ventilator (rate—60 strokes per minute, volume—1.1 cc per 100 grams body weight). The right carotid artery was ligated, both left and right vagal nerves were cut, the left carotid artery was cannulated with PE 50 tubing for drug administration, and body temperature was maintained at 37° C. by a thermostatically controlled heating pad which received input from a rectal temperature probe. Atropine (1 mg/kg i.v.) was then administered and 15 minutes later propranolol (1 mg/kg i.v.). Thirty minutes later antagonists of formula I were administered intravenously or orally. Angiotensin II was then typically give at 5, 10, 15, 30, 45 and 60 minute intervals and every half-hour thereafter for as long as the test compound showed activity. The change in the mean arterial blood pressure was recorded for each angiotensin II challenge and the percent inhibition of the angiotensin II response was calculated.

Thus, the compounds of the invention are useful in treating hypertension. They are also of value in the management of acute and chronic congestive heart failure. These compounds may also be expected to be useful in the treatment of secondary hyperaldosteronism, primary and secondary pulmonary hyperaldosteronism, primary and secondary pulmonary hypertension, renal failure such as diabetic nephropathy, glomerulonephritis, scleroderma, glomerular sclerosis, proteinuria of primary renal disease, end stage renal disease, renal transplant therapy, and the like, renal vascular hypertension, left ventricular dysfunction, diabetic retinapathy and in the management of vascular disorders such as migraine, Raynaud's disease, luminal hyperclasia, and to minimize the atherosclerotic process. The application of the compounds of this invention for these and similar disorders will be apparent to those skilled in the art.

The compounds of this invention are also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention.

In the management of hypertension and the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Preferably, the dosage range will be about 2.5 to 250 mg. per patient per day; more preferably about 2.5 to 75 mg. per patient per day.

The compounds of this invention can also be administered in combination with other antihypertensives and/or diuretics and/or angiotensin converting enzyme inhibitors and/or calcium channel blockers. For example, the compounds of this invention can be given in combination with such compounds as amiloride, atenolol, bendroflumethiazide, chlorothalidone, chlorothiazide, clonidine, cryptenamine acetates and cryptenamine tannates, deserpidine, diazoxide, guanethidene sulfate, hydralazine hydrochloride, hydrochlorothiazide, metolazone, metoprolol tartate, methyclothiazide, methyldopa, methyldopate hydrochloride, minoxidil, pargyline hydrochloride, polythiazide, prazosin, propranolol, *rauwolfia serpentina*, rescinnamine, reserpine, sodium nitropursside, spironolactone, timolol maleate, trichlormethiazide, trimethophan camsylate, benzthiazide, quinethazone, ticrynafan, triamterene, acetazolamide, aminophylline, cyclothiazide, ethacrynic acid, furosemide, merethoxylline procaine, sodium ethacrynate, captopril, delapril hydrochloride, enalapril, enalaprilat, fosinopril sodium, lisinopril, pentopril, quinapril hydrochloride, ramapril, teprotide, zofenopril calcium, diflusinal, diltiazem, felodipine, nicardipine, nifedipine, niludipine, nimodipine, nisoldipine, nitrendipine, and the like, as well as admixtures and combinations thereof.

Typically, the individual daily dosages for these combinations can range from about one-fifth of the minimally recommended clinical dosages to the maximum recommended levels for the entities when they are given singly.

To illustrate these combinations, one of the angiotensin II antagonists of this invention effective clinically in the 2.5-250 milligrams per day range can be effectively combined at levels at the 0.5-250 milligrams per day range with the following compounds at the indicated per day dose range: hydrochlorothiazide (15-200 mg) chlorothiazide (125-2000 mg), ethacrynic acid (15-200 mg), amiloride (5-20 mg), furosemide (5-80 mg), propranolol (20-480 mg), timolol maleate (5-60 mg.), methyldopa (65-2000 mg), felodipine (5-60 mg), nifedipine (5-60 mg), and nitrendipine (5-60 mg). In addition, triple drug combinations of hydrochlorothiazide (15-200 mg) plus amiloride (5-20 mg) plus angiotensin II antagonist of this invention (3-200 mg) or hydrochlorothiazide (15-200 mg) plus timolol maleate (5-60) plus an angiotensin II antagonist of this invention (0.5-250 mg) or hydrochlorothiazide (15°200 mg) and nifedipine (5-60 mg) plus an angiotensin II antagonist of this invention (0.5-250 mg) are effective combinations to control blood pressure in hypertensive patients. Naturally, these dose ranges can be adjusted on a unit basis as necessary to permit divided daily dosage and, as noted above, the dose will vary depending on the nature and severity of the disease, weight of patient, special diets and other factors.

Typically, these combinations can be formulated into pharmaceutical compositions as discussed below.

About 1 to 100 mg. of compound or mixture of compounds of Formula I or a physiologically acceptable salt is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil. coconut oil, peanut oil, cottonseed oil, etc., or a synthetic fatty vehicle like ethyl oleate or the like. Buffers, preservatives, antioxidants and the like can be incorporated as required.

The compounds of this invention are also useful to treat elevated intraocular pressure and can be administered to patients in need of such treatment with typical pharmaceutical formulations such as tablets, capsules, injectables, as well as topical ocular formulations in the form of solutions, ointments, inserts, gels and the like. Pharmaceutical formulations prepared to treat intraocular pressure would typically contain about 0.1% to 15% by weight, and preferably 0.5% to 2.0% by weight of a compound of this invention.

Thus, the compounds of the invention are useful in treating hypertension. They are also of value in the management of acute and chronic congestive heart failure, in the treatment of secondary hyperaldosteronism, primary and secondary pulmonary hypertension, renal failure such as diabetic nephropathy, glomerulonephritis, scleroderma, and the like, renal vascular hypertension, left ventricular dysfunction, diabetic retinopathy, and in the management of vascular disorders such as migraine or Raynaud's disease. The application of the compounds of this invention for these and similar disorders will be apparent to those skilled in the art.

The useful central nervous system (CNS) activities of the compounds of this invention are demonstrated and exemplified by the ensuing assays.

COGNITIVE FUNCTION ASSAY

The efficacy of these compounds to enhance cognitive function can be demonstrated in a rat passive avoidance assay in which cholinomimetics such as physostigmine and nootropic agents are known to be active. In this assay, rats are trained to inhibit their natural tendency to enter dark areas. The test apparatus used consists of two chambers, one of which is brighly illuminated and the other is dark. Rats are placed in the illuminated chamber and the elapsed time it takes for them to enter the darkened chamber is recorded. On entering the dark chamber, they receive a brief electric shock to the feet. The test animals are pretreated with 0.2 mg/kg of the muscarinic antagonist scopolamine which disrupts learning or are treated with scopolamine and the compound which is to be tested for possible reversal of the scopolamine effect. Twenty-four hours later, the rats are returned to the illuminated chamber. Upon return to the illuminated chamber, normal young rats who have been subjected to this training and who have been treated only with control vehicle take longer to re-enter the dark chamber than test animals who have been exposed to the apparatus but who have not received a shock. Rats treated with scopolamine before training do not show this hesitation when tested 24 hours later. Efficacious test compounds can overcome the disruptive effect on learning which scopolamine produces. Typically, compounds of this invention should be efficacious in this passive avoidance assay in the dose range of from about 0.1 mg/kg to about 100 mg/kg.

ANXIOLYTIC ASSAY

The anxiolytic activity of the invention compounds can be demonstrated in a conditioned emotional response (CER) assay. Diazepam is a clinically useful anxiolytic which is active in this assay. In the CER protocol, male Sprague-Dawley rats (250-350 g) are trained to press a lever on a variable interval (VI) 60 second schedule for food reinforcement in a standard operant chamber over weekly (five days per week) training sessions. All animals then receive daily 20 minute conditioning sessions, each session partitioned into alternating 5 minute light (L) and 2 minute dark (D) periods in a fixed L1D1L2D2L3 sequence. During both periods (L or D), pressing a lever delivers food pellets on a VI 60 second schedule; in the dark (D), lever presses also elicit mild footshock (0.8 mA, 0.5 sec) on an independent shock presentation schedule of VI 20 seconds. Lever pressing is suppressed during the dark periods reflecting the formation of a conditioned emotional response (CER).

Drug testing in this paradigm is carried out under extinction conditions. During extinction, animals learn that responding for food in the dark is no longer punished by shock. Therefore, response rates gradually increase in the dark periods and animals treated with an anxiolytic drug show a more rapid increase in response rate than vehicle treated animals. Compounds of this invention should be efficacious in this test procedure in the range of from about 0.1 mg/kg to about 100 mg/kg.

DEPRESSION ASSAY

The antidepressant activity of the compounds of this invention can be demonstrated in a tail suspension test using mice. A clinically useful antidepressant which serves as a positive control in this assay is desipramine. The method is based on the observations that a mouse suspended by the tail shows alternate periods of agitation and immobility and that antidepressants modify the balance between these two forms of behavior in favor of agitation. Periods of immobility in a 5 minute test period are recorded using a keypad linked to a microcomputer which allows the experimenter to assign to each animal an identity code and to measure latency, duration and frequency of immobile periods. Compounds of this invention should be efficacious in this test procedure in the range of from about 0.1 mg/kg to about 100 mg/kg.

SCHIZOPHRENIA ASSAY

The antidopaminergic activity of the compounds of this invention can be demonstrated in an apomorphine-induced stereotypy model. A clinically useful antipsychotic drug that is used as a positive control in this assay is haloperidol. The assay method is based upon the observation that stimulation of the dopaminergic system in rats produces stereotyped motor behavior. There is a strong correlation between the effectiveness of classical neuroleptic drugs to block apomorphine-induced stereotypy and to prevent schizophrenic symptoms. Stereotyped behavior induced by apomorphine, with and without pretreatment with test compounds, is recorded using a keypad linked to a microcomputer. Compounds of the invention should be efficacious in this assay in the range of from about 0.1 mg/kg to about 100 mg/kg.

In the treatment of the clinical conditions noted above, the compounds of this invention may be utilized in compositions such as tablets, capsules or elixirs for oral administration, suppositories for rectal administration, sterile solutions or suspensions for parenteral or intramuscular administration, and the like. The compounds of this invention can be administered to patients (animals and human) in need of such treatment in dosages that will provide optimal pharmaceutical efficacy. Although the dose will vary from patient to patient depending upon the nature and severity of disease, the patient's weight, special diets then being followed by a patient, concurrent medication, and other factors which those skilled in the art will recognize, the dosage range will generally be about 5 to 6000 mg. per patient per day which can be administered in single or multiple doses. Preferably, the dosage range will be about 10 to 4000 mg. per patient per day; more preferably about 20 to 2000 mg. per patient per day.

In order to obtain maximal enhancement of cognitive function, the compounds of this invention may be combined with other cognition-enhancing agents. These include acetylcholinesterase inhibitors such as heptyl-physostigmine and tetrahydroacridine (THA; tacrine), muscarinic agonists such as oxotremorine, inhibitors of angiotensin-converting enzyme such as octylramipril, captopril, ceranapril, enalapril, lisinopril, fosinopril and zofenopril, centrally-acting calcium channel blockers such as nimodipine, and nootropic agents such as piracetam.

In order to achieve optimal anxiolytic activity, the compounds of this invention may be combined with other anxiolytic agents such as alprazolam, lorazepam, diazepam, and buspirone.

In order to achieve optimal antidepressant activity, combinations of the compounds of this invention with other antidepressants are of use. These include tricyclic antidepressants such as nortriptyline, amitryptyline and trazodone, and monoamine oxidase inhibitors such as tranylcypromine.

In order to obtain maximal antipsychotic activity, the compounds of this invention may be combined with other antipsychotic agents such as promethazine, fluphenazine and haloperidol.

The following examples illustrate the preparation of the compounds of Formula I and their incorporation into pharmaceutical compositions and as such are not to be considered as limiting the invention set forth in the claims appended thereto.

EXAMPLE 1

3-Butyl-4-[[4-[1-carboxy-1-phenylmethoxy]phenyl]methyl]-5-(4-nitrobenzylthio) -4H-1,2,4-triazole Step A: Methyl N-(4-Hydroxybenzyl)dithiocarbamate To a solution of 8.4 g (33 mmol) of 4-hydroxybenzylamine hydriodide [M. Tiffeneau, *Bull. Soc. Chim. Fr.*, 9, 819 (1911)] and 10.1 ml (7.3 g, 73 mmol) of triethylamine in 32 ml of MeOH stirred under $N_2$ at ambient temperature was added gradually a solution of 2.2 ml (2.8 g, 38 mmol) of carbon disulfide in 12 ml of MeOH. After 1 hour, the resulting solution was cooled to $-10°$ C. and treated gradually with a solution of 2 ml (4.7 g, 33 mmol) of iodomethane in 6 ml of MeOH. The solution was then stirred at room temperature for 2 hours. Next, the solution was concentrated to small volume and partitioned between ether and 0.2N HCl. The ethereal phase was washed further with 0.2N HCl followed by saturated NaCl. The ether solution was dried ($MgSO_4$), filtered, and concentrated to an oil, which gradually solidified, affording 5.98 g. (85%), mp 90°–91° C.; homogeneous by TLC in 2:1 hexane-EtOAc.

Mass Spectrum (FAB): 214 (M+1).
Analysis ($C_9H_{11}NOS_2$)
calculated: C, 50.67; H, 5.20; N, 6.57 and
found: C, 50.76; H, 5.24; N, 6.41.
$^1$NMR (CDCl$_3$, 300 MHz, ppm): δ2.64 (s,3H), 4.81 (d,2H), 6.80 (d,2H), 6.99 (br s, 1H), 7.20 (d, 2H).

Step B: 4-(4-Hydroxybenzyl)-3-thiosemicarbazide

A mixture of 5.98 g (28 mmol) of methyl N-(4-hydroxybenzyl)dithiocarbamate (product of Example 1, Step A), 27 ml (560 mmol) of hydrazine hydrate, and 72 ml of absolute EtOH was stirred at reflux for 1 hours. The solution was purged with $N_2$ and then concentrated. The residual oil was treated with 100 ml of $CH_2Cl_2$, 100 ml of ethyl acetate, and 100 ml of $H_2O$. The solid which separated was washed first with $H_2O$ and then with ether. This material was recrystallized twice from absolute EtOH to give 2.74 g (50%) of solid, mp 179°–179.5° C.; homogeneous by TLC in 19:1 $CH_2Cl_2$-MeOH.

Mass Spectrum (FAB): 198 (M+1).
Analysis {$C_8H_{11}N_3OS\cdot0.1\ C_2H_6O$ (EtOH)}
calculated: C, 48.78; H, 5.79; N, 20.82
found: C, 48.73; H, 5.52; N, 20.65.
$^1$NMR (DMSO-d$_6$, 300 MHz, ppm): δ4.47 (s,2H), 4.56 (d,2H), 6.68 (d,2H), 7.13 (d,2H), 8.09 (br s, 1H), 8.67 (s,1H), 9.25 (s,1H).

Step C: Ethyl Valerate 4-(4-Hydroxybenzyl)-3-thiosemicarbazone

A mixture of 2.67 g (13.6 mmol) of 4-(4-hydroxybenzyl)-3-thiosemicarbazide (Example 1, Step B), 3.2 g (19 mmol) of ethyl valerimidate hydrochloride [A. J. Hill nd I Rabinowitz, *J. Am. Chem. Soc.*, 48, 734 (1926)], and 30 ml of dry N,N-dimethylformamide (DMF) was stirred overnight at room temperature under $N_2$. It was then concentrated to small volume (oil pump, 50° C.) and partitioned between ethyl acetate and $H_2O$. The organic phase was washed with $H_2O$ followed by saturated NaCl. The organic solution was dried ($MgSO_4$), filtered, and concentrated to give a foam, which was chromatographed on a silica gel column (initial elution with $CH_2Cl_2$, followed by 0.5% MeOH in $CH_2Cl_2$). Evaporation of the pooled product fractions yielded 928 mg (22% of a sticky white foam; homogeneous by TLC in 19:1 $CH_2Cl_2$:MeOH; NMR indicated a mixture of syn and anti isomers.

Mass Spectrum (FAB): 310 (M+1).
Analysis ($C_{15}H_{23}N_3O_2S$):
calculated: C, 58.22; H, 7.49; N, 13.58 and
found: C, 58.11; H, 7.41; N, 13.34.
$^1$NMR (CDCl$_3$, 300 MHz, ppm): δ0.89 (q,3H), 1.2–1.4 (m,5H), 1.50 (m,2H), 2.27 (m,2H), (d,2H), 6.80 (d,2H), 7.22 (d,2H), 7.40 (br t, 1H), 7.93, 8.91 (minor and major s, total 1H).

Step D: 5-Butyl-2,4-dihydro-4-(4-hydroxybenzyl)-3H-1,2,4-triazole-3-thione

A solution of 788 mg (2.55 mmol) of ethyl valerate 4-(4-hydroxybenzyl)-3-thiosemicarbazone (Step C) and 761 μl (775 mg, 5.10 mmol) of 1,8-diazabicyclo{5.4.-0}undec-7-ene (DBU) in 8 ml of dry tetrahydrofuran (THF) was stirred at reflux under $N_2$ for 24 hours. During this time heavy precipitation occurred. The cooled mixture was filtered, and the solid was washed with THF followed by ether. The solid (DBU salt of the product) was partitioned between EtOAc and 0.2N HCl. The EtOAc phase was washed with additional 0.2N HCl and then with saturated NaCl. The EtOAc solution was dried over $MgSO_4$, filtered, and concentrated to give 229 mg (34% of a white solid, mp 156°–157° C.; homogeneous by TLC in 19:1 $CH_2Cl_2$:MeOH.

Mass Spectrum (FAB): 264 (M+1).
Analysis ($C_{13}H_{17}N_3OS$):
calculated: C, 59.29; H, 6.51; N, 15.96 and
found: C, 59.20; H, 6.54; N, 15.59
$^1$NMR (DMSO-d$_6$, 300 MHz, ppm): δ0.78 (t,3H), 1.23 (m,2H), 1.41 (m,2H), 2.49 (t,2H), 5.11 (s,2H), 6.72 (d,2H), 7.12 (d,2H), 9.45 (s,1H).

Step E: 3-Butyl-4-(4-hydroxybenzyl)-5-(4-nitrobenzylthio)-4H-1,2,4-triazole

A solution of 215 mg (0.82 mmol) of 5-butyl-2,4-dihydro-4-(4-hydroxybenzyl)-3H-1,2,4-triazole-3-thione (Step D) in 3 ml of 2-methoxyethanol was treated with 143 ml (106 mg, 0.82 mmol) of N,N-diisopropylethylamine and then with 177 mg (0.82 mmol) of 4-nitrobenzyl bromide. The solution was stirred at room temperature in a stoppered flask. Heavy precipitation began within 30 minutes. After 2.5 hours, the mixture was partitioned between 100 ml of EtOAc plus 10 ml of MeOH and 100 ml of 0.2N HCl. The EtOAc layer was washed further with 0.2N HCl and then with saturated NaCl. The organic phase was dried ($MgSO_4$), filtered, and concentrated. After drying in vacuo (oil pump) at 50° C., there was obtained 327 mg (100% of a solid, mp 132°–133° C.; homogeneous by TLC in 97:3 CHCl$_3$-iPrOH.

Mass Spectrum (FAB): 399 (M+1).
$^1$NMR (DMSO-d$_6$, 300 MHz, ppm): δ0.80 (t,3H), 1.25 (m,2H), 1.48 (m,2H), 2.62 (t,2H), 4.45 (s,2H), 4.93 (d,2H), 6.67 (d,2H), 6.83 (d,2H), 7.57 (d,2H), 8.15 (d,2H), 9.53 (br s, 1H).

Step F: 3-Butyl-4-[[4-[1-(carbomethoxy)-1-phenylmethoxy]phenyl]methyl]-5-(4-nitrobenzylthio)-4H-1,2,4-triazole A mixture of 322 mg (0.81 mmol) of 3-butyl-4-(4-hydroxybenzyl)-5-(4-nitrobenzylthio) -(4H-1,2,4-triazole (Example 1, Step E), 278 mg (1.21 mmol) of methyl α-bromophenylacetate, 168 mg (1.22 mmol) of anhydrous $K_2CO_3$, and 3 ml of dry DMF was stirred under $N_2$ at 60° C. for 24 hours. The mixture was concentrated in vacuo (oil pump, 50° C.), and the residue was partitioned between EtOAc and H$_2$O. The organic solution was dried (MgSO$_4$), filtered, and concentrated. The residual oil was chromatographed on a column of silica gel (elution with a gradient of 0.5–10% MeOH in CH$_2$Cl$_2$). TLC (97:3 CHCl$_3$-iPrOH and 98:2 CH$_2$Cl$_2$-MeOH) and NMR were used to identify the appropriate product fractions, which were combined and concentrated to give the product as a gum.

Mass Spectrum (FAB): 441 (M+1).

$^1$NMR (CDCl$_3$, 300 MHz, ppm): δ0.84 (t,3H), 1.31 (m,2H), 1.61 (m,2H), 2.55 (t,2H), 3.71 (s,3H), 4.40 (s,2H), 4.80 (s,2H), 5.57 (s,1H), 6.82 (s,4H), 7.25–7.55 (m,7H), 8.10 (d,2H).

Step G: 3-Butyl-4-[[4-[1-carboxy-1-phenylmethoxy]-phenyl]methyl]-5-(4-nitrobenzylthio) -4H-1,2,4-triazole A solution of 16 mg (0.03 mmol) of 3-butyl-4-[[4-[1-(carbomethoxy)-1-phenylmethoxy]phenyl]methyl]-5-(4-nitrobenzylthio)-4H-1,2,4-triazole (Example 1, Step F) in 240 μl of CH$_3$OH was treated with 120 μl (0.3 mmol) of 2.5N NaOH. After 15 minutes of stirring at room temperature, TLC indicated complete conversion of starting material to a lower R$_f$ product. The solution was acidified to pH 1.5 by addition of 0.2N HCl. The precipitated solid was collected on a filter, washed with H$_2$O then with ether, and dried in vacuo over P$_2$O$_5$ to give 9.5 mg (60% of the product as a solid, mp 105°–106° C. (preliminary softening); homogeneous by TLC in 90:10:1 CH$_2$Cl$_2$:CH$_3$OH:CH$_3$CO$_2$H.

Mass Spectrum (FAB): 533 (M+1).

Analysis [C$_{28}$H$_{28}$N$_4$O$_5$S.0.25H$_2$O.0.25C$_4$H$_{10}$O (ether)]:

calculated: C, 62.68; H, 5.62; N, 10.09 and
found: C, 63.05; H, 5.23; N, 9.68.

$^1$NMR (CDCl$_3$, 300 MHz, ppm): δ0.75 (t,3H), 1.20 (m,2H), 1.49 (m,2H), 2.57 (t,2H), 4.37 (s,2H), 4.81 (ABq,2H), 5.61 (s,1H), 6.86 (ABq,4H), 7.2–7.65 (m,7H), 8.07 (d,2H).

EXAMPLE 2

3-Butyl-4-[[4-[1-carboxy-1-phenylmethoxy]phenyl]methyl]-5-(4-nitrobenzylsulfinyl) -4H-1,2,4-triazole Step A: 3-Butyl-4-[[4-[1-carbomethoxy)-1-phenylmethoxy]phenyl]methyl]-5-(4-nitrobenzylsulfinyl)-4H-1,2,4-triazole A solution of 3-butyl-4-[[4-[1-(carbomethoxy)-1-phenylmethoxy]phenyl]methyl]-5-(4-nitrobenzylthio)-4H-1,2,4-triazole (from Example 1, Step F) in dry CH$_2$Cl$_2$ is treated with m-chloroperoxybenzoic acid (1 equivalent), and the resulting mixture is stirred at room temperature for about 30 minutes or until TLC indicates complete reaction. At this point the mixture is partitioned between ethyl acetate and saturated NaHCO$_3$ solution. The organic phase is washed repeatedly with saturated NaHCO$_3$, then dried over MgSO$_4$, filtered, and concentrated. The residue may be purified by chromatography on silica gel to give the title compound.

Step B: 3-Butyl-4-[[4-[1-carboxy-1-phenylmethoxy]-phenyl]methyl]-5-(4-nitrobenzylsulfinyl)-4H-1,2,4-triazole By the procedure of Example 1, Step G, 3-butyl-4-[[4-[1-(carbomethoxy)-1-phenylmethoxy]phenyl]methyl]-5-(4-nitrobenzylsulfinyl) -4H-1,2,4-triazole (from Example 2, Step A) is converted to the title compound.

EXAMPLE 3

3-Butyl-5-(4-nitrobenzylthio)-4-[[4-[1-phenyl-1-(tetrazol-5-yl)methoxy]phenyl]methyl]-4H-1,2,4-triazole Step A: 3-Butyl-4-[[4-[1-carbamoyl-1-phenylmethoxy]phenyl]methyl]-5-(4-nitrobenzylthio)-4H-1,2,4-triazole A solution of 3-butyl-4-[[4-[1-(carbomethoxy)-1-phenylmethoxy]phenyl]methyl]-5-(4-nitrobenzylthio)-4H-1,2,4-triazole (from Example 1, Step F) in methanol is saturated with gaseous ammonia at 0° and then stirred at that temperature in a stoppered vessel for about 6 hours or until TLC indicates complete reaction. The mixture is then concentrated to dryness to yield the title compound.

Step B: 3-Butyl-4-[[4-[1-cyano-1-phenylmethoxy]-phenyl]methyl]-5-(4-nitrobenzylthio)-4H-1,2,4-triazole A suspension of 3-butyl-4-[[4-[1-carbamoyl-1-phenylmethoxy]phenyl]methyl]-5-(4-nitrobenzylthio)-4H-1,2,4-triazole (from Example 3, Step A) in phosphorus oxychloride (25–30 equivalents) is stirred at 0° C. under N$_2$ as triethylamine (2.2 equivalents) is added dropwise over about 1 hours. After the addition is complete, the mixture is gradually warmed to room temperature and then heated to reflux for about 45 minutes or until TLC indicates complete reaction. The cooled mixture is concentrated in vacuo, and the residue is partitioned between ice-water and an organic solvent, such as ether, ethyl acetate, or toluene. The organic phase is washed with dilute NaOH and then with H$_2$O. The organic solution is dried over MgSO$_4$, filtered, and concentrated to give the title compound, which is used directly or may be purified by chromatography on silica gel.

Step C: 3-Butyl-5-(4-nitrobenzylthio)-4-[[4-[1-phenyl-1-(tetrazol-5-yl)methoxy]phenyl]methyl]-4H-1,2,4-triazole A mixture of 3-butyl-4-[[4-[1-cyano-1-phenylmethoxy]phenyl]methyl]-5-(4-nitrobenzylthio)-4H-1,2,4-triazole (from Example 3, Step B), trimethyltin azide (3.5 equivalents), and toluene is stirred at reflux for about 2 days. The mixture is then cooled and concentrated in vacuo. The residue is partitioned between 0.5N HCl and ethyl acetate. The ethyl acetate phase is dried (MgSO$_4$), filtered, and concentrated. The residue is taken up in methanol and stirred with silica gel (4–5 g per mmol of cyano starting material) for about 1 hour. The mixture is then evaporated in vacuo to give a dry powder, which is layered on top of a column of silica gel packed in CH$_2$Cl$_2$. Elution of the column with a gradient of methanol in CH$_2$Cl$_2$ affords the title compound.

EXAMPLE 4

3-Butyl-5-(4-nitrobenzylsulfinyl)-4-[[4-[1-phenyl-1-(tetrazol-5-yl)methoxy]phenyl]methyl]-4H-1,2,4-triazole To a stirred solution of 3-Butyl-4-[[4-[1-phenyl-1-(tetrazol-5-yl)methoxy]phenyl]methyl]-5-(4-nitrobenzylthio)-4H-1,2,4-triazole (from Example 3, Step C) in glacial acetic acid is added gradually an equal volume of 30% hydrogen peroxide (aqueous). The resulting solution is stirred at room temperature in a stoppered flask for about 15-20 hours, until TLC and/or NMR (from work-up of an aliquot) indicates complete reaction. The reaction mixture is then partitioned between ethyl acetate and dilute HCl. The ethyl acetate phase is dried (MgSO$_4$), filtered, and concentrated in vacuo. The residue is triturated with ether to give the title compound as a solid, which is collected on a filter and washed further with ether.

EXAMPLE 5

3-Butyl-4-[[4-(1-carboxy-1-phenylmethoxy)phenyl]methyl]-5-(4-chlorobenzylthio) -4H-1,2,4-triazole Step A: 3-Butyl-5-(4-chlorobenzylthio)-4-(4-hydroxybenzyl)-4H-1,2,4-triazole A solution of 500 mg (1.9 mmol) of 5-butyl-2,4-dihydro-4-(4-hydroxybenzyl)-3H-1,2,4-triazole-3-thione (from Example 1, Step D) in 4 ml of 2-methoxyethanol was treated with 330 μl (245 mg; 1.9 mmol) of N,N-diisopropylethylamine and 306 mg (1.9 mmol) of 4-chlorobenzyl chloride. The mixture was stirred at room temperature in a stoppered flask for 5 hours and then concentrated in vacuo to small volume. The residue was partitioned between 50 ml of EtOAc and 50 ml of 0.2N HCl. The organic layer was washed with an additional 50 ml of 0.2N HCl followed by 50 ml of saturated NaCl. The EtOAc solution was dried over MgSO$_4$, filtered, and concentrated. The residue was chromatographed on a column of silica gel (elution with a gradient of 1 to 3% isopropanol in CH$_2$Cl$_2$) to give 411 mg (56%) of the product as a white solid, mp 149°–150° C.; homogeneous by TLC in 97:3 CH$_2$Cl$_2$-iPrOH.

Mass Spectrum (FAB): 388 (M+1).
Analysis (C$_{20}$H$_{22}$ClN$_3$OS):
calculated: C, 61.92; H, 5.72; N, 10.83 and
found: C, 62.21; H, 5.79; N, 10.96.
$^1$H NMR (DMSO-d$_6$, 300 MHz, ppm) δ 0.81 (t, 3H), 1.26 (m, 2H), 1.48 (m, 2H), 2.57 (t, 2H), 4.30 (s, 2H), 4.89 (s, 2H), 6.68 (d, 2H), 6.78 (d, 2H), 7.33 (ABq, 4H), 9.50 (s, 1H).

Step B: 3-Butyl-4-[[4-[1-(carbomethoxy)-1-phenylmethoxy]phenyl]methyl]-5-(4-chlorobenzylthio)-4H-1,2,4-triazole A solution of 200 mg (0.52 mmol) of 3-butyl-5-(4-chlorobenzylthio)-4-(4-hydroxybenzyl) -4H-1,2,4-triazole (from Step A) in 2 ml of dry DMF was treated with 21 mg (0.52 mmol) of sodium hydride (60% in oil), and the mixture was stirred under N$_2$ at room temperature for a few minutes until H$_2$ evolution had ceased and a clear solution had resulted. To this was added 119 mg (0.52 mmol) of methyl α-bromophenylacetate, and stirring was continued under N$_2$ at room temperature for 10 minutes and then at 65° C. for 6 hours. The cooled mixture was treated with 1 ml of MeOH and then concentrated in vacuo. The residue was partitioned between 25 ml of EtOAC and 30 ml of H$_2$O. The EtOAc phase was washed with 2×25 ml of H$_2$O and then with 25 ml of saturated NaCl. The organic solution was dried over MgSO$_4$, filtered, and concentrated. Column chromatography of the residue on silica gel (gradient elution with 0.75–1.2% MeOH in CH$_2$Cl$_2$) yielded 191 mg (69%) of the title compound as a glass; homogeneous by TLC in 97:3 CH$_2$Cl$_2$-MeOH.

Mass Spectrum (FAB): 535 (M+).
Analysis (C$_{29}$H$_{30}$ClN$_3$O$_3$S)
calculated: C, 64.97; H, 5.64; N, 7.84 and
found: C, 64.80; H, 5.79; N, 7.69.
$^1$H NMR (CDCl$_3$, 300 MHz, ppm) δ 0.84 (t, 3H), 1.30 (m, 2H), 1.58 (m, 2H), 2.52 (t, 2H), 3.71 (s, 3H), 4.27 (s, 2H), 4.75 (s, 2H), 5.58 (s, 1H), 6.80 (ABq, 4H), 7.15-7.55 (m, 9H).

Step C: 3-Butyl-4-[[4-(1-carboxy-1-phenylmethoxy)phenyl]methyl]-5-(4-chlorobenzylthio) -4H-1,2,4-triazole To a solution of 165 mg (0.31 mmol) of 3-butyl-4-[[4-[1-carbomethoxy)-1-phenylmethoxy]phenyl]methyl]-5-(4-chlorobenzylthio) -4H-1,2,4-triazole (from Step B) in 2.5 ml of MeOH was added 1.23 ml (3.1 mmol) of 2.5 N NaOH. The resulting solution was stirred at room temperature in a stoppered flask for 1 hour and then adjusted to pH 2 by addition of dilute HCl. The mixture was concentrated in vacuo to give a white solid, which was washed thoroughly with dilute HCl (pH 2) and then dried. After further washing with Et$_2$O and vacuum-drying over P$_2$O$_5$, 133 mg (79%) of the title compound was obtained as a white solid, mp 66°–67° C.; homogeneous by TLC in 90:10:1 CH$_2$Cl$_2$-MeOH-AcOH.

Mass Spectrum (FAB): 522 (M+1).
Analysis (C$_{28}$H$_{28}$ClN$_3$O$_3$S•0.2 H$_2$O•0.25 C$_4$H$_{10}$O (Et$_2$O)):
calculated: C, 64.00; H, 5.72; N, 7.72 and
found: C, 63.69; H, 5.67; N, 7.77.
$^1$H NMR (DMSO-d$_6$, 300 MHz, ppm): δ 0.80 (t, 3H), 1.24 (m, 2H), 1.48 (m, 2H), 2.59 (t, 2H), 4.30 (s, 2H), 4.96 (s, 2H), 5.81 (s, 1H), 6.90 (apparent s, 4H), 7.25-7.55 (m, 9H).

EXAMPLE 6

3-Butyl-4-[[4-(1-carboxy-1-phenylmethoxy)phenyl]methyl]-5-(4-chlorobenzylsulfinyl) -4H-1,2,4-triazole To a stirred solution of 60 mg (0.11 mmol) of 3-butyl-4-[[4-[1-carboxy-1-phenylmethoxy]phenyl]methyl]-5-(4-chlorobenzylthio) -4H-1,2,4-triazole from (Example 5) in 0.75 ml of glacial acetic acid was added gradually 0.75 ml of 30% hydrogen peroxide in H$_2$O. The solution became turbid during the addition but largely clarified within a few minutes. After adding an additional 4 drops of acetic acid, the mixture was stirred at room temperature in a stoppered flask for 16 hours. It was then diluted with 50 ml of EtOAc and shaken with 50 ml of dilute HCl (pH 2.5). The aqueous phase was extracted with an additional 3 portions of EtOAc. The combined EtOAc fractions were washed once with dilute HCl (pH 2), then dried (MgSO$_4$), filtered, and concentrated. Trituration of the residue with Et$_2$O gave a gum. Upon decantation of the Et$_2$O and drying in vacuo, 31 mg (51%) of the title compound was obtained as a stiff foam, mp 76°–78° C. dec.

Mass Spectrum (FAB): 538 (M+1).
Analysis: (C$_{28}$H$_{28}$ClN$_3$O$_4$S•0.5 H$_2$O•0.1 C$_4$H$_{10}$O (Et$_2$O)):
calculated: C, 61.52; H, 5.45; N, 7.58 and
found: C, 61.56; H, 5.40; N, 7.52.
$^1$H NMR (DMSO-d$_6$, 300 MHz, ppm): δ 0.80 (m, 3H), 1.24 (m, 2H), 1.47 (m, 2H), 2.62 (m, 2H), 4.72 (ABq, 2H), 5.23, (ABq, 2H), 5.81 (s, 1H), 6.90 (m, 4H), 7.25-7.55 (m, 9H).

EXAMPLE 7

·3-Butyl-4-[[4-(1-carboxy-1-phenylmethoxy)phenyl]methyl]-5-(4-methoxybenzylthio) -4H-1,2,4-triazole Step A: 3-Butyl-4-(4-hydroxybenzyl)-5-(4-methoxybenzylthio)-4H-1,2,4-triazole Reaction of 5-butyl-2,4-dihydro-4-(4-hydroxybenzyl)-3H-1,2,4-triazole-3-thione (from Example 1, Step D) with 4-methoxybenzyl chloride according to the procedure of Example 5, Step A, gave a 70% yield of the title compound as a solid, mp 130°–131° C.; homogeneous by TLC in 95:5 CH$_2$Cl$_2$-MeOH.

Mass Spectrum (FAB): 384 (M+1)

Analysis ($C_{21}H_{25}N_3O_2S$):
calculated: C, 65.77; H, 6.57; N, 10.96 and
found: C, 65.89; H, 6.56; N, 10.77.

$^1$H NMR (DMSO-d$_6$, 300 MHz, ppm): δ 0.81 (t, 3H), 1.26 (m, 2H), 1.48 (m, 2H), 2.57 (t, 2H), 3.73 (s, 3H), 4.24 (s, 2H), 4.87 (s, 2H), 6.67, 6.79, 6.85, 7.20 (d, each 2H), 9.48 (s, 1H).

Step B: 3-Butyl-4-[[4-[1-carbomethoxy)-1-phenylmethoxy]phenyl]methyl]-5-(4-methoxybenzylthio)-4H-1,2,4-triazole The product from Step A was converted to the title compound by the procedure of Example 5, Step B. The material was obtained in 67% yield as a gum; homogeneous by TLC in 97:3 CH$_2$Cl$_2$-MeOH.

Mass Spectrum (FAB): 532 (M+1)
Analysis ($C_{30}H_{33}N_3O_4S$):
calculated: C, 67.77; H, 6.26; N, 7.91 and
found: C, 67.68; H, 6.41; N, 7.75

$^1$H NMR (CDCl$_3$, 400 MHz, ppm): δ 0.83 (t, 3H), 1.30 (m, 2H), 1.59 (m, 2H), 2.62 (t, 2H), 3.70, 3.77 (s, each 3H), 4.34 (s, 2H), 4.78 (s, 2H), 5,57 (s, 1H), 6.78 (d, 2H), 6.81 (ABq, 4H), 7.18 (d, 2H), 7.3-7.55 (m, 5H).

Step C: 3-Butyl-4-[[4-(1-carboxy-1-phenylmethoxy)-phenyl]methyl]-5-(4-methoxybenzylthio) -4H-1,2,4-triazole The product from Step B was converted to the title compound according to the procedure of Example 5, Step C. The material was obtained in 85% yield as a white solid, mp 78°-79° C.; homogeneous by TLC in 90:10:1 CH$_2$Cl$_2$-MeOH-AcOH.

Mass Spectrum (FAB): 518 (M+1)
Analysis ($C_{29}H_{31}N_3O_4S$•0.5 H$_2$O):
calculated: C, 66.13; H, 6.12; N, 7.98 and
found: C, 65.96; H, 6.10; N, 7.97.

$^1$H NMR (DMSO-d$_6$, 300 MHz, ppm): δ 0.81 (t, 3H), 1.25 (m, 2H), 1.49 (m, 2H), 2.61 (t, 2H), 3.73 (s, 3H), 4.26 (s, 2H), 4.96 (s, 2H), 5.81 (s, 1H), 6.8-7.7 (m, 13H).

EXAMPLE 8

3-Butyl-4-[[4-(1-carboxy-1-phenylmethoxy)phenyl]methyl]-5-(4-methoxybenzylsulfinyl) -4H-1,2,4-triazole By the procedure of Example 6, the title compound was prepared from 3-butyl-4-[[4-(1-carboxy-1-phenylmethoxy)phenyl]methyl]-5-(4-methoxybenzylthio)-4H-1,2,4-triazole (Example 7). The material was obtained in 65% yield as a stiff foam, mp 74°-75° C.

Mass Spectrum (FAB): 534 (M+1)
Analysis ($C_{29}H_{31}N_3O_5S$•H$_2$O•0.1 $C_4H_{10}O$ (Et$_2$O)):
calculated: C, 63.16; H, 6.13; N, 7.52 and
found: C, 63.37; H, 6.05; N, 7.42.

$^1$H NMR (DMSO-d$_6$, 300 MHz, ppm): δ 0.80 (t, 3H), 1.23 (m, 2H), 1.48 (m, 2H), 2.60 (m, 2H), 3.75 (s, 3H), 4.64 (ABq, 2H), 5.18 (ABq, 2H), 5.80 (s, 1H), 6.8-7.6 (m, 13H).

EXAMPLE 9

3-Butyl-4-[[4-[1-carboxy-1-(2-chlorophenyl)methoxy]-phenyl]methyl]-5-(4-chlorobenzylthio)-4H-1,2,4-triazole Step A: Preparation of methyl 2-bromo-2-(2-chlorophenyl)acetate A mixture of 2-chlorophenylacetic acid (5.00 g, 29.3 mmol) and thionyl chloride (2.67 mL, 1.25 eq) were heated at reflux while bromine (1.51 mL, 1.0 eq) was added from a dropping funnel over 15 minutes. The reaction mixture was heated at reflux 19.5 hours, and then cooled to room temperature. Methanol (30 mL, 25 eq) was then added slowly, as an exotherm and violent bubbling resulted. The reaction mixture was then concentrated in vacuo. The residue was partitioned between water and ether and the aqueous phase was then extracted twice with ether. The combined ether portions were washed with 5% NaHSO$_3$, dried (MgSO$_4$), filtered, and concentrated in vacuo. The residue was purified on a silica gel flash chromatography column (170×45 mm) eluted with 15% ethyl acetate/hexane to yield 2.13 g(28%) of the title compound.

$^1$H NMR (300 MHz, CDCl$_3$, ppm): δ 3.8 (s, 3H), 5.95 (s, 1H), 7.25-7.45 (m, 3H), 7.7-7.8 (m, 1H).

Step B: 3-Butyl-4-[[4-[1-carbomethoxy)-1-(2-chlorophenyl)methoxy]phenyl]methyl]-5-(4-chlorobenzylthio)-4H-1,2,4-triazole Reaction of 3-butyl-5-(4-chlorobenzylthio)-4-(4-hydroxybenzyl)-4H-1,2,4-triazole (from Example 5, Step A) with methyl 2-bromo-2-(2-chlorophenyl)acetate, from Step A, according to the procedure of Example 5, Step B, provided a 75% yield of the title compound as a glass; homogeneous by TLC in 97:3 C$_2$Cl$_2$-MeOH.

Mass Spectrum (FAB): 570 (M+1)
Analysis ($C_{29}H_{29}Cl_2N_3O_3S$):
calculated: C, 61.05; H, 5.12; N, 7.37 and
found: C, 60.87; H, 5.33; N, 7.45.

$^1$H NMR (CDCl$_3$, 300 MHz, ppm): δ 0.84 (t, 3H), 1.29 (m, 2H), 1.58 (m, 2H), 2.51 (t, 2H), 3.74 (s, 3H), 4.27 (s, 2H), 4.75 (s, 2H), 6.09 (s, 1H), 6.81 (ABq, 4H), 7.15-7.6 (m, 8H).

Step C: 3-Butyl-4-[[4-[1-carboxy-1-(2-chlorophenyl)methoxy]phenyl]methyl]-5-(4-chlorobenzylthio)-4H-1,2,4-triazole The product from Step B was converted to the title compound according to the procedure of Example 5, Step C. The material was obtained in 85% yield as a white solid, mp 100°-102° C., homogeneous by TLC in 90:10:1 CH$_2$Cl$_2$-MeOH-AcOH.

Mass Spectrum (FAB): 556 (M+1) (high resolution FAB):
calculated: 555.1150 and
found: 555.1239

$^1$H NMR (DMSO-d$_6$, 300 MHz, ppm): δ 0.79 (t, 3H) 1.23 (m, 2H), 1.47 (m, 2H), 2.62 (t, 2H), 4.32 (s, 2H), 5.00 (s, 2H), 6.04 (s, 1H), 6.91 (m, 4H), 7.25-7.55 (m, 8H).

EXAMPLE 10

3-Butyl-4-[[4-[1-carboxy-1-(2-chlorophenyl)methoxy]-phenyl]methyl]-5-(4-chlorobenzylsulfinyl)-4H-1,2,4-triazole The title compound was prepared from 3-butyl-4-[[4-[1-carboxy-1-(2-chlorophenyl)methoxy]phenyl]methyl]-5-(4-chlorobenzylthio)-4H-1,2,4-triazole (Example 9) according to the method of Example 6. The material was obtained in 71% yield as a stiff foam, mp 89°-90° C. dec. (preliminary softening).

Mass Spectrum (FAB): 572 (M+1)
Analysis ($C_{28}H_{27}Cl_2N_3O_4S$•H$_2$O):
calculated: C, 56.95; H, 4.95; N, 7.12 and
found: C, 56.71; H, 4.91; N, 7.00

$^1$H NMR (DMSO-d$_6$, 300 MHz, ppm): δ 0.78 (m, 3H), 1.21 (m, 2H), 1.45 (m, 2H), 2.60 (m, 2H), 4.72 (ABq, 2H), 5.23 (ABq, 2H), 6.04 (s, 1H), 6.90 (m, 4H), 7.2-7.6 (m, 8H).

EXAMPLE 11

3-Butyl-4-[[4-[1-carboxy-1-(2-chlorophenyl)methoxy]-phenyl]methyl]-5-(4-methoxybbenzylthio)-4H-1,2,4-triazole Step A: 3-Butyl-4-[[4-[1-carbomethoxy-1-(2-chlorophenyl)methoxy]phenyl]methyl]-5-(4-methoxybenzylthio)-4H-1,2,4-triazole Reaction of 3-butyl-4-(4-hydroxybenzyl)-5-(4-methoxybenzylthio)-4H-1,2,4-triazole (from Example 7, Step A) with methyl 2-bromo-2-(2-chlorophenyl)acetate, as prepared in Example 9, Step A, according to the procedure of Example 5, Step B, gave a 62% yield of the title compound as a glass; homogeneous by TLC in 97:3 $CH_2Cl_2$-MeOH.

Mass Spectrum (FAB): 566 (M+1)
Analysis ($C_{30}H_{32}ClN_3O_4S \cdot 0.2 H_2O$):
calculated: C, 63.24; H, 5.73; N, 7.38
found: C, 63.08; H, 5.81; N, 7.47
$^1$H NMR (CDCl$_3$, 300 MHz, ppm): δ 0.83 (t, 3H), 1.29 (m, 2H), 1.57 (m, 2H), 2.51 (t, 2H), 3.74, 3.77 (s, each 3H), 4.25 (s, 2H), 4.72 (s, 2H), 6.08 (s, 1H), 6.77 (d, 2H), 6.81 (ABq, 4H), 7.15 (d, 2H), 7.2–7.6 (m, 4H).

Step B: 3-Butyl-4-[[4-[1-carboxy-1-(2-chlorophenyl)-methoxy]phenyl]methyl]-5-(4-methoxybenzylthio)-4-1,2,4-triazole The product from Step A was converted to the title compound by the method of Example 5, Step C. The material was obtained in 79% yield as a white solid, mp 84°–86° C.; homogeneous by TLC in 90:10:1 $CH_2Cl_2$-MeOH-AcOH.

Mass Spectrum (FAB): 552 (M+1)
Analysis ($C_{29}H_{30}ClN_3O_4S \cdot 0.5 H_2O$):
calculated: C, 62.07; H, 5.57; N, 7.49 and
found: C, 62.30; H, 5.70; N, 7.43.
$^1$H NMR (DMSO-d$_6$, 300 MHz, ppm): δ 0.79 (t, 3H), 1.24 (m, 2H), 1.47 (m, 2H), 2.60 (t, 2H), 3.73 (s, 3H), 4.25 (s, 2H), 4.95 (s, 2H), 6.04 (s, 1H), 6.8–6.95 (m, 6H), 7.20 (d, 2H), 7.40 (m, 2H), 7.53 (m, 2H).

EXAMPLE 12

3-Butyl-4-[[4-(1-carboxy-1-phenylmethoxy)-3-propyl-phenyl]methyl]-5-phenyl-4H-1,2,4-triazole Step A: Preparation of methyl 4-(2-propen-1-yloxy)-benzoate A 2 L flask was equipped with a mechanical stirrer, a reflux condenser and a stopper, then charged with 50.05 g (0.329 mol) of methyl 4-hydroxybenzoate, 960 mL of acetone, 22.50 g (1.625 mol) of anhydrous potassium carbonate, 80.5 mL (112.6 g, 0.932 mol) of allyl bromide and the mixture was stirred and refluxed for 14 hours. The mixture was cooled to room temperature, filtered and concentrated to an oil. The residual oil was purified by distillation (97° C. ⌡ 0.03 mm Hg) to afford 53.52 g (86%) of the title compound.

$^1$H NMR (300 MHz, CDCl$_3$, ppm): δ 3.84 (s, 3H), 4.56 (d, J=7 Hz, 2H), 5.28 (dd, J=3,12 Hz, 1H), 5.40 (dd, J=3,19Hz, 1H), 5.96-6.10 (m, 1H), 6.90 (d, J=10 Hz, 2H), 7.96 (d, J=10 Hz, 2H).

FAB-MS: m/e 193 (M+1).

Step B: Preparation of methyl 4-hydroxy-3-(2-propen-1-yl)benzoate

A solution of 15.05 g (78.3 mmol) of the product of Step A in 25 mL of 1,2-dichlorobenzene was magnetically stirred and refluxed (183° C.) under an argon atmosphere for 18 hours. At this point, the reaction mixture was cooled to room temperature and applied to a 6 cm diameter by 18 cm silica gel flash chromatography column and eluted with 25% ethyl acetate-hexane to separate the 1,2-dichlorobenzene, then with 40% ethyl acetate-hexane to elute the product. The product fractions were concentrated in vacuo and the residual oil was crystallized from hexane to afford 13.70 g (91%) of the title compound.

$^1$H NMR (300 HMz, CDCl$_3$, ppm): δ 3.42 (d, J=8 Hz, 2H), 3.88 (s, 3H), 5.14–5.20 (m, 2H), 5.48 (s, 1H), 5.94–6.06 (m, 1H), 6.82 (d, J=12 Hz, 1H), 7.80–7.85 (m, 2H).

FAB-MS: m/e 193 (M+1).

Step C: Preparation of methyl 4-(tert-butyldimethylsilyloxy)-3-(2-propen-1-yl)benzoate To a solution of 5.168 g (26.9 mmol) of the product of Step B in 50 mL of dichloromethane was added 4.40 mL (2.95 mmol) of triethylamine, 4.46 g (2.95 mmol) of tert-butyldimethylchlorosilane, 0.100 g of 4-dimethylaminopyridine, and the reaction mixture was stirred at room temperature for 2 hours. The mixture was then diluted with 50 mL dichloromethane, washed with 100 mL 1N hydrochloric acid, dried (MgSO$_4$), filtered and evaporated. The residual oil (7.993 g, 97%) was used in the next step without further purification.

$^1$H NMR (300 MHz, CDCl$_3$, ppm): δ 0.24 (s, 6H), 1.02 (s, 9H), 3.36 (d, J=8 Hz, 2H), 3.84 (s, 3H), 4.98–5.08 (m, 2H), 5.88–6.03 (m, 1H), 6.78 (d, J=11 Hz, 1H), 7.76–8.40 (m, 2H).

FAB-MS: m/e 307 (M+1).

Step D: Preparation of 4-(tert-butyldimethylsilyloxy)-3-(2-propen-1-yl)benzyl alcohol To a magnetically stirred solution of 8.523 g (28.0 mmol) of the product from Step C in 35 mL of anhydrous THF was added 15.0 mL of a 1.0M solution of lithium aluminum hydride in THF, and the reaction mixture was stirred under a nitrogen atmosphere for 2 hours. At this point, the reaction was quenched by cautious addition of 10 mL water, the resulting precipitate was dissolved by addition of 1.0N hydrochloric acid and the product was extracted into ethyl acetate. The organic layer was separated, dried (MgSO$_4$), filtered and evaporated in vacuo to afford 7.258 g (93%) of the title compound.

$^1$H NMR (300 MHz, CDCl$_3$, ppm): δ 0.20 (s, 6H), 1.00 (s, 9H), 3.34 (d, J=8 Hz, 2H), 3.84 (s, 1H), 4.57 (s, 2H), 4.97–5.07 (m, 2H), 5.88–6.03 (m, 1H), 6.86 (d, J=10 Hz, 1H), 7.05–7.14 (m, 2H).

FAB-MS: m/e 279, 261 (M+1).

Step E: Preparation of 4-hydroxy-3-(2-propen-1-yl)benzyl alcohol

To a solution of approximately 7.26 g (2.6 mmol) of crude 4-tert-butyldimethylsilyloxy-3-(2-propen-1-yl)benzyl alcohol, from Step D, dissolved in 50 mL of anhydrous THF was added 26 mL (2.6 mmol) of tetra-n-butylammonium fluoride and the reaction mixture was stirred at room temperature for 16 hours. The mixture was then evaporated in vacuo and the residual oil was purified on a silica gel flash chromatography column eluted with 5% methanol/chloroform to afford 3.386 g (79%) of the title compound as a colorless oil.

$^1$H NMR (300 MHz, CDCl$_3$, ppm): δ 2.12 (br, s, 1H), 3.35 (d, J=8 Hz, 2H), 4.54 (s, 3H), 5.05–5.15 (m, 2H), 5.90 (br s, 1H), 5.90–6.05 (m, 1H), 6.70 (d, J=10 Hz, 1H), 7.02-7.10 (m, 2H).

FAB-MS: m/e 165 (M+1).

Step F: Preparation of 4-hydroxy-3-propylbenzyl alcohol

To a solution of 0.370 g (2.25 mmol) of the product of Step E dissolved in 25 mL of absolute ethanol was added 53 mg of a 5% rhodium on carbon catalyst and the mixture was shaken under a 40 psig pressure of hydrogen on a Parr apparatus. After 30 minutes, the reaction mixture was removed, filtered and evaporated in vacuo. The residue was purified on a silica gel flash chromatography column eluted with 35% ethyl acetate/hexane to afford the title compound.

$^1$H NMR (300 MHz, CDCl$_3$, ppm): δ 0.95 (t, J=8 Hz, 3H), 1.55-1.68 (M, 2H), 2.22 (br s, 1H), 2.57 (t, J=8 Hz, 2H), 4.56 (s, 2H), 5.93 (br s, 1), 6.66 (d, J=10 Hz, 1H), 7.00 (dd, J=2, 10 Hz, 1H), 7.08 (d, J=2 Hz, 1H).

FAB-MS: m/e 167 (M+1).

Step G: Preparation of methyl 2-(4-hydroxymethyl-2-propylphenoxy)-2-phenylacetate To a solution of 0.484 g (2.91 mmol) of the product of Step F dissolved in 12 mL of acetone were added 0.667 g (2.91 mmol) of methyl 2-bromo-2-phenylacetate, 0.804 g (5.82 mmol) of anhydrous K$_2$CO$_3$ and the mixture was stirred and heated at reflux for 5 hours. The mixture was then cooled, filtered and evaporated in vacuo. The residual oil was purified on a silica gel flash chromatography column eluted with 30% ethyl acetate/hexane to afford 0.756 g (83%) of the title compound.

$^1$H NMR (300 MHz, CDCl$_3$, ppm): δ 0.95 (t, J=8 Hz, 3H), 1.58 (br s, 1H), 1.60-1.75 (m, 2H), 2.70 (t, J=8 Hz, 2H), 3.68 (s, 3H), 4.57 (m, 2H), 5.62 (s, 1H), 6.68 (d, J=10 Hz, 1H), 7.07 (dd, J=2, 10 Hz, 1H), 7.16 (d, J=2 Hz, 1H), 7.32-7.44 (m, 3H), 7.55-7.60 (m, 2H).

FAB-MS: m/e 315 (M+1)

Step H: Methyl 2-(4-bromomethyl-2-propylphenoxy)-2-phenylacetate

A solution of 402 mg (1.28 mmol) of methyl 2-(4-hydroxymethyl-2-propylphenoxy)-2-phenylacetate, from Step G, in 4 ml of CH$_2$Cl$_2$ was treated with 510 mg (1.54 mmol) of carbon tetrabromide. The solution was stirred vigorously under N$_2$ at room temperature as 403 mg (1.54 mmole) of triphenylphosphine was added portionwise. The mixture was diluted with an additional 2 ml of CH$_2$Cl$_2$ and stirred at room temperature for 2 hours. Next, the mixture was filtered through Celite, and the filtrate was concentrated in vacuo. Flash chromatography of the residue on silica gel (gradient elution with 2.5-10% EtoAc in hexane) afforded 184 mg (38%) of the product as a gum; satisfactory purity by TLC in 98.2 CH$_2$Cl$_2$-MeOH.

Mass Spectrum (FAB): 378 (M+1)

$^1$H NMR (CDCl$_3$, 400 MHz, ppm): δ 0.96 (t, 3H), 1.68 (m, 2H), 2.69 (m, 2H), 3.70 (s, 3H), 4.45 (s, 2H), 5.63 (s, 1H), 6.65 (d, 1H), 7.1-7.6 (m, 7H).

Step I: Methyl 2-(4-azidomethyl-2-propylphenoxy)-2-phenylacetate

To a solution of 45 mg (0.12 mmol) of the product from Step H in 0.37 ml of dry DMSO was added 7.3 mg (0.15 mmol) of lithium azide. The solution was stirred at room temperature under N$_2$ for 4.5 hours. After flash chromatography on silica gel (elution with 10:1 hexane-EtOAc), 33 mg (83%) of the title compound was obtained as a gum; satisfactory purity by TLC in 4:1 hexane-EtOAc.

Mass Spectrum (FAB): 340 (M+1) $^1$H NMR (CDCl$_3$, 400 MHz, ppm): δ 0.96 (t, 3H), 1.68 (m, 2H), 2.71 (t, 2H),. 3.70 (s, 3H), 4.22 (s, 2H), 5.64 (s, 1H), 6.70 (d, 1H), 7.03 (dd, 1H), 7.10 (fine d, 1H), 7.35-7.45 (m, 3H), 7.57 (dd, 2H).

Step J: Methyl 2-(4-aminomethyl-2-propylphenoxy)-2-phenylacetate

A solution of 185 mg (0.546 mmol) of the product from step I in 1.36 ml of THF was treated portionwise with 179 mg (0.682 mmol) of triphenylphosphine. The solution was stirred at 40° C. for 2 hours. Then 19.6 μl of H$_2$O was added, and the solution was stirred at room temperature under N$_2$ overnight. The solution was concentrated in vacuo, and the residue was re-concentrated from CH$_2$Cl$_2$. Column chromatography on silica gel (elution with a gradient of 1.5-10% MeOH in CH$_2$Cl$_2$ afforded 160 mg (94%) of the product as a colorless oil; satisfactory purity by TLC in 95:5 CH$_2$Cl$_2$-MeOH.

Mass Spectrum (FAB) 314 (M+1)

$^1$H NMR (CDCl$_3$, 400 MHz, ppm): δ 0.94 (t, 3H), 1.67 (m, 2H), 2.03 (br m, 2H), 2.68 (t, 2H), 3.43 (s, 2H), 3.68 (s, 3H), 5.61 (s, 1H), 6.6-7.6 (m, 8H).

Step K: Ethyl valerate benzoylhydrazone

A solution of 2.2 g (15.9 mmol) of benzoic hydrazide in 50 ml of dry EtOH was stirred under N$_2$ at −10° C. as a solution of 2.5 g (15.1 mmol) of ethyl valerimidate hydrochloride [prepared by method of A. H. Hill and I. Rabinowitz, J. Am. Chem. Soc. 48, 734 (1926)] in 50 ml of dry EtOH was added dropwise over about 15 minutes. Stirring was continued at −10° C. for 3 hours, during which time a white precipitate separated. The cold mixture was filtered through Celite, and the filtrate was co-evaporated with CHCl$_3$ at 10° C. The residue was chromatographed twice on silica gel columns (gradient elution with 0.3-5% MeOH in CH$_2$Cl$_2$) to give 951 mg (25%) of the title compound as a cream-colored semi-solid, suitable for use without further purification (TLC in 97:3 CH$_2$Cl$_2$-MeOH). $^1$H NMR (CDCl$_3$, 400 MHz) was complex, suggesting that the product is a mixture of syn- and anti-isomers.

Mass Spectrum (FAB): 249 (M+1)

Step L: 3-Butyl-4-[[4-[1-(carbomethoxy)-1-phenylmethoxy]-3-propylphenyl]methyl]-5-phenyl-4H-1,2,4-triazole To a solution of 43.2 mg (0.175 mmol) of ethyl valerate benzoylhydrazone (from Step K) in 0.2 ml of ethanol was added a solution of 82 mg (0.262 mmol) of methyl 2-(4-aminomethyl-2-propylphenoxy)-2-phenylacetate (from Step J) in 0.2 ml of ethanol. The resulting solution was stirred under N$_2$ at 50° C. for 5.5 hours. After dilution with 0.4 ml of ethanol, the solution was then stirred at 70° C. under a condenser for 13 hours. Next, the solution was co-evaporated with CHCl$_3$. The residue was chromatographed twice in silica gel columns (gradient elution, first with 0.5-3% and then with 0.3-2% MeOH in CHCl$_2$) to give 32 mg (37%) of the title compound as a white glass; homogeneous by TLC in 9:1 CH$_2$Cl$_2$-MeOH.

Mass Spectrum (FAB): 498 (M+1)

$^1$H NMR (CDCl$_3$, 400 MHz, ppm): δ 0.86, 0.90 (t, each 3H), 1.35, 1.60, 1.72 (m, each 2H), 2.64 (m, 4H), 3.69 (s, 3H), 5.08 (s, 2H), 5.60 (s, 1H), 6.6-7.6 (m, 13H).

Step M: 3-Butyl-4-[[4-(1-carboxy-1-phenylmethoxy)-3-propylphenyl]methyl]-5-phenyl -4H-1,2,4-triazole To a solution of 32 mg (0.064 mmol) of the product from Step L in 320 μl of THF was added 320 μl (0.32 mmol) of 1N NaOH in MeOH. The solution was stirred under N$_2$ at room temperature overnight and then concentrated. The residue was dissolved in 1 ml of MeOH and acidified to pH 1.5 by addition of 1N HCl in MeOH. This was then concentrated, and the residue was leached with CHCl$_3$. The CHCl$_3$ extract was dried over anhydrous Na$_2$SO$_4$, filtered through Celite, and evaporated in vacuo. The residue was chromatographed on a silica gel column (gradient elution with 2-15% MeOH in $CH_2Cl_2$) to yield 25 mg (72%) of the title compound as a white glass; satisfactory purity by TLC in 9:1 $CH_2Cl_2$-MeOH.

Mass Spectrum (FAB): 484 (M+1)

Analysis ($C_{30}H_{33}N_3O_3 \cdot 2/3\ CH_2Cl_2$)

calculated: C, 68.20; H, 6.50; N, 7.78 and found: C, 68.31; H, 6.30; N, 7.93.

$^1$H NMR ($CD_3OD$, 400 MHz, ppm): δ 0.8–0.95 (m, 6H), 1.42, 1.59, 1.73, 2.63, 2.97 (m, each 2H), 5.40 ; (s, 2H), 5.71 (s, 1H), 6.8–7.7 (m, 13H).

What is claimed is:

1. A compound of Formula I wherein:

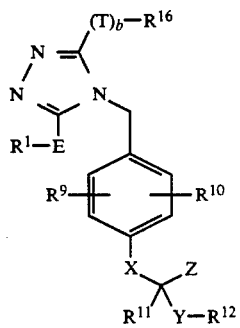

FORMULA I or a pharmaceutically acceptable salt thereof wherein:

$R^1$ is:
- (a) ($C_1$–$C_6$)-alkyl, ($C_2$–$C_6$)-alkenyl or ($C_2$–$C_6$)-alkynyl each of which is unsubstituted or substituted with one or more substituents selected from the group consisting of:
  - i) aryl, wherein aryl is defined as phenyl or naphthyl, unsubstituted or substituted with 1 or 2 substituents selected from the group consisting of:
    1) Cl, Br, I, F,
    2) ($C_1$–$C_4$)-alkyl,
    3) ($C_1$–$C_4$)-alkoxy,
    4) $NO_2$,
    5) $CF_3$,
    6) $SO_2NR^{2a}R^{2a}$,
    7) ($C_1$–$C_4$)-alkylthio,
    8) hydroxy,
    9) amino,
    10) ($C_3$–$C_7$)-cycloalkyl,
    11) ($C_3$–$C_{10}$)-alkenyl; and
  - ii) ($C_3$–$C_7$)-cycloalkyl,
  - iii) Cl, Br, I, F, or
  - iv) $COOR^2$,
  - v) —$CF_2CF_3$, or
  - vi) —$CH_2CF_3$; and
- (b) ($C_1$–$C_4$)-perfluoroalkyl, or
- (c) ($C_3$–$C_6$)-cycloalkyl, unsubstituted or substituted with one or more substituents from the group consisting of: ($C_1$–$C_4$)-alkoxy, ($C_1$–$C_4$)-alkylthio, perfluoro-($C_1$–$C_4$)-alkyl, hydroxy, or halogen (F,Cl,Br,I); and E is:
- (a) a single bond,
- (b) —S(O)$_n$(CH$_2$)$_s$—, or —O—; and n is 0 to 2; and s is 0 to 5; and $R^2$ is:
- (a) H, or
- (b) ($C_1$–$C_6$)-alkyl; and $R^{2a}$ is:
- (a) $R^2$,
- (b) $CH_2$-aryl, or
- (c) aryl; and
- (d) when $R^2$ and $R^{2a}$ are alkyl substituents on the same nitrogen then can be joined to form a ring; and wherein there is more than one $R^{2a}$ group in the definition of a structure of Formula I they may be the same or different; and $R^9$ and $R^{10}$ are independently:
- (a) H,
- (b) ($C_1$–$C_6$)-alkyl, unsubstituted or substituted with ($C_3$–$C_7$)-cycloalkyl,
- (c) ($C_2$–$C_6$)-alkenyl,
- (d) ($C_2$–$C_6$)-alkynyl,
- (e) Cl, Br, F, I,
- (f) ($C_1$–$C_6$)-alkoxyl,
- (g) when $R^9$ and $R^{10}$ are on adjacent carbons, they can be joined to form an phenyl ring,
- (h) ($C_1$–$C_6$)-perfluoroalkyl,
- (i) ($C_3$–$C_7$)-cycloalkyl, unsubstituted or substituted with ($C_1$–$C_6$)-alkyl,
- (j) aryl,
- (k) ($C_1$–$C_6$)-alkyl-S(O)$_n$—(CH$_2$)$_n$—,
- (l) hydroxy-($C_1$–$C_6$)-alkyl,
- (m) —$CO_2R^{2a}$,
- (n) —OH,
- (o) —$NR^2R^{21}$,
- (p) —[($C_1$–$C_6$)-alkyl]$NR^2R^{21}$,
- (q) —$NO_2$,
- (r) —(CH$_2$)$_n$—$SO_2$—N($R^2$)$_2$,
- (s) —$NR^2CO$—($C_1$–$C_4$)-alkyl, or
- (t) —$CON(R^2)_2$;

X is:
- (a) —O—,
- (b) —S(O)$_n$—,
- (c) —$NR^{13}$—,
- (d) —$CH_2O$—,
- (e) —$CH_2S(O)_n$,
- (f) —$CH_2NR^{13}$—,
- (g) —$OCH_2$—,
- (h) —$NR^{13}CH_2$—,
- (i) —$S(O)_nCH_2$—,
- (j) —$CH_2$—,
- (k) —$(CH_2)_2$—,
- (l) single bond, or
- (m) —CH=, wherein Y and $R^{12}$ are absent forming a —C≡C— bridge to the carbon bearing Z and $R^{11}$; and Y is:
- (a) single bond,
- (b) —O—,
- (c) —S(O)$_n$—,
- (d) —$NR^{13}$—, or
- (e) —$CH_2$—; and except that X and Y are not defined in such a way that the carbon atom to which Z is attached also simultaneously is bonded to two heteroatoms (O, N, S, SO, $SO_2$);

$R^{11}$ and $R^{12}$ are independently:
- (a) H,
- (b) ($C_1$–$C_6$)-alkyl, unsubstituted or substituted with a substituent selected from the group consisting of:
  - (i) aryl, (ii) $(C_3-C_7)$-cycloalkyl,
(iii) $NR^2R^{21}$,
(iv) morpholin-4-yl,
(v) OH,
(vi) $CO_2R^{2a}$, or
(vii) $CON(R^2)_2$,
(c) aryl or aryl-$(C_1-C_2)$-alkyl, unsubstituted or substituted with 1 to 3 substituents selected from the group consisting of:
  (i) Cl, Br, I, F,
  (ii) $(C_1-C_6)$-alkyl,
  (iii) $[(C_1-C_5)$-alkenyl$]CH_2$—,
  (iv) $[(C_1-C_5)$-alkynyl$]CH_2$—,
  (v) $(C_1-C_6)$-alkyl-$S(O)_n$—$(CH_2)_n$—,
  (vi) —$CF_3$,
  (vii) —$CO_2R^{2a}$,
  (viii) —OH,
  (ix) —$NR^2R^{21}$,
  (x) —$NO_2$,
  (xi) —$NR^2COR^2$,
  (xii) —$CON(R^2)_2$,
  (xiii) —G—$[(C_1-C_6)$-alkyl$]$-$R^{23}$,
  (xiv) —$N[CH_2CH_2]_2Q$, or
  (xv) —$P(O)[O-(C_1-C_4)$-alkyl$]_2$,
  and can additionally be substituted with 1 or 2 substituents selected from the group consisting of: Br, Cl or F,
(d) $(C_3-C_7)$-cycloalkyl;
G is: a single bond, O, $S(O)_n$ or $NR^{23}$; and
Q is: O, $S(O)_n$ or $NR^{22}$; and
$R^{13}$ is:
(a) H,
(b) $(C_1-C_6)$-alkyl,
(c) aryl,
(d) aryl-$(C_1-C_6)$-alkyl-$(C=O)$—,
(e) $(C_1-C_6)$-alkyl—$(C=O)$—,
(f) $[(C_2-C_5)$-alkenyl$]CH_2$—,
(g) $[(C_2-C_5)$-alkynyl$]CH_2$—; or
(h) aryl—$CH_2$—; and
Z is:
(a) —$CO_2H$,
(b) —$CO_2R^{24}$,
(c) —tetrazol-5-yl,
(d) —CO—NH(tetrazol-5-yl),
(e) —$CONHSO_2$—aryl,
(f) —$CONH-SO_2$—$(C_1-C_8)$-alkyl, wherein the alkyl group is unsubstituted or substituted with a substituent chosen from the group consisting of: —OH, —SH, —$O(C_1-C_4)$-alkyl, —S—$(C_1-C_4)$-alkyl, —$CF_3$, Cl, Br, F, I, —$NO_2$, —$CO_2H$, —$CO_2$—$(C_1-C_4)$-alkyl, —$NH_2$, —$NH[(C_1-C_4)$-alkyl$]$, —$N[(C_1-C_4)$-alkyl$]_2$; and
(g) —$CONH$—$SO_2$-perfluoro-$(C_1-C_4)$-alkyl,
(h) —$CONH$—$SO_2$-heteroaryl, wherein heteroaryl is as defined below,
(i) —$CONHSO_2NR^{2a}R^{2a}$,
(j) —$SO_2NHCO$-aryl,
(k) —$SO_2NHCO$—$(C_1-C_8)$-alkyl, wherein the alkyl group is unsubstituted or substituted with a substituent chosen from the group consisting of: —OH, —SH, —$O(C_1-C_4)$-alkyl, —S—$(C_1-C_4)$-alkyl, —$CF_3$, Cl, Br, F, I, —$NO_2$, —$CO_2H$, —$CO_2$—$(C_1-C_4$-alkyl, —$NH_2$, —$NH[(C_1-C_4)$-alkyl$]$, —$N[(C_1-C_4)$-alkyl$]_2$,
(l) —$SO_2NHCO$—$(C_1-C_4)$-perfluoroalkyl,
(m) —$SO_2NHCO$-heteroaryl, or
(n) —$SO_2NHCONR^{2a}R^{2a}$; and T is —$S(O)_n$—, —O—, —$NHCH_2$—, —$NHC(=O)$—, —$C(=O)N(R^{20})$-, or —$N(R^{20})$-; and
b is 0 or 1; and
$R^{15}$ is
(a) H,
(b) $(C_1-C_6)$-alkyl,
(c) phenyl, or
(d) benzyl; and
$R^{16}$ is
(a) $(C_1-C_{10})$-alkyl;
(b) substituted $(C_1-C_{10})$-alkyl in which one or more substituent(s) is selected from
  (1) I, Br, Cl, F,
  (2) hydroxy,
  (3) $(C_1-C_{10})$-alkoxy,
  (4) $(C_1-C_5)$-alkoxycarbonyl,
  (5) $(C_1-C_5)$-acyloxy,
  (6) $(C_3-C_8)$-cycloalkyl,
  (7) aryl,
  (8) substituted aryl in which the substituents are V and W,
  (9) $(C_1-C_{10})$-alkyl—$S(O)_n$,
  (10) $(C_3-C_8)$-cycloalkyl—$S(O)_n$,
  (11) phenyl-$S(O)_n$,
  (12) substituted phenyl-$S(O)_n$ in which the substituents are V and W,
  (13) oxo,
  (14) carboxy,
  (15) $NR^2R^{2a}$,
  (16) $(C_1-C_5)$-alkylaminocarbonyl,
  (17) di$(C_1-C_5)$-alkylaminocarbonyl, or
  (18) cyano,
(c) perfluoro-$(C_1-C_4)$-alkyl,
(d) $(C_2-C_{10})$-alkenyl,
(e) $(C_2-C_{10})$-alkynyl,
(f) $(C_3-C_8)$-cycloalkyl,
(g) substituted $(C_3-C_8)$-cycloalkyl in which the substituent is selected from:
  (1) $(C_1-C_5)$-alkyl, or
  (2) $(C_1-C_5)$-alkoxy,
  (3) $(C_1-C_5)$-alkoxycarbonyl,
  (4) $(C_1-C_5)$-acyloxy,
  (5) $(C_1-C_5)$-acyl,
  (6) hydroxy,
  (7) Br, Cl, F, I,
  (8) $(C_3-C_8)$-cycloalkyl,
  (9) aryl,
  (10) substituted aryl in which the substituents are V and W,
  (11) $(C_1-C_{10})$-alkyl-$S(O)_n$,
  (12) $(C_3-C_8)$-cycloalkyl-$S(O)_n$,
  (13) phenyl-$S(O)_n$,
  (14) substituted phenyl-$S(O)_n$ in which the substituents are V and W,
  (15) oxo,
  (16) carboxy,
  (17) $NR^2R^{2a}$,
  (18) $(C_1-C_5)$-alkylaminocarbonyl,
  (19) di$(C_1-C_5)$-alkylaminocarbonyl, or
  (20) cyano,
(h) $CO_2R^{2a}$,
(i) aryl,
(j) substituted aryl in which the substituents are V and W,
(k) aryl—$(CH_2)_r$—$(M_1)_z$—$(CH_2)_r$—
(l) substituted aryl—$(CH_2)_r$—$(M_1)_z$—$(CH_2)_r$— in which the aryl group is substituted with V and W,

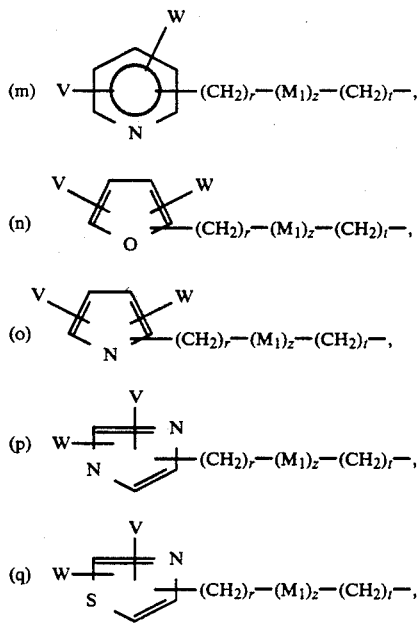

$M_1$ is O, S, —N($R^{15}$)—, or —C(O)—; and
z is 0 or 1; and
r and t are 0 to 2; and
heteroaryl is: a 5- or 6-membered aromatic ring containing from one to three heteroatoms selected from the group consisting of N, O or S; and
V and W are each independently selected from:
- (a) H,
- (b) ($C_1$-$C_5$)-alkoxy,
- (c) ($C_1$-$C_5$)-alkyl,
- (d) hydroxy,
- (e) (($C_1$-$C_5$)-alkyl)S(O)$_n$,
- (f) —CN,
- (g) —$NO_2$,
- (h) —$NR^2R^{2a}$,
- (i) (($C_1$-$C_5$)-alkyl)CO—$NR^2R^{2a}$,
- (j) —$CO_2R^{2a}$,
- (k) (($C_1$-$C_5$)—alkyl)CO—,
- (l) $CF_3$,
- (m) I, Br, Cl, F,
- (n) hydroxy—($C_1$-$C_4$)—alkyl—,
- (o) carboxy—($C_1$-$C_4$)—alkyl—,
- (p) -tetrazol-5-yl,
- (q) —NH—$SO_2CF_3$,
- (r) aryl,
- (s) —O—$CONR^2R^{2a}$,
- (t) —$NR^{2a}$—$CO_2R^{2a}$,
- (u) —$NR^{2a}$—$CONR^{2a}R^{2a}$,
- (v) —$NR^{2a}$—CON($CH_2CH_2$)$_2$Q,
- (w) —OCON($CH_2CH_2$)$_2$Q; or
- (x) —$CONR^2R^{2a}$; and $Q_1$ is O, S(O)$_n$, or $NR^{2a}$; and
$R^{18}$ is: phenyl, unsubstituted or substituted with: V and W, ($C_1$-$C_4$)-alkyl, or perfluoro-($C_1$-$C_4$)-alkyl; and
$R^{20}$ is
- (a) H,
- (b) ($C_1$-$C_6$)-alkyl,
- (c) allyl,
- (d) ($C_3$-$C_6$)-cycloalkyl,
- (e) ($C_1$-$C_4$)-acyl,
- (f) benzyl, or
- (g) phenyl; and $R^{21}$ is:
- (a) H, or
- (b) ($C_1$-$C_4$)-alkyl, is unsubstituted or substituted with:
  - i) $NH_2$,
  - ii) NH[($C_1$-$C_4$)-alkyl],
  - iii) N[($C_1$-$C_4$)-alkyl]$_2$,
  - iv) $CO_2H$,
  - v) $CO_2$($C_1$-$C_4$)-alkyl,
  - vi) OH,
  - vii) $SO_3H$, or
  - viii) $SO_2NH_2$; and $R^{22}$ is:
- (a) H,
- (b) ($C_1$-$C_4$)-alkyl,
- (c) ($C_1$-$C_4$)-alkoxyl,
- (d) aryl,
- (e) aryl-($C_1$-$C_4$)-alkyl,
- (f) $CO_2R^{2a}$,
- (g) CON($R^2$)$_2$,
- (h) $SO_2R^{2a}$,
- (i) $SO_2N(R^2)_2$,
- (j) P(O)[($C_1$-$C_4$)-alkoxyl]$_2$, or
- (k) imidazol-2-yl or imidazol-4-yl, in which the imidazole can be substituted with (C1-C4)-alkyl; and $R^{23}$ is:
- (a) OH,
- (b) $NR^2R^{21}$,
- (c) $CO_2R^{2a}$,
- (d) CON($R^2$)$_2$, or
- (e) S(O)$_n$-($C_1$-$C_4$)-alkyl; and $R^{24}$ is:
- (a) ($C_1$-$C_4$)-alkyl,
- (b) $CHR^{26}$—O—$COR^{27}$,
- (c) $CH_2CH_2$—N[($C_1$-$C_2$)—alkyl]$_2$,
- (d) $CH_2CH_2$—N[$CH_2CH_2$]$_2$O,
- (e) ($CH_2CH_2$O)$_y$—O—[($C_1$-$C_4$)-alkyl], wherein y is 1 or 2,
- (f) aryl,

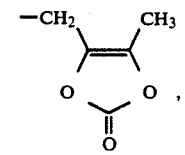
(g)

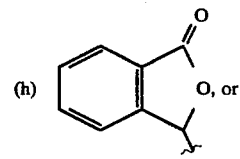
(h)

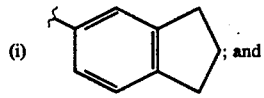
(i)

$R^{25}$ is:
- (a) H,
- (b) ($C_1$-$C_6$)-alkyl,
- (c) aryl, or
- (d) aryl-($C_1$-$C_5$)-alkyl; and $R^{26}$ and $R^{27}$ are ($C_1$-$C_6$)-alkyl or phenyl.

2. A compound which is

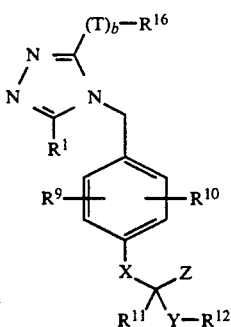

or a pharmaceutically acceptable salt thereof wherein:
$R^1$ is:
  (a) $(C_1-C_6)$-alkyl, $(C_2-C_6)$-alkenyl or $(C_2-C_6)$-alkynyl, each of which is unsubstituted with a substituent selected from the group consisting of:
    ii) $(C_3-C_7)$-cycloalkyl,
    iii) Cl, Br, I, F, or
    iv) $COOR^2$,
    v) $-CF_2CF_3$, or
    vi) $-CH_2CF_3$; and
  (b) perfluoro-$(C_1-C_4)$-alkyl, or
  (c) $(C_3-C_6)$-cycloalkyl; and
$R^2$ is: H, or $(C_1-C_6)$-alkyl; and
$R^{2a}$ is: $R^2$, benzyl, or phenyl; and when $R^2$ and $R^{2a}$ are alkyl substituents on the same nitrogen then can be joined to form a ring;
$R^9$ and $R^{10}$ are independently: H, $(C_1-C_6$-alkyl, $(C_2-C_6)$-alkenyl, $(C_2-C_6)$-alkynyl, Cl, Br, F, I, $(C_1-C_6)$-alkoxy, aryl, or $R^9$ and $R^{10}$ join to form a phenyl ring; and
X and Y are: $-CH_2-$, $-O-$, $-S-$, $-NR^{13}-$, single bond, or $-CH=$, which is double bonded to the carbon bearing Z and $R^{11}$, except that X and Y are not defined in such a way that the carbon atom to which Z is attached also simultaneously bonded to two heteroatoms (O, N, or $S(O)_n$); and
Z is:
  (a) $-CO_2H$,
  (b) $-CO_2-(C_1-C_6)$-alkyl,
  (c) -tetrazol-5-yl,
  (d) $-CO-NH$(tetrazol-5-yl)
  (e) $-CONH-SO_2-$aryl,
  (f) $-CONH-SO_2-(C_1-C_8)$-alkyl, wherein the alkyl group is unsubstituted or substituted with a substituent selected from the group consisting of: $-OH$, $-SH$, $-O(C_1-C_4)$-alkyl, $-S-(C_1-C_4)$-alkyl, $-CF_3$, Cl, Br, F, I, $-NO_2$, $-CO_2H$, $-CO_2-(C_1-C_4)$-alkyl, $-NH_2$, $-NH[(C_1-C_4)$-alkyl], $-N[(C_1-C_4)$-alkyl]$_2$; and
  (g) $-CONH-SO_2-$perfluoro-$(C_1-C_4)$-alkyl,
  (h) $-CONH-SO_2$-heteroaryl, or
  (i) $-CONHSO_2NR^2R^{2a}$; and
$R^{11}$ and $R^{12}$ are independently: H, $(C_1-C_6)$-alkyl, or aryl, wherein aryl is defined as phenyl or naphthyl, unsubstituted or substituted with 1 to 5 substituents selected from the group consisting of: Br, I. Cl, F, $(C_1-C_4)$-alkyl, $(C_2-C_4)$-alkenyl, $(C_2-C_4)$-alkynyl, $(C_1-C_4)$-alkoxyl, $NO_2$, $CF_3$, $SO_2NR^{2a}R^{2a}$, $(C_1-C_4)$-alkylthio, hydroxyl, $-NR^{2a}R^{2a}$; and
$R^{13}$ is:
  (a) H,
  (b) $(C_1-C_6)$-alkyl,
  (c) aryl, wherein aryl is unsubstituted or substituted with 1 or 2 substituents selected from the group consisting of: Br, I, Cl, F, $(C_1-C_4)$-alkyl, $(C_1-C_4)$-alkoxy, $NO_2$, $CF_3$, $SO_2NR^{2a}R^{2a}$, $(C_1-C_4)$-alkylthio, hydroxy, $-NR^{2a}R^{2a}$,
  (c) $[(C_2-C_5)$-alkenyl]$CH_2-$,
  (d) $[(C_2-C_5)$-alkynyl]$CH_2-$,
  (e) aryl, wherein aryl is defined as phenyl or naphthyl, unsubstituted or substituted with 1 or 2 substituents selected from the group consisting of: Cl, Br, I, F, $(C_1-C_4)$-alkyl, $(C_1-C_4)$-alkoxyl, $NO_2$, $CF_3$, $SO_2NR^{2a}R^{2a}$, $(C_1-C_4)$-alkylthio, hydroxy, amino, $(C_3-C_7)$-cycloalkyl, or $(C_3-C_{10})$-alkenyl,
  (f) aryl$[(C_1-C_6)$-alkyl]$CO-$, or
  (g) $[(C_1-C_6)$-alkyl]$CO-$; and
T is $-S(O)n-$, $-O-$, $-NHCH_2-$, $NHC(=O)-$, $-C(=O)NR^{30}$, or $-N(R^{20})$; and
b is 0 or 1; and
$R^{16}$ is
  (a) $(C_1-C_{10})$-alkyl in which one or more substituent(s) is selected from the group consisting of: hydroxy, oxy, carboxy, $(C_1-C_5)$-alkoxy-carbonyl, $(C_3-C_8)$-cycloalkyl, aryl, or substituted aryl in which the substituents are V and W, and
  (b) aryl, unsubstituted or substituted in which the substituents are V and W;
V and W are each independently selected from:
  (a) H,
  (b) $(C_1-C_5)$-alkoxy,
  (c) $(C_1-C_5)$-alkyl,
  (d) hydroxy,
  (e) $((C_1-C_5)$-alkyl)$S(O)_n$,
  (f) $-CN$,
  (g) $-NO_2$,
  (h) $-NR^2R^{2a}$,
  (i) $[(C_1-C_5)$-alkyl]$CO-NR^2R^{2a}$,
  (j) $-CO_2R^{2a}$,
  (k) $[(C_1-C_5)$-alkyl]$CO-$,
  (l) $CF_3$,
  (m) I, Br, Cl, F,
  (n) hydroxy-$(C_1-C_4)$-alkyl-,
  (o) carboxy-$(C_1-C_4)$-alkyl-,
  (p) -tetrazol-5-yl,
  (q) $-NH-SO_2CF_3$,
  (r) aryl,
  (s) $-O-CONR^2R^{2a}$,
  (t) $NR^{2a}-CO_2R^{2a}$,
  (u) $-NR^{2a}-CONR^{2a}R^{2a}$,
  (v) $-NR^{2a}-CON(CH_2CH_2)_2Q$,
  (w) $-OCON(CH_2CH_2)_2Q$, or
  (x) $-CONR^2R^{2a}$; and
Q is: O, $S(O)_n$, or $NR^{2a}$; and
$R^{20}$ is: H or $(C_1-C_6)$-alkyl; and
heteroaryl is: pyridyl, thienyl, furyl, imidazolyl or thiazolyl.

3. A compound of claim 2 which is

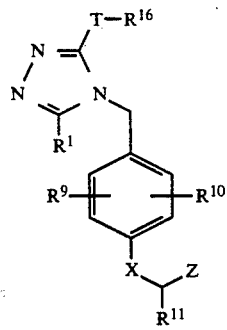

or a pharmaceutically acceptable salt thereof wherein:
$R^1$ is $(C_1-C_6)$-alkyl; and
T is S, or S(=O); and
$R^9$ and $R^{10}$ are: $(C_1-C_6)$-alkyl, $(C_1-C_6)$-alkenyl or $(C_1-C_6)$-alkynyl, $(C_1-C_4)$-alkoxyl, $(C_3-C_8)$-cycloalkyl, Cl, Br, I, F, or aryl; and
X is —$CH_2$—, O or —$NR^{13}$—; and
$R^{11}$ is phenyl, unsubstituted or substituted with 1 to 5 substituents selected from the group consisting of: Br, Cl, F, I, $(C_1-C_4)$-alkyl, $(C_1-C_4)$-alkoxyl, $CF_3$, $NO_2$, $(C_1-C_4)$-alkylthio, OH or $NR^{2a}R^{2a}$; and
$R^{13}$ is: H, $(C_1-C_6)$-alkyl, $[(C_2-C_5)$-alkenyl]$CH_2$—, $[(C_2-C_5)$-alkynyl]$CH_2$— or aryl; and
Z is carboxyl, $CO_2$—$(C_1-C_4)$-alkyl or tetrazol-5-yl; and
$R^{16}$ is benzyl, unsubstituted or substituted in the 2-position or in the 4-position with a substituent selected from the group consisting of: carboxyl, $(C_1-C_4)$-alkyl, Br, Cl, F, or I, methoxy or nitro.

4. A compound which is

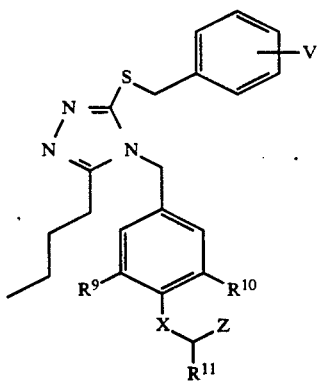

or a pharmaceutically acceptable salt thereof. wherein:
V is: H, 4-Cl, 4-Br, 4-I, 4-F, 4-$NO_2$, 4-$OCH_3$, 4-$CH_3$, 2-$CO_2H$; and
$R^9$ and $R^{10}$ are independently: H, Cl, Br, F, I, $(C_1-C_6)$-alkyl, $(C_2-C_6)$-alkenyl, $(C_2-C_6)$-alkynyl, $(C_1-C_4)$-alkoxyl, $(C_3-C_7)$-cycloalkyl, and
$R^{11}$ is: phenyl, unsubstituted or substituted with substituents selected from the group consisting of: H, Cl, Br, F, I, $CH_3$, or $OCH_3$; and
X is: O or —$NR^{13}$—; and
$R^{13}$ is: H, $(C_1-C_6)$-alkyl, $(C_2-C_6)$-alkenyl, or $(C_2-C_6)$-alkynyl; and
Z is: carboxyl, $CO_2$—$(C_1-C_4)$-alkyl or tetrazol-5-yl; and 5. The compound of claim 1 wherein said compound or its pharmaceutically acceptable salt is selected from the group consisting of:
3-Butyl-4-[[4-(1-carboxy-1-phenylmethoxy)phenyl]-methyl]-5-(4-chlorobenzylthio)-4-H-1,2,4-triazole;
3-Butyl-4-[[4-[1-carboxy-1-phenylmethoxy]phenyl]-methyl]-5-(4-methoxybenzylthio) -4H-1,2,4-triazole;
3-Butyl-4-(1-carboxy-1-phenylmethoxy)phenyl]methyl]-5-(4-nitrobenzylthio)-4H-1,2,4-triazole;
3-Butyl-4-[[4-[1-carboxy-1-(2-chlorophenyl)methoxy]phenyl]methyl]-5-(4-methoxybenzylthio)-4H-1,2,4-triazole;
3-Butyl-4-[[4-[1-carboxy-1-(2-chlorophenyl)methoxy]phenyl]methyl]-5-(4-chlorobenzylthio)-4H-1,2,4-triazole;
3-Butyl-5-(2-carboxybenzylthio)-4-[[4-(1-carboxy-1-phenylmethoxy)phenyl]methyl]-4H-1,2,4-triazole;
3-Butyl-5-(4-nitrobenzylthio)-4-[[4-[1-phenyl-1-(tetrazol-5-yl)methoxy]phenyl]methyl]-4H-1,2,4-triazole;
3-Butyl-4-[[4-(1-carboxy-1-phenylmethoxy)-3-propylphenyl]methyl-5-(4-chlorobenzylthio)-4H1,2,4-triazole;
3-Butyl-4-[[4-(1-carboxy-1-phenylmethoxy)-3-propylphenyl]methyl-5-(4-methoxybenzylthio)-4H-1,2,4-triazole;
3-Butyl-4-[[4-(1-carboxy-1-phenylmethoxy)-3,5-dipropylphenyl]methyl]-5-(4-chlorobenzylthio)-4H-1,2,4-triazole;
3-Butyl-4-[[4-(1-carboxy-1-phenylmethoxy)-3,5-dipropylphenyl]methyl]-5-(4-methoxybenzylthio)-4H-1,2,4-triazole;
3-Butyl-4-[[4-[1-carboxy-1-(2,5-dibromo-3,4-dimethoxyphenyl)methoxy]phenyl]methyl]-5-(4-chlorobenzylthio)4H-1,2,4-triazole;
3-Butyl-4-[[4-[1-carboxy-1-(2,5-dibromo-3,4-dimethoxyphenyl)methoxy]phenyl]methyl]-5-(4-methoxybenzylthio)4H-1,2,4-triazole;
4-[[[N-allyl-N-[(1-carboxy-1-phenyl)methyl]amino]-phenyl]methyl]-3-butyl-5-(4-chlorobenzylthio)-4H-1,2,4-triazole;
3-Butyl-4-[[4-(1-carboxy-1-phenylmethoxy)-3-propylphenyl]methyl]-5-phenyl-4H-1,2,4-triazole;
4-[[[N-allyl-N[(1-carboxy-1-phenyl)methyl]amino]-phenyl]methyl]-3-butyl-5-(4-methoxybenzylthio)-4H-1,2,4-triazole; or
3-Butyl-4-[[[N-[(1-carboxy-1-phenyl)methyl]-N-ethylamino]phenyl]methyl]-5-(4-chlorobenzylthio)-4H-1,2,4-triazole.

6. A pharmaceutical composition useful in the treatment of hypertension which comprises a pharmaceutically acceptable carrier and a therapeutically effective amount of a compound of claim 1.

7. A method of treating hypertension which comprises administering to a patient in need of such treatment a therapeutically effective amount of a compound of claim 1.

8. A method of treating ocular hypertension comprising topical ocular administration to a patient in need of such treatment of an effective ocular antihypertensive amount of a compound of claim 1.

9. A method of treating cognitive dysfunction, anxiety, or depression comprising administering to a patient in need of such treatment, a therapeutically effective amount of a compound of claim 1.

* * * * *